United States Patent
Reens et al.

(10) Patent No.: US 11,110,080 B2
(45) Date of Patent: Sep. 7, 2021

(54) SMALL MOLECULE INHIBITORS OF BACTERIAL EFFLUX PUMPS AND METHODS OF USING SAME

(71) Applicant: The Regents of the University of Colorado, a body Corporate, Denver, CO (US)

(72) Inventors: Abigail L. Reens, Boulder, CO (US); Amy L. Crooks, Erie, CO (US); Corrella S. Detweiler, Boulder, CO (US)

(73) Assignee: The Regents of the University of Colorado, a body corporate, Denver, CO (US)

( * ) Notice: Subject to any disclaimer, the term of this patent is extended or adjusted under 35 U.S.C. 154(b) by 0 days.

(21) Appl. No.: 16/497,315

(22) PCT Filed: Mar. 27, 2018

(86) PCT No.: PCT/US2018/024640
§ 371 (c)(1),
(2) Date: Sep. 24, 2019

(87) PCT Pub. No.: WO2018/183382
PCT Pub. Date: Oct. 4, 2018

(65) Prior Publication Data
US 2020/0022961 A1    Jan. 23, 2020

Related U.S. Application Data

(60) Provisional application No. 62/477,175, filed on Mar. 27, 2017.

(51) Int. Cl.
| | | |
|---|---|---|
| A61K 31/426 | (2006.01) | |
| A61K 31/506 | (2006.01) | |
| A61K 31/517 | (2006.01) | |
| A61K 31/65 | (2006.01) | |
| A61K 38/12 | (2006.01) | |
| C12Q 1/18 | (2006.01) | |

(52) U.S. Cl.
CPC .......... *A61K 31/426* (2013.01); *A61K 31/506* (2013.01); *A61K 31/517* (2013.01); *A61K 31/65* (2013.01); *A61K 38/12* (2013.01); *C12Q 1/18* (2013.01)

(58) Field of Classification Search
CPC .. A61K 31/426; A61K 31/506; A61K 31/517; A61K 38/12
See application file for complete search history.

(56) References Cited

U.S. PATENT DOCUMENTS

| | | |
|---|---|---|
| 2005/0267136 A1 | 12/2005 | Brown et al. |
| 2006/0276473 A1 | 12/2006 | Boston et al. |
| 2007/0225271 A1 | 9/2007 | Binggeli et al. |
| 2008/0261953 A1 | 10/2008 | Lindquist et al. |
| 2013/0296228 A1* | 11/2013 | Patel ............... A61K 38/12 514/2.9 |
| 2015/0018543 A1 | 1/2015 | Brodin et al. |
| 2016/0074379 A1 | 3/2016 | Moy et al. |

FOREIGN PATENT DOCUMENTS

| | | |
|---|---|---|
| WO | 2009049422 A1 | 4/2009 |
| WO | 2015191988 A1 | 12/2015 |

OTHER PUBLICATIONS

Kalia et al., "Capsaicin, a Novel Inhibitor of the NorA Efflex Pump, Reduces the Intracellular Invasion of *Staphylococcus aureus*", Journal of Antimicrobial Chemotherapy 67, pp. 2401-2408, 2012.
Pubchem CID 2790004, pp. 1-14, Jul. 19, 2005.
Pubchem CID 20249286, pp. 1-12, Dec. 12, 2007.
Pubchem CID 446245, pp. 1-17, Jun. 24, 2005.
Kleymann et al., "A Generally Applicable, High-Throughput Screening-Compatible Assay to Identity, Evaluate, and Optimize Antimicrobial Agents for Drug Therapy," Journal of Biomolecular Screening 9(7), pp. 578-587, 2004.
International Search Report issued in PCT Application No. PCT/US18/24640 dated May 25, 2018.
Written Opinion issued in PCT Application No. PCT/US18/24640 dated May 25, 2018.
Li et al., Multicopy Suppressors for Novel Antibacterial Compounds Reveal Targets and Drug Efflux Susceptibility, Chemistry & Biology, vol. 11, pp. 1423-1430, Oct. 2004.
Partial Search Report issued in EP. App. 18777352.8 dated Feb. 12, 2021.

* cited by examiner

*Primary Examiner* — Kamal A Saeed
(74) *Attorney, Agent, or Firm* — Snell & Wilmer LLP

(57) ABSTRACT

An empirical Screen for Anti-infectives using Fluorescence microscopy of IntracellulaR Enterobacteriaceae (SAFIRE) was developed. Using this methodology, a library of small molecules and identified antimicrobials that are cell permeable and non-host-toxic were screened. Inhibitors of bacterial efflux pumps were identified as being implicated in antibiotic resistance and are attractive therapeutic targets for antimicrobials.

11 Claims, 42 Drawing Sheets

Specification includes a Sequence Listing.

| | COMPOUND | | | |
|---|---|---|---|---|
| | PAβN | EPM30 | EPM35 | EPM43 |
| SAFIRE Inhibition (Raw 264.7) | 58.8% [5.9] 500 μM PAβN | 99.4% [0.9] 25 μM EPM30 | 99.1% [1.6] 25 μM EPM35 | 97.8% [2.3] 25 μM EPM43 |
| SAFIRE IC50 (RAW 264.7) | N.D.[1] | 6.9 μM (4.3-11.2) | 3.0 μM (2.1-4.3) | 5.9 μM (3.7-9.5) |
| CFU Inhibition (RAW 264.7) | 5.7.0% [3.8] 500 μM PAβN | 99.4% [0.3] 25 μM EPM30 | 100% [0.02] 25 μM EPM35 | 99.7% [0.2] 25 μM EPM43 |
| MIC in MHB | 2mM | 100 μM | 400 μM | > 400 μM |
| Hoechst Assay EC50 | 488.6 μM (437.5-544.5) | 127.4 μM (110-2-147.2) | 106.2 μM (79.6-141.6) | 119.7 μM (75.9-188.8) |
| LDH assay CC50 (hepG2) | N.D.[1] | 17.2 μM (10.5-28.1) | 10.7 μM (9.1-12.5) | 85.3 μM (36.3-200.5) |
| Predicted logD (ph 7.4) | -1.22 | 2.16 | 2.99 | 3.74 |
| Predicted aqueous solubility | <0.01 mg/ml | 0.01-0.06 mg/ml | <0.01 mg/ml | <0.01 mg/ml |
| Notes | Binds AcrB; disrupts membranes over long exposure | Aminothiazole core present in other EPMs | Related compound may bind AcrB (in silico screen) | Inhibitor of dihydrofolate reductase (candida albicans) |

FIG. 6

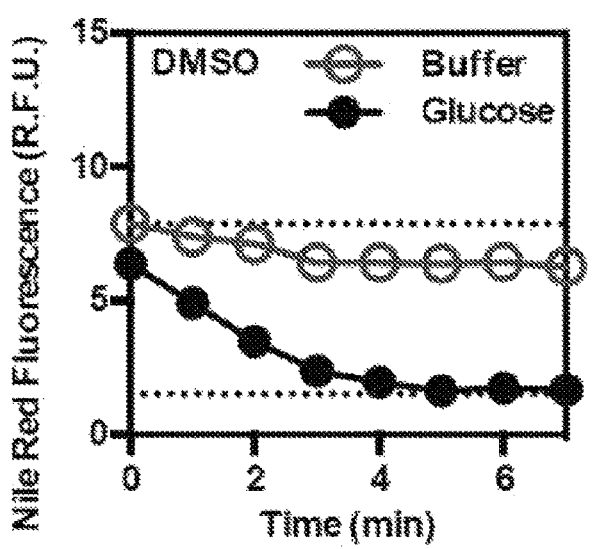
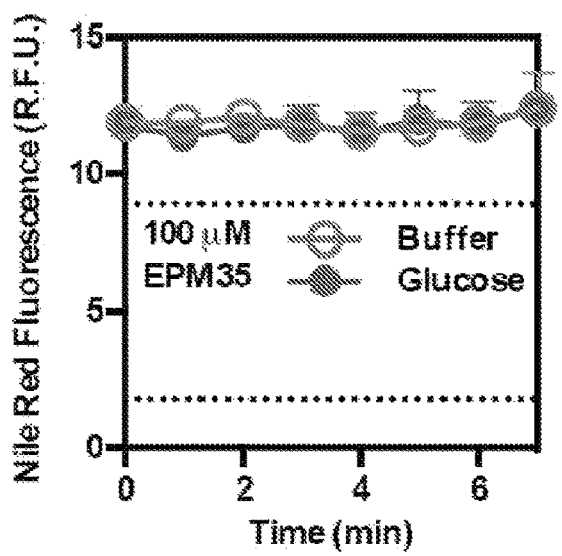
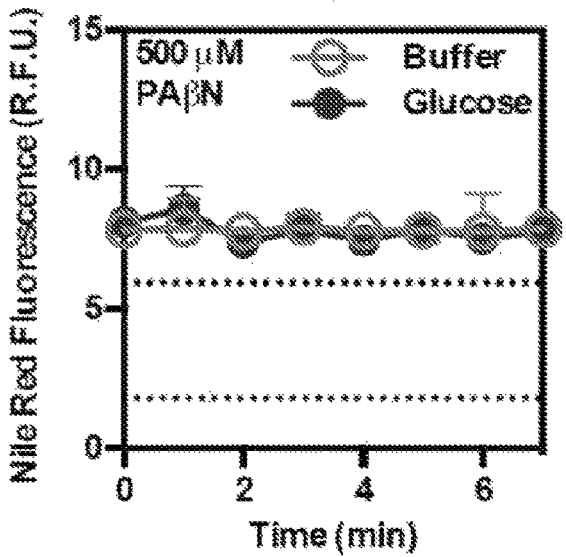
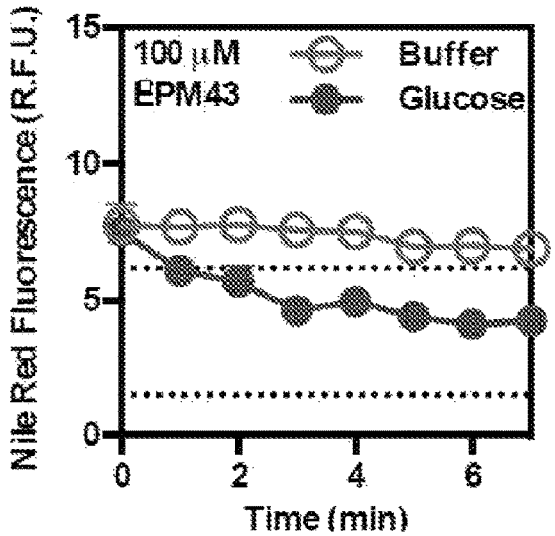
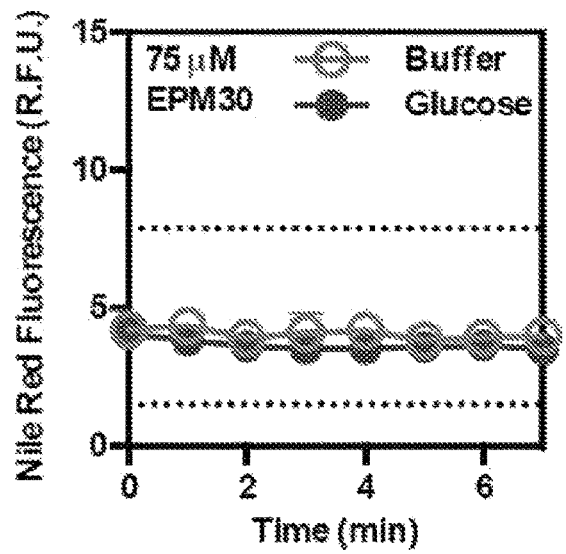
FIG. 7B

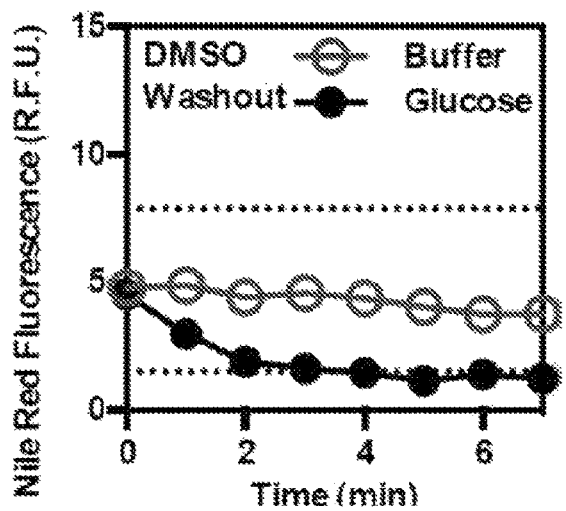
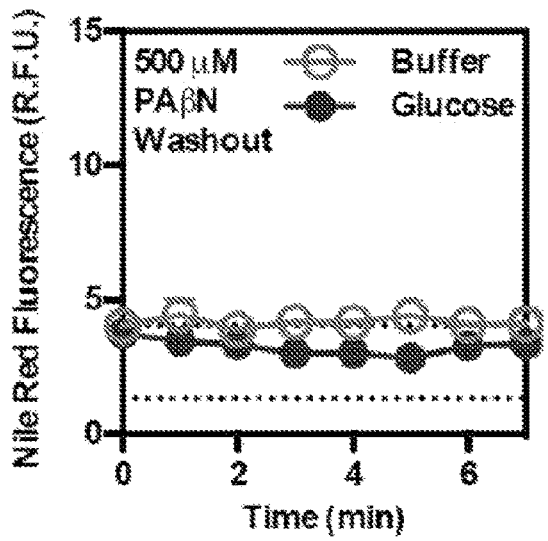
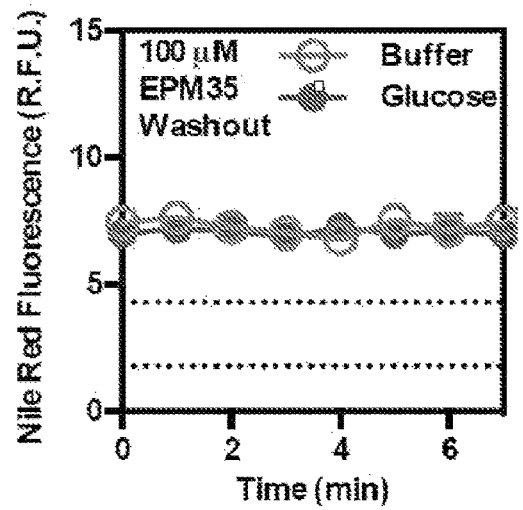
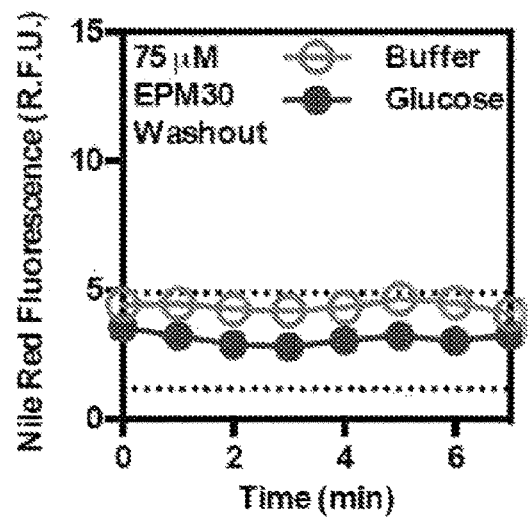
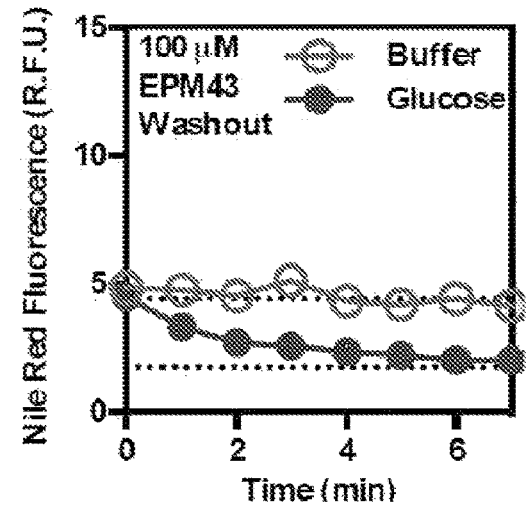
FIG. 7C

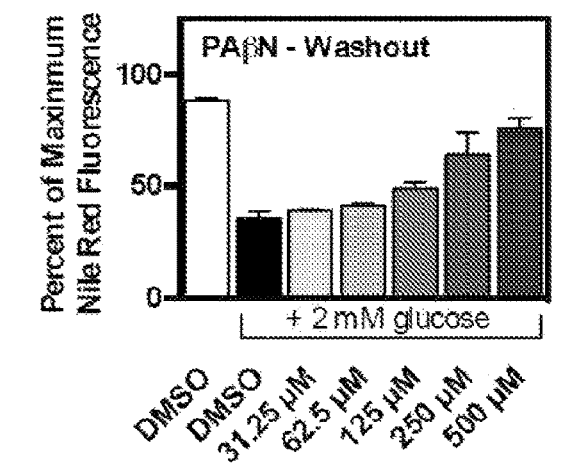
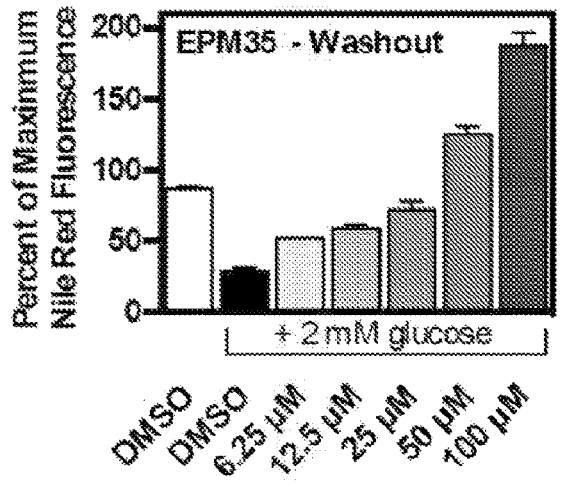
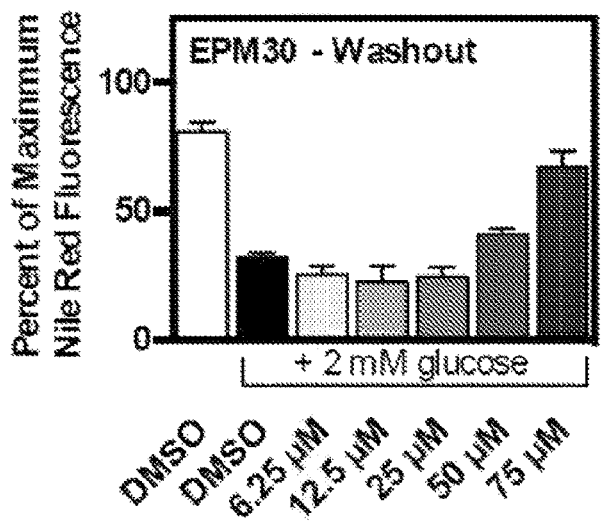
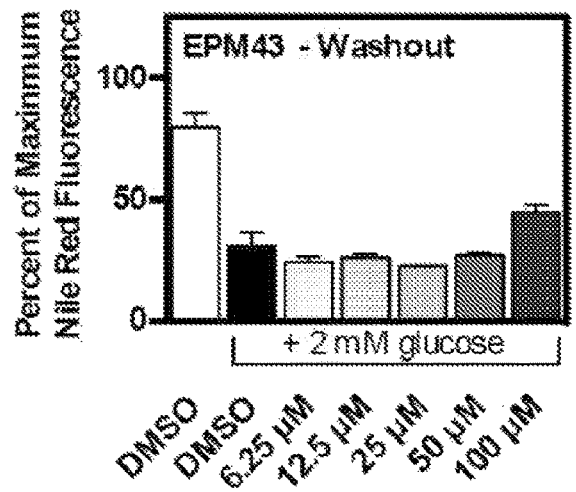
FIG. 7E

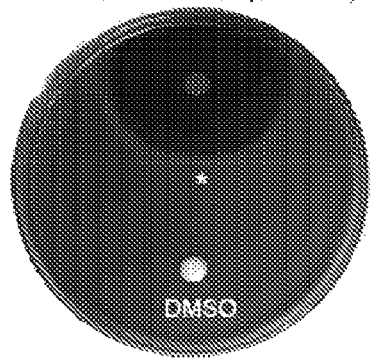
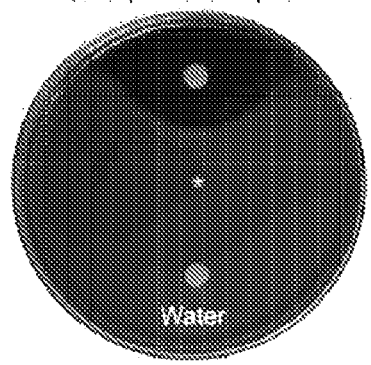
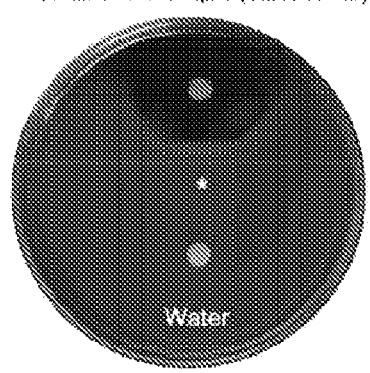
FIG. 9A　　　FIG. 9B　　　FIG. 9C
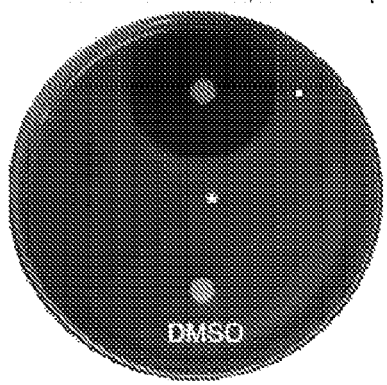
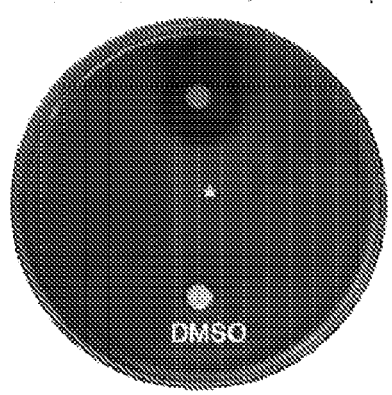
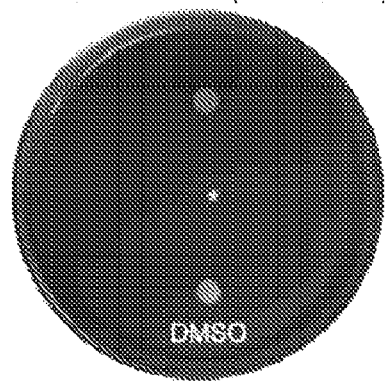
FIG. 9D　　　FIG. 9E　　　FIG. 9F

B.

| | Tet MIC (μg/ml) | EPM35 Concentration (μM) | | | | | | EPM35 MIC (μM) | PAβN Concentration (μM) | | | | | | PAβN MIC (μM) |
|---|---|---|---|---|---|---|---|---|---|---|---|---|---|---|---|
| | | 6.25 | 12.5 | 25 | 50 | 100 | 200 | | 31.25 | 62.5 | 125 | 250 | 500 | 1000 | |
| MAR1 | 4 [2] | 2 (2) | 2 (2) | 2 (2) | 1 (4) | 1 (4) | 0.5 (8) | 400 [1] | 2 (2) | 2 (2) | 1 (4) | 1 (4) | 1 (4) | 0.5 (8) | 2000 [1] |
| S10801 | 128 [64] | 128 (1) | 128 (1) | 64 (2) | 32 (4) | 32 (4) | 32 (4) | 400 [1] | 64 (2) | 64 (2) | 64 (2) | 32 (4) | 16 (8) | 16 (8) | 2000 [1] |
| SL1344 | 2 | 2 (1) | 2 (1) | 0.5 (4) | 0.25 (8) | 0.25 (8) | 0.25 (8) | 400 | 1 (2) | 1 (2) | 0.5 (4) | 0.25 (8) | 0.25 (8) | 0.25 (8) | 2000 |

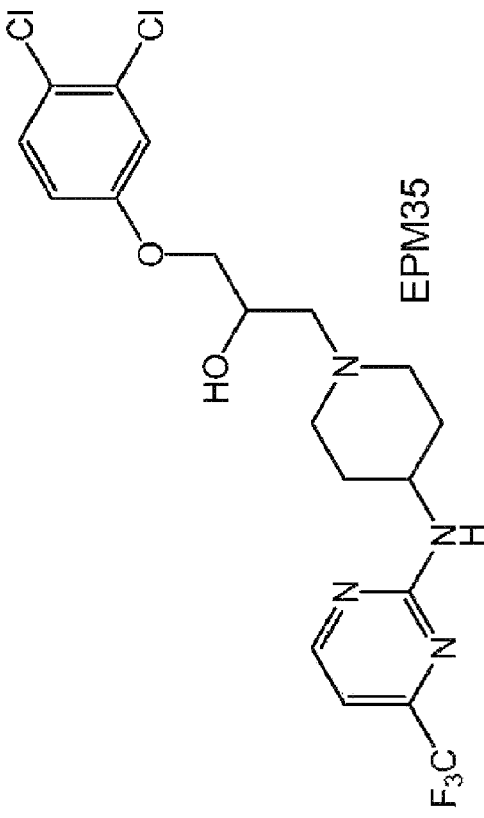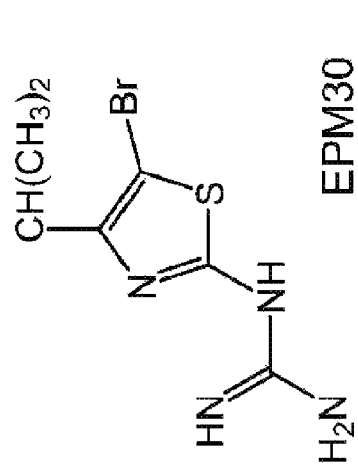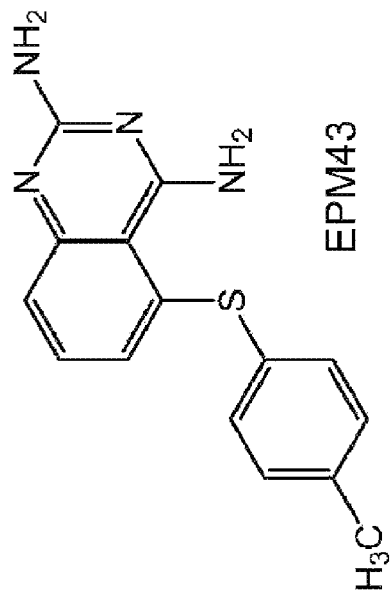
FIG. 17C

US 11,110,080 B2

SMALL MOLECULE INHIBITORS OF BACTERIAL EFFLUX PUMPS AND METHODS OF USING SAME

CROSS-REFERENCE TO RELATED APPLICATIONS

This application is a U.S. national phase filing under 35 U.S.C. § 371 of PCT/US2018/024640 filed on Mar. 27, 2018, entitled "SMALL MOLECULE INHIBITORS OF BACTERIAL EFFLUX PUMPS AND METHODS OF USING SAME," which claims priority to U.S. Provisional Patent Application No. 62/477,175 filed on Mar. 27, 2017 entitled "SMALL MOLECULE INHIBITORS OF BACTERIAL EFFLUX PUMPS," the disclosures of which are incorporated herein by reference.

RESEARCH STATEMENT PURSUANT TO 37 CFR 401.14(a)(b)(1)

This invention was made with government support under grant numbers AI126453, AI121365 and AI095395 awarded by the National Institutes of Health. The government has certain rights in the invention.

FIELD

This disclosure generally relates to small molecule inhibitors of bacterial efflux pumps, and more specifically to treating bacterial infections with such inhibitors.

BACKGROUND

The rise of antibiotic resistance has emphasized the need for novel antimicrobials (Levy S B et al., Nat. Med., S122-129, 2004). Although historical approaches to antibiotic discovery have yielded many crucial therapeutics, recent attempts at identifying new drugs has lagged far behind the spread of resistance. During the golden age of antibiotic discovery in the 1940s and 1950s, actinomycete extracts were screened for growth inhibition of pathogenic bacteria. This empirical platform led to identification of the major classes of antibiotics in use today. However, consistent rediscovery of established molecules led to the abandonment of empirical screening of natural products (Lewis K., Nat. Rev. Drug Discov., 371-387, 2013). Further, this broth-based strategy resulted in inhibitors that targeted core growth processes—translation, DNA replication, and cell wall synthesis. Although highly effective, targeting essential processes leads to strong selection for resistance. In order to focus the search for antimicrobial compounds on targets less likely to lead to resistance, the field shifted toward screening of virulence-specific processes (Allen R C et al., Nat Rev. Microbiol. 300-308, 2014), aided by the advent of genomics and concomitant identification of virulence-associated targets. Some groups have sought to identify virulence inhibitors using broth conditions that mimic the host environment (Yep A et al., mBio, e01089-13-e01089-13, 2014; Hung D T et al., Science, 670-674, 2005). Pharmaceutical companies have invested in high-throughput screening of synthetic chemical libraries for inhibitory activity against validated molecular targets. Over the last 30 years, target-based approaches have yielded zero antibiotics for systemic use, due to a combination of meager hit identification from screens and a widespread lack of antibacterial activity (Lewis K., Nat. Rev. Drug Discov., 371-387, 2013; Payne D J et al., Nat Rev. Drug Discov., 29-40, 2007; Silver L L, Clin. Microbiol. Rev., 71-109, 2001).

The disconnect between biochemical inhibition and antibacterial activity has been attributed to poor intracellular accumulation of small molecules in bacteria (Silver L L, Clin. Microbiol. Rev., 71-109, 2001). In particular, Gram-negative bacteria contain a cell membrane, a cell wall, and an outer membrane. This cell envelope restricts penetration of amphipathic and hydrophilic substances into the cytoplasm and poses a major challenge for antibiotics (Lewis K., Nat. Rev. Drug Discov., 371-387, 2013; Silver L L, Clin. Microbiol. Rev., 71-109, 2001; Denyer S P et al., J. Appl. Microbiol., 92, 2002). Furthermore, bacteria that survive within host cells (e.g. *Salmonella enterica*, *Listeria monocytogenes*, *Staphylococcus aureus*, *Mycobacterium tuberculosis*) are additionally protected by the host cell membrane; some pathogens that survive within vesicles are also shielded by phagosomal membranes. Even traditional antibiotics useful against extracellular pathogens are thus ineffective against intracellular microbes. For instance, aminoglycosides and β-lactams poorly accumulate within host cells and are typically ineffective (Carryn S. et al., Infect. Dis. Clin. North Am., 615-634, 2003; Lamaire S. et al., J. Antimicrob. Chemother., 897-904, 2005; Tulkens P M., Eur J. Clin. Microbiol. Infect. Dis., 100-106, 1991; Maurin M et al., Antimicrob. Agents Chemother., 2977-2986, 2001). Fluoroquinolones primarily localize to the host cell cytosol, and thus are less potent against pathogens within phagosomes (Carryn S. et al., Infect. Dis. Clin. North Am., 615-634, 2003; Carlier M-B et al., J. Antimicorb. Chemother., 27-39, 1990; Pechere J-C, Drugs, 29-36, 1993; Facinelli B., et al., Eur. J. Clin. Microbiol. Infect Dis., 827-833, 1997). Macrolides, although concentrated to high levels within cells, are typically ineffective against vesicular microbes due to inactivation at the low pH of phagolysosomes (Seral C. et al., Antimicrob. Agents Chemother., 2283,-2292, 2003; Labro M T., Clin. Microbiol. Infect., S24-S30, 1996). Similarly, hits from target-based screens typically lack antibacterial activity (Payne D J et al., Nat Rev. Drug Discov., 29-40, 2007; Silver L L, Clin. Microbiol. Rev., 71-109, 2001), as biochemical approaches inherently disregard cell permeability during initial screening. Thus, poor cell permeability represents a key pitfall for virulence-targeted antibacterials.

SUMMARY

SAFIRE, a Screen for Anti-infectives using Fluorescence microscopy of IntracellulaR Enterobacteriaceae, is described in this disclosure. This high-content phenotypic assay uses fluorescence microscopy to identify molecules with antimicrobial activity against intracellular pathogens.

In one aspect, an efflux pump modulator compound having the structure:

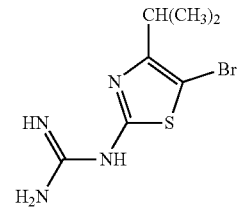

(EPM30) is disclosed for treating a bacterial infection.

In another aspect, an efflux pump modulator compound having the structure:

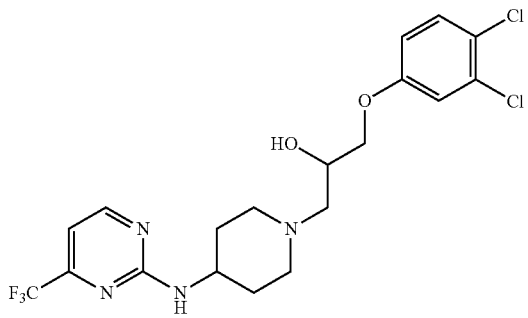 [SMILES: OC(COc1ccc(Cl)c(Cl)c1)CN1CCC(Nc2nccc(C(F)(F)F)n2)CC1]

(EPM35) is disclosed for treating a bacterial infection.

In another aspect, an efflux pump modulator compound having the structure:

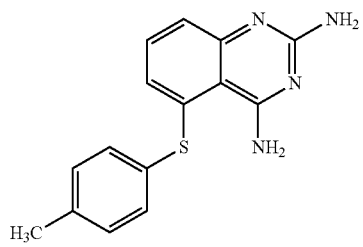 [SMILES: Cc1ccc(Sc2cccc3nc(N)nc(N)c23)cc1]

(EPM43) is disclosed for treating a bacterial infection.

In another aspect, a method of treating a bacterial pathogen in a subject is disclosed. The method comprises administering to the subject a therapeutically effective amount of an efflux pump modulator (EPM) compound.

In embodiments, the method further comprises administering an antimicrobial peptide or an antibiotic. In embodiments, the antibiotic comprises tetracycline or another AcrB antibiotic substrate. In embodiments, the antimicrobial peptide comprises polymyxin B. In embodiments, the EPM compound comprises one of EPM30, EPM35, or EPM43. In embodiments, the EPM compound comprises EPM30. In embodiments, the EPM compound comprises EPM35. In embodiments, the EPM compound comprises EPM43. In embodiments, the bacterial infection comprises an infection with one or more of a *Salmonella* sp., *K. Pneumoniae*, *Enterobacter cloacae*, *Shigella* sp., *Neisseria* sp., or *E. coli*.

In another aspect, a method of treating a bacterial infection in a cell is disclosed. The method comprises contacting the cell with a therapeutically effective amount of an efflux pump modulator (EPM) compound. In embodiments, the cell is an immune cell or a non-immune cell. In embodiments, the immune cell is a macrophage. In embodiments, the method further comprises administering an antimicrobial peptide or an antibiotic. In embodiments, the antibiotic comprises tetracycline. In embodiments, the antimicrobial peptide comprises polymyxin B. In embodiments, the EPM compound comprises one of EPM30, EPM35, or EPM43. In embodiments, the EPM compound comprises EPM30. In embodiments, the EPM compound comprises EPM35. In embodiments, the EPM compound comprises EPM43.

In another aspect, use of an EPM compound for treating a bacterial infection in a subject is disclosed. In embodiments, the EPM compound comprises one of EPM30, EPM35, or EPM43.

In another aspect, a method of identifying an anti-infective compound is disclosed. The method comprises: providing first and second subsets of cells; infecting the first and second subsets of cells with a marker-producing bacteria; staining the first subset of cells with a vitality marker and obtaining a first value of cellular infectivity; contacting the second subset of cells with an anti-infective compound; and staining the second subset of cells with a vitality marker and obtaining a second value of cellular infectivity; wherein when the second value of cellular infectivity is decreased compared to the first value of cellular infectivity, an anti-infective compound is identified. In embodiments, the first and second values of cellular infectivity are obtained by quantifying cells in the first and second subsets of cells using fluorescent microscopy.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIGS. 1-C depicts SAFIRE, a Screen for Anti-infectives using Fluorescence microscopy of IntracellulaR Enterobacteriaceae.

FIG. 2A depicts a screening workflow. FIG. 2B depicts representative microscopy of RAW 264.7 macrophages infected with GFP-S and treated with 25 μM of the indicated compounds. FIG. 2C depicts OD600 measurements for S.Tm grown for 16 hours in MHB with the indicated concentrations of each of the top 58 repurchased hits for rifampicin. Dotted lines indicate OD600 of wells treated with DMSO or rifampicin. Data shown are mean+SD of 2 independent biological replicates.

In FIG. 4, the green square is rifampicin; the blue square is ampicillin; and the purple square is ciprofloxacin, as shown by their respective arrows.

FIG. 5 depicts that EPMs increase Hoechst accumulation.

FIG. 6 depicts characteristics of EPMs. Data shown are from at least 3 independent biological replicates. Standard deviation is shown in brackets; 95% confidence intervals for nonlinear fits are shown in parentheses. 1 SAFIRE IC50 and LDH CC50 was not determined for PAβN due to insolubility of high concentrations in cell culture media.

FIG. 7 depicts that EPMs block efflux of Nile Red. FIGS. 7B and 7D) depict Nile Red-loaded cells incubated with the indicated concentrations of drugs. Glucose or buffer was added and Nile Red fluorescence was monitored. FIGS. 7C and 7E) depicts after incubation with compound; cells were washed to remove compound. Then glucose or buffer was added and Nile Red fluorescence was monitored. FIGS. 7B and 7C depict representative time-course plots from 2 independent biological replicates; dotted lines represent initial Nile Red fluorescence in the same experiment for DMSO-treated cells in the absence of glucose and endpoint fluorescence for MSO-treated cells in the presence of glucose. Error bars represent standard deviation of technical duplicates. FIGS. 7D and 7E depicts that endpoint data (7 minutes) for each treatment condition were normalized to the initial Nile Red fluorescence for DMSO-treated cells in the absence of glucose. Data shown are mean and SEM of 2 biological replicates.

FIG. 8 depicts that DMSO-treated cells efflux Nile Red in the absence of glucose.

FIG. 9 depicts that novel EPMs do not disrupt proton motive force. Bacteria were injected into the center of the plate (indicated with *); 10 μl of the indicated compound or vehicle was spotted onto filter paper disks. Fifteen hours later, plates were imaged. FIGS. 9A-9F depict representative images.

FIG. 13 depicts that EPMs do not require transcription or translation for antibacterial activity.

FIG. 15 depicts that drugs are active against S.Tm in HeLa cells. FIG. 15B depicts mean+SEM of three independent biological replicates. FIG. 15C depicts representative microscopy from one experiment. *$p<0.05$; **$p<0.01$ compared to DMSO by one-way ANOVA with Tukey's post-test.

FIG. 16 depicts that EPM35 increases sensitivity of MDR S.Tm to tetracycline in vitro and in vivo. FIG. 16B depicts MICs of tetracycline (μg/ml) for indicated strains in the presence of the indicated concentrations of EPM35 or PAβN. Parentheses represent fold difference in tetracycline MIC compared to 0 μM drug; brackets indicate fold difference in MIC for different strains compared to wild type.

FIG. 17 depicts that three hit compounds increase Hoechst accumulation in Salmonella. FIG. 17C depicts structures of three EPMs.

(FIG. 18C) BMDMs, FIGS. 18D-F) RAW264.7 830 cells infected for two hours with *Salmonella* (SL1344 or the indicated strain) and then treated with the indicated compound for 16 hours, followed by macrophage lysis and plating for CFU. Geometric mean and SEM of four biological replicates. *p<0.05, p<0.01; *p<0.001, ****p<0.0001 relative to DMSO, one-way ANOVA with Dunnett's post-test. Dotted lines, mean CFU/well of wild-type SL1344 with DMSO treatment; horizontal lines, limit of detection.

FIG. 19 depicts that EPMs block efflux of Nile Red and Ethidium bromide. *Salmonella* were incubated with either Nile Red or Ethidium bromide without glucose, treated with compound, exposed to glucose, and then monitored for fluorescence.

FIG. 20 depicts that EPMs do not disrupt bacterial inner or outer membranes. FIG. 20A depicts representative data from one of three independent experiments. FIG. 20B depicts median fluorescence intensity from three experiments normalized to unstained control (0). FIG. 20D depicts absorbance 486 nm of bla+ *Salmonella* normalized to bla− *Salmonella*. Data is representative of 3-4 independent biological replicates. FIG. 20E depicts slope of the linear region of the A486 plot from at least three experiments. Data is normalized to A486/minute. *p<0.05, *p<0.001, **p<0.0001 by one-way ANOVA with Dunnett's post-test.

FIG. 22 depicts that EPM35 and EPM43 block efflux of Nile Red from 896 ESKAPE MDR clinical isolates.

DETAILED DESCRIPTION

Figure 1A:
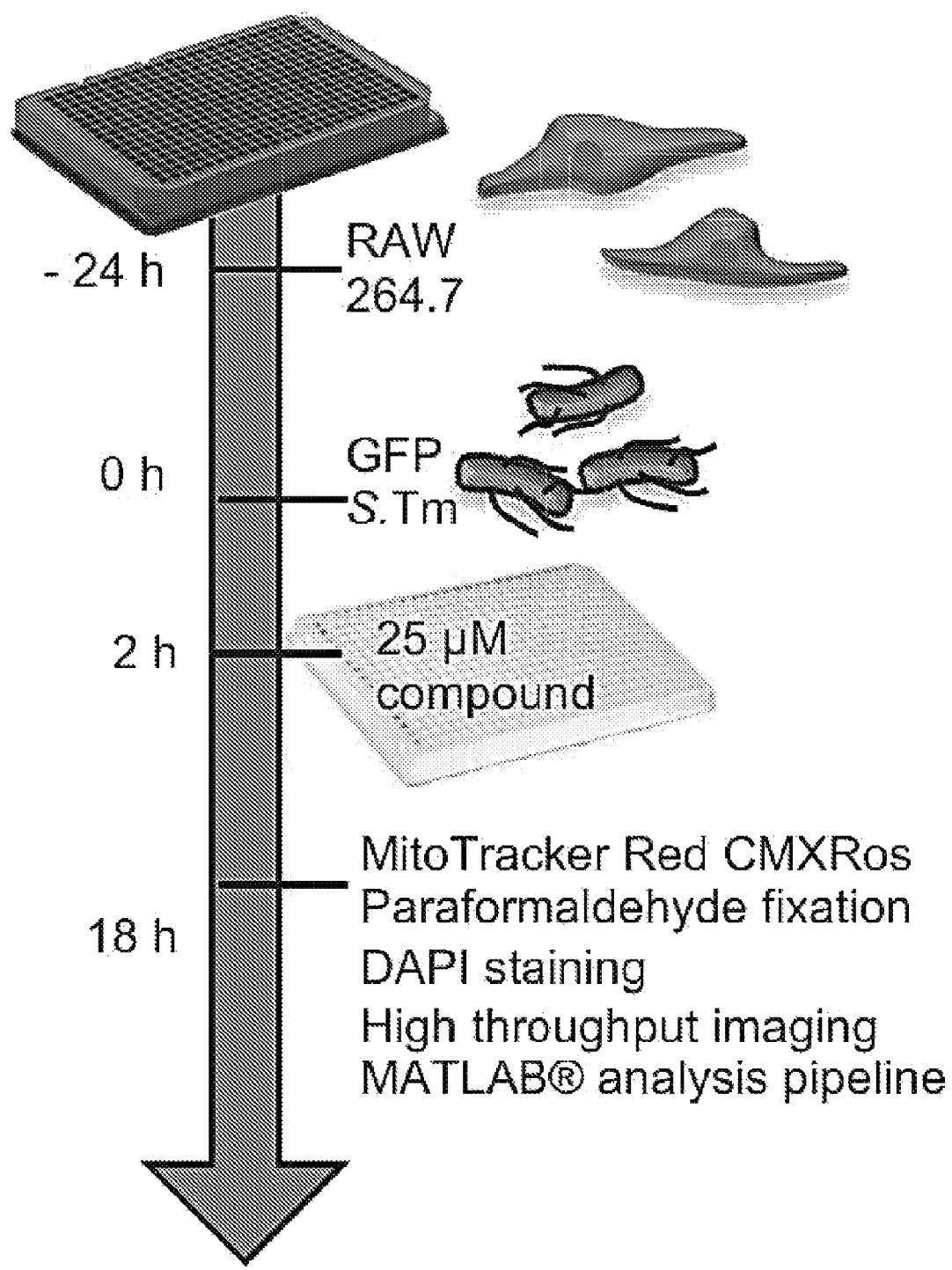
FIG. 1A depicts a schematic of screening methodology.

The Gram-negative intracellular pathogen, *Salmonella enterica* serovar *Typhimurium* (*Salmonella*) (S.Tm) causes a natural infection of mice that models the human disease typhoid fever. S.Tm survives and replicates inside macrophages in systemic sites, and resides within a specialized phagolysosomal vesicle during infection. Assay platforms can be used that utilize fluorescent S.Tm, immortalized mouse macrophages, and automated fluorescence microscopy to visualize bacterial load. A MATLAB®-based algorithm was developed to process images for high-throughput quantification. Using this platform, a 14,400-compound Maybridge Hitfinder™ Collection v11 was screened. There were 309 hits identified that reduced intracellular bacterial infection with minimal host cell toxicity. The majority of the hits have not been previously identified as having antibacterial activity. Similarly, very few hits possess antibiotic activity against bacteria grown in standard microbiological media. Thus, the screen represents a powerful approach to identify antibacterial compounds within existing libraries by directly assaying bacterial infection of host cells.

Top hits were tested from the screen to determine whether any compounds inhibit bacterial efflux pumps (EPs). EPs are an attractive therapeutic target for antimicrobials and anticancer drugs, but most have proved troublesome for drug development due to toxicity issues. EPs utilize active transport to export chemicals, small molecules, and peptides. Although EPs are naturally important for defense against host-derived antimicrobials such as antimicrobial peptides and reactive oxygen species, many multidrug resistant (MDR) pathogens have increased expression of EPs, thereby limiting antibiotic exposure. S.Tm encodes nine EPs which contribute to antibiotic efflux and also attenuate or delay virulence in vivo. In particular, the EPs encoded by the acrAB and macAB operons are both required for infection of macrophages and mice. Thus, efflux pump modulators (EPMs) have potential as therapeutics for ordinary and MDR infections by sensitizing pathogens to host defenses and clinical antibiotics. Hits from SAFIRE may represent unidentified EPMs that enhance susceptibility to host antimicrobials present within macrophages. Top hits were tested from the screen to determine whether they inhibit bacterial efflux. This resulted in characterization of three novel EPMs.

Definitions and Interpretation

Unless otherwise defined herein, scientific and technical terms used in connection with the present disclosure shall have the meanings that are commonly understood by those of ordinary skill in the art. Further, unless otherwise required by context, singular terms shall include pluralities and plural terms shall include the singular. Generally, nomenclature used in connection with, and techniques of, cell and tissue culture, molecular biology, immunology, microbiology, genetics and protein and nucleic acid chemistry and hybridization described herein are those well-known and commonly used in the art. The methods and techniques of the present disclosure are generally performed according to conventional methods well-known in the art and as described in various general and more specific references that are cited and discussed throughout the present specification unless otherwise indicated. See, e.g.: Sambrook J. & Russell D. Molecular Cloning: A Laboratory Manual, 3rd ed., Cold Spring Harbor Laboratory Press, Cold Spring Harbor, N.Y. (2000); Ausubel et al., Short Protocols in Molecular Biology: A Compendium of Methods from Current Protocols in Molecular Biology, Wiley, John & Sons, Inc. (2002); Harlow and Lane, Using Antibodies: A Laboratory Manual; Cold Spring Harbor Laboratory Press, Cold Spring Harbor, N.Y. (1998); and Coligan et al., Short Protocols in Protein Science, Wiley, John & Sons, Inc. (2003).

As used herein, the acronym "AcrB" refers to the efflux transporter AcrB.

As used herein, the acronym "AMP" refers to antimicrobial peptide.

As used herein, the acronym "EP" refers to efflux pump.

As used herein, the acronym "EPM" refers to efflux pump modulator compounds.

As used herein, the acronym "PAβN" refers to the following chemical structure:

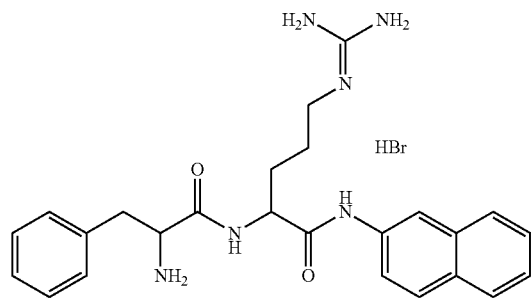 [SMILES: NC(N)=NCCCC(NC(=O)C(N)Cc1ccccc1)C(=O)Nc1ccc2ccccc2c1 ; Br]

As used herein, the acronym "SAFIRE" refers to Screen for Anti-infectives using Fluorescence microscopy of IntracellulaR Enterobacteriaceae, as detailed herein.

As used herein, the term "S.Tm" refers to *Salmonella enterica* serovar *Typhimurium*.

For the purposes of this disclosure, all chemical compounds described or structurally illustrated herein include all stereoisomers and tautomers thereof.

Description of Aspects of the Disclosure

In one aspect, an efflux pump modulator compound having the structure:

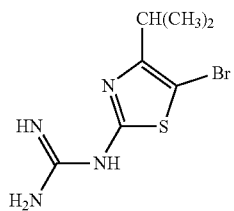

(EPM30) is disclosed for treating a bacterial infection.

In another aspect, an efflux pump modulator compound having the structure:

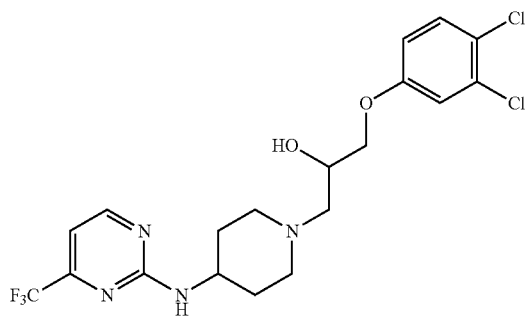 [SMILES: OC(COc1ccc(Cl)c(Cl)c1)CN1CCC(Nc2nccc(C(F)(F)F)n2)CC1]

(EPM35) is disclosed for treating a bacterial infection.

In another aspect, an efflux pump modulator compound having the structure:

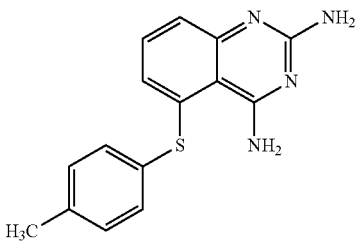 [SMILES: Cc1ccc(Sc2cccc3nc(N)nc(N)c23)cc1]

(EPM43) is disclosed for treating a bacterial infection.

In another aspect, a method of treating a bacterial pathogen in a subject is disclosed. The method comprises administering to the subject a therapeutically effective amount of an efflux pump modulator (EPM) compound.

In embodiments, the method further comprises administering an antimicrobial peptide or an antibiotic. In embodiments, the antibiotic comprises tetracycline. In embodiments, the antimicrobial peptide comprises polymyxin B. In embodiments, the EPM compound comprises one of EPM30, EPM35, or EPM43. In embodiments, the EPM compound comprises EPM30. In embodiments, the EPM compound comprises EPM35. In embodiments, the EPM compound comprises EPM43. In embodiments, the bacterial infection comprises an infection with one or more Gram-positive or Gram-negative bacterial species. In embodiments, the bacterial infection comprises an infection with one or more of a *Salmonella* sp., *K. Pneumoniae, Enterobacter cloacae*, or *E. coli*.

In another aspect, a method of treating a bacterial infection in a cell is disclosed. The method comprises contacting the cell with a therapeutically effective amount of an efflux pump modulator (EPM) compound. In embodiments, the cell is an immune cell or a non-immune cell. In embodiments, the immune cell is a macrophage. In embodiments, the method further comprises administering an antimicrobial peptide or an antibiotic. In embodiments, the antibiotic comprises tetracycline. In embodiments, the antimicrobial peptide comprises polymyxin B. In embodiments, the EPM compound comprises one of EPM30, EPM35, or EPM43. In embodiments, the EPM compound comprises EPM30. In embodiments, the EPM compound comprises EPM35. In embodiments, the EPM compound comprises EPM43.

In another use, use of an EPM compound for treating a bacterial infection in a subject is disclosed. In embodiments, the EPM compound comprises one of EPM30, EPM35, or EPM43.

In another aspect, a method of identifying an anti-infective compound is disclosed. The method comprises: providing first and second subsets of cells; infecting the first and second subsets of cells with a marker-producing bacteria; staining the first subset of cells with a vitality marker and obtaining a first value of cellular infectivity; contacting the second subset of cells with an anti-infective compound; and staining the second subset of cells with a vitality marker and obtaining a second value of cellular infectivity; wherein when the second value of cellular infectivity is decreased compared to the first value of cellular infectivity, an anti-infective compound is identified. In embodiments, the first and second values of cellular infectivity are obtained by quantifying cells in the first and second subsets of cells using fluorescent microscopy.

Doses, Dosage Forms, and Methods of Treatment

In embodiments, any of the compounds disclosed herein may be administered to treat a bacterial infection to a subject in need. In embodiments, any of the compounds disclosed herein may be administered for a prophylactic treatment. In embodiments, any of the compounds disclosed herein may be administered for a therapeutic treatment. In embodiments, the method of administration varies depending on the bacteria involved and the severity of the infection. Dosing regimens may vary based upon the condition being treated and the method of administration. In embodiments, the subject is given an effective amount of the compounds. An effective amount is the amount required to treat or prevent a bacterial infection. In embodiments, any of the compounds described herein are mixed with a suitable carrier substance. In embodiments, the compound is mixed with the suitable carrier substance in an amount of 1-99% by weight of the total weight of the composition.

In embodiments, any of the compounds described herein may be administered periodically, such as once or twice a day, or any other suitable time period. For example, compounds may be administered to a subject in need once a week, once every other week, once every three weeks, once a month, every other month, every three months, every six months, every nine months, once a year, every eighteen months, every two years, every thirty months, or every three years.

In embodiments, the duration of the treatment may be at least 1 day, at least 5 days, at least 10 days, at least 15 days, at least 20 days, at least 25 days, at least 30 days, at least 35 days, at least 40 days, at least 45 days, at least 50 days, at least 55 days, at least 60 days, at least 65 days at least 70 days, at least 75 days, at least 80 days, at least 85 days, at least 90 days, at least 95 days, or at least 100 days.

In embodiments, any of the compounds disclosed herein are administered as a pharmaceutical composition. In embodiments, the pharmaceutical composition comprising any of the compounds described herein can be formulated in a wide variety of dosage forms, including but not limited to nasal, pulmonary, oral, topical, or parenteral dosage forms for clinical application. Each of the dosage forms can comprise various solubilizing agents, disintegrating agents, surfactants, fillers, thickeners, binders, diluents such as wetting agents or other pharmaceutically acceptable excipients. The pharmaceutical composition comprising a compound can also be formulated for injection, insufflation, infusion, or intradermal exposure. For instance, an injectable formulation may comprise the disclosed compounds in an aqueous or non-aqueous solution at a suitable pH and tonicity.

In embodiments, the pharmaceutical composition comprises any of the compounds disclosed herein and an antibiotic selected from penicillin G, penicillin V, methicillin, oxacillin, cloxacillin, dicloxacillin, nafcillin, ampicillin, amoxicillin, carbenicillin, ticarcillin, mezlocillin, piperacillin, azlocillin, temocillin, cepalothin, cephapirin, cephradine, cephaloridine, cefazolin, cefamandole, cefuroxime, cephalexin, cefprozil, cefaclor, loracarbef, cefoxitin, cefmatozole, cefotaxime, ceftizoxime, ceftriaxone, cefoperazone, ceftazidime, cefixime, cefpodoxime, ceftibuten, cefdinir, cefpirome, cefepime, BAL5788, BAL9141, imipenem, ertapenem, meropenem, astreonam, clavulanate, sulbactam, tazobactam, streptomycin, neomycin, kanamycin, paromycin, gentamicin, tobramycin, amikacin, netilmicin, spectinomycin, sisomicin, dibekalin, isepamicin, tetracycline, chlortetracycline, demeclocycline, minocycline, oxytetracycline, methacycline, doxycycline, erythromycin, azithromycin, clarithromycin, telithromycin, ABT-773, lincomycin, clindamycin, vancomycin, oritavancin, dalbavancin, teicoplanin, quinupristin and dalfopristin, sulphanilamide, para-aminobenzoic acid, sulfadiazine, sulfisoxazole, sulfamethoxazole, sulfathalidine, linezolid, nalidixic acid, oxolinic acid, norfloxacin, perfloxacin, enoxacin, ofloxacin, ciprofloxacin, temafloxacin, lomefloxacin, fleroxacin, grepafloxacin, sparfloxacin, trovafloxacin, clinafloxacin, gatifloxacin, moxifloxacin, gemifloxacin, sitafloxacin, metronidazole, daptomycin, garenoxacin, ramoplanin, faropenem, polymyxin, tigecycline, AZD2563, and trimethoprim.

The disclosed compounds may be administered to a subject via direct injection into the bacterial cells. In embodiments, the compounds can be administered systemically. In embodiments, the compounds can be administered via guided cannulation to tissues immediately surrounding the sites of tumor or infection.

In embodiments, any of the compounds disclosed herein can be administered using any pharmaceutically acceptable method, such as intranasal, buccal, sublingual, oral, rectal, ocular, parenteral (intravenously, intradermally, intramuscularly, subcutaneously, intraperitoneally, intralesionally), pulmonary, intravaginal, locally administered, topically administered, topically administered after scarification, mucosally administered, via an aerosol, in semi-solid media such as agarose or gelatin, or via a buccal or nasal spray formulation. In embodiments, the method of administration is a systemic administration. In embodiments, the method of administration is a musculoskeletal administration.

In embodiments, any of the compounds disclosed herein can be formulated into any pharmaceutically acceptable dosage form, such as a solid dosage form, tablet, pill, lozenge, capsule, liquid dispersion, gel, aerosol, pulmonary aerosol, nasal aerosol, ointment, cream, semi-solid dosage form, a solution, an emulsion, and a suspension. In embodiments, any of the compounds disclosed herein can be formulated into any pharmaceutically acceptable dosage form, such as a hydrogel, paste, plaster, drench, suppository, enema, injectable, or implant. In embodiments, any of the formulations described herein may be a controlled release formulation, sustained release formulation, immediate release formulation, or any combination thereof. In embodiments, the formulation may be a transdermal delivery system.

In embodiments, the pharmaceutical composition comprising any of the compounds disclosed herein can be formulated in a solid dosage form for oral administration, and the solid dosage form can be powders, granules, capsules, tablets or pills. In embodiments, the solid dosage form can include one or more excipients such as calcium carbonate, starch, sucrose, lactose, microcrystalline cellulose or gelatin. In embodiments, the solid dosage form can include, in addition to the excipients, a lubricant such as talc or magnesium stearate. In embodiments, the oral dosage form can be immediate release, or a modified release form. Modified release dosage forms include controlled or extended release, enteric release, and the like. The excipients used in the modified release dosage forms are commonly known to a person of ordinary skill in the art.

In embodiments, the pharmaceutical composition comprising any of the compounds disclosed herein can be formulated as a sublingual or buccal dosage form. Such dosage forms comprise sublingual tablets or solution compositions that are administered under the tongue and buccal tablets that are placed between the cheek and gum.

In embodiments, the pharmaceutical composition comprising any of the compounds disclosed herein can be formulated as a nasal dosage form. Such dosage forms of the present invention comprise solution, suspension, and gel compositions for nasal delivery.

In some embodiments, the pharmaceutical composition comprising any of the compounds disclosed herein can be formulated in a liquid dosage form for oral administration, such as suspensions, emulsions or syrups. In some embodiments, the liquid dosage form can include, in addition to commonly used simple diluents such as water and liquid paraffin, various excipients such as humectants, sweeteners, aromatics or preservatives. In embodiments, the composition comprising any of the compounds disclosed herein can be formulated to be suitable for administration to a pediatric patient.

In embodiments, the pharmaceutical composition can be formulated in a dosage form for parenteral administration, such as sterile aqueous solutions, suspensions, emulsions, non-aqueous solutions or suppositories. In embodiments, the solutions or suspensions can include propyleneglycol, polyethyleneglycol, vegetable oils such as olive oil or injectable esters such as ethyl oleate.

The dosage of the pharmaceutical composition can vary depending on the patient's weight, age, gender, administration time and mode, excretion rate, and the severity of disease.

In some embodiments, the treatment of the bacteria is accomplished by guided direct injection of any of the compounds disclosed herein, using needle, or intravascular cannulation. In some embodiments, the disclosed vectors are administered into the cerebrospinal fluid, blood or lymphatic circulation by venous or arterial cannulation or injection, intradermal delivery, intramuscular delivery or injection into a draining organ near the site of disease.

Bacterial Infections

In embodiments, any of the compounds described herein can be used to treat any bacterial infections. In embodiments, a bacterial infection is invasion of bacteria into a host. In embodiments, this invasion results in excessive growth of bacteria. In embodiments, the invasion results in growth of bacteria in the host that is not normally present in the host.

Bacterial infections include any bacterial infection caused by or associated with *Salmonella* sp., *K. Pneumoniae, Enterobacter cloacae, Shigella* sp., *Neisseria* sp., or *E. coli*, but are not limited to, bacterial pneumonia, urinary tract infections, intra-abdominal infections, skin and skin structure infections, bone and joint infections, central nervous center infections, gastro-intestinal tract infections, pelvic inflammatory diseases. Diseases associated with bacterial infections, include, but are not limited to rheumatoid arthritis, fibromyalgia, autonomic nervous dysfunction, multiple sclerosis, interstitial cystitis, multiple sclerosis, and chronic fatigue.

EXAMPLES

Figure 1B:
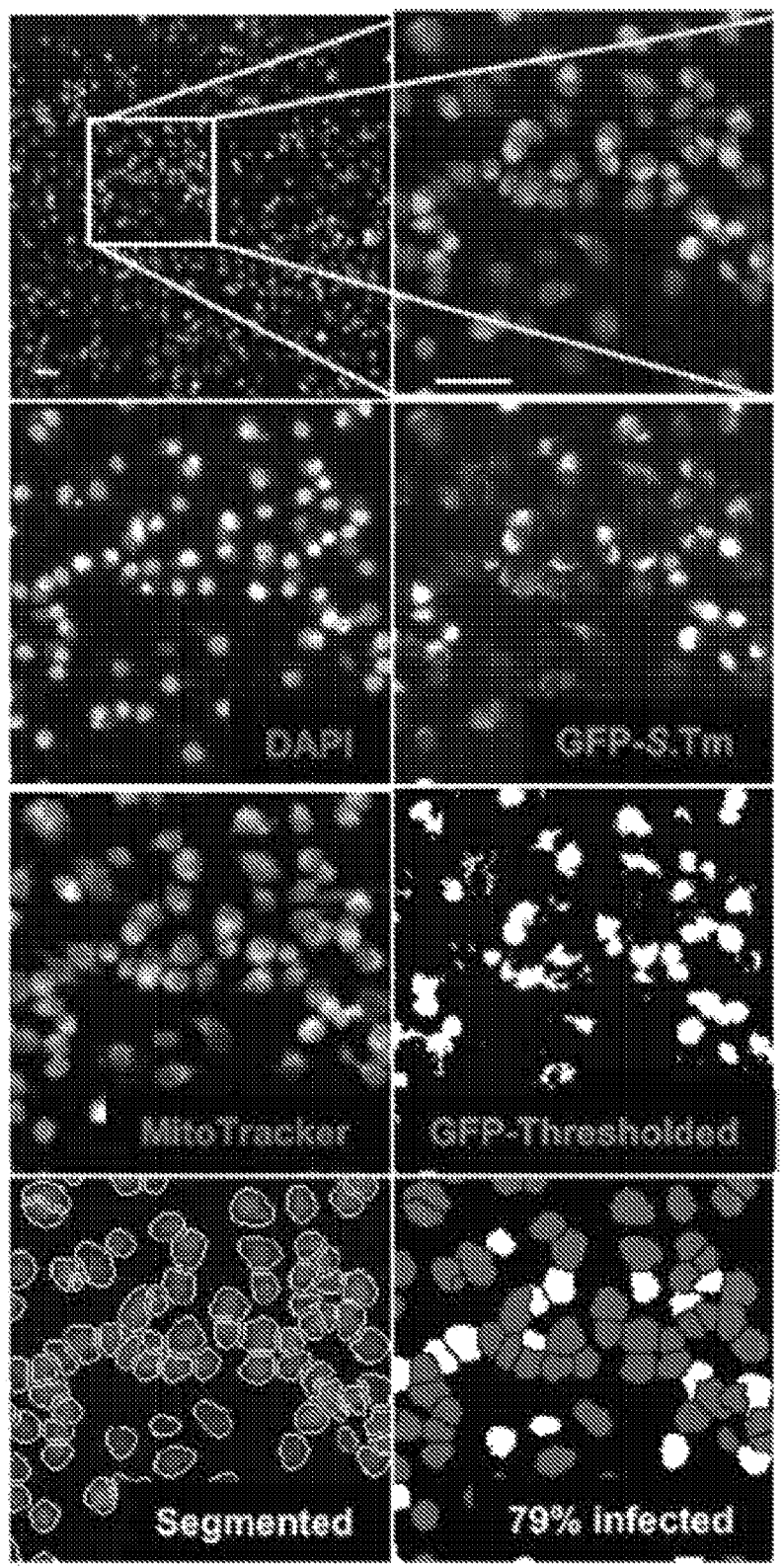
FIG. 1B depicts a representative microscopy analysis of DMSO-treated wells. The upper left image is a single field with 522 macrophages; remaining images are the indicated channels in the boxed region. Scale bars are 50 μm.

Example 1. Development of SAFIRE, a Screen for Anti-Infectives Using Fluorescence Microscopy of IntracellulaR Enterobacteriaceae A high-content, high-throughput fluorescence microscopy-based screening platform to assay S.Tm load within macrophages was developed (FIG. 1A). RAW 264.7 murine macrophages, a widely used cell line for bacterial infection studies, were infected with bacteria in a standard gentamicin protection assay. The *Salmonella* expressing GFP driven by the sifB promoter was incubated with the compound beginning at 2 hours post-infection. At 18 hours post-infection, cells were stained with MitoTracker Red CMXRos as a marker of macrophage vitality and processed for fluorescence microscopy. Stained with DAPI. A MATLAB®-based algorithm was developed to quantify infection (FIG. 1B) and compared to statistics to describe infection. Percentage of infected cells was determined by counting the proportion of macrophages within an image with at least 2 GFP+ pixels. Infection area was calculated by normalizing the number of GFP+ pixels within a cell to the cell's total area, then averaging across all cells in an image. To evaluate the approach, 2 µg/ml rifampicin in 96-well and 384-well plates was tested in three independent replicates. The Z'-factor was employed as a measure of assay reproducibility. Numbers close to 1 indicated high reproducibility. For percentage of infected macrophages, the Z'-factor was 0.59 and 0.48 in 96-well and 384-well plates, respectively, compared with 0.66 and 0.38 for infection area. The optimal Z'-factor threshold for high-throughput screening was 0.5; however, values above 0 were considered marginal but feasible. Therefore, the percentage of infected macrophages statistic was used.

Figure 1C:
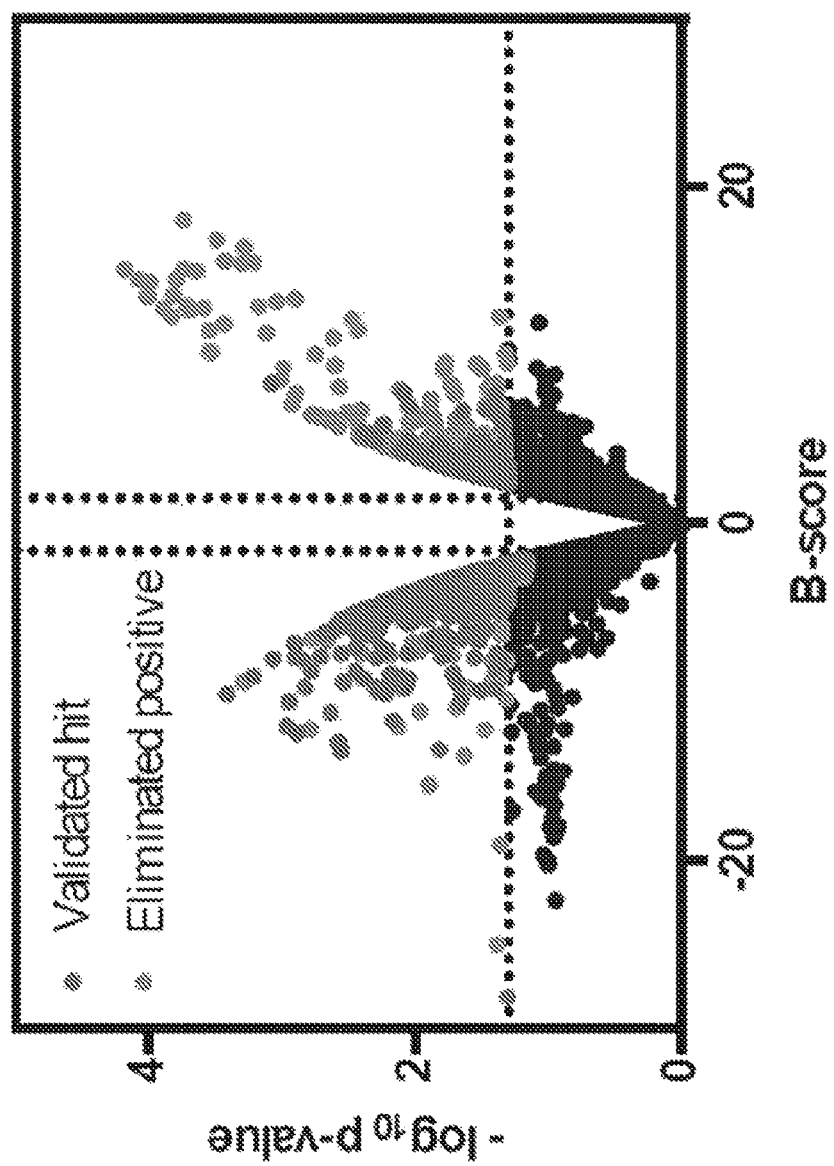
FIG. 1C depicts a distribution of B-scores and p-values for 14,400 compounds from the Maybridge HitFinder™ v11 library.
Figure 2A:
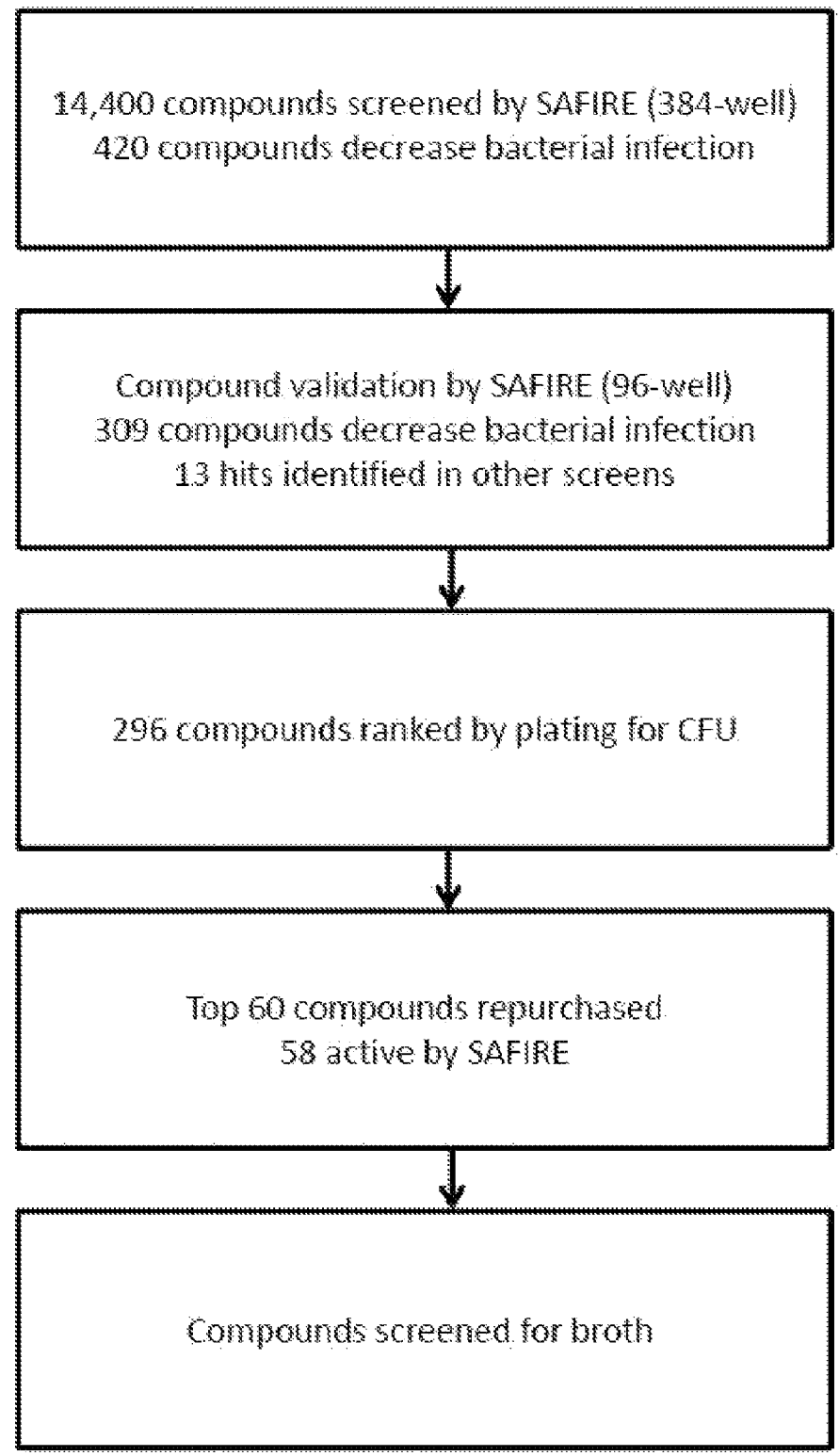
FIGS. 2A-C depict the identification and characterization of antimicrobials.

Example 2. Identification of Small Molecules that Reduce *Salmonella* Load in Macrophages The 14,400 compound library Maybridge HitFinder™ v11 was screened, which has been extensively screened against mammalian and microbial targets. The library was screened in duplicate at 25 µM in 384-well plates (FIG. 1C). Data were normalized using the B-score method to remove positional variation. The significance of B-scores was calculated using a modified t-test assuming an inverse gamma distribution of variances. Using a dual threshold of B-score greater than 1 and standard deviation from the mean and p-value less than 0.05, 908 compounds (6.3%) were identified that decreased or increased the percentage of infected macrophages. Microscopy images were manually reviewed to eliminate toxic and auto-fluorescent compounds, and the remaining positives were retested using SAFIRE in 96-well plates, which demonstrated higher Z'-factors as described above (FIGS. 2A,-B). Compounds that altered infection by at least 25% in 96-well plates were considered validated hits. This analysis revealed 309 compounds (2.1%) that decreased infection and 137 (0.95%) that increased infection.

Of the 309 compounds that decreased the percentage of infected macrophages, 13 have been previously identified to have activity against microbes. In particular, amongst the compounds identified were chloramphenicol, a known antibiotic, and 9-aminoacridine, which has been used topically as an antiseptic. Other compounds identified included an inhibitor of activation of PhoP, a S.Tm virulence determinant and an inhibitor of MbtI, a siderophore biosynthesis enzyme in *Mycobacterium tuberculosis*. Several of the other compounds have been found in high-throughput screens against microbes including hepatitis C, influenza, malaria, trypanosomes, and *Candida albicans*. Furthermore, 33 compounds were identified that have known activities in mammalian cells, including inhibitors of calcium channels, telomerase, TGF-beta, and NFκB. To estimate the frequency of false negatives in the screen, drugs and substances were catalogued in the Maybridge HitFinder™ v11 library using the Chemical Structure Lookup Service from the CADD Group Chemoinformatics Tools and User Services (see: Table 1).

TABLE 1

Substances in the Maybridge Hitfinder ™ v11 chemical library

| Name | Known Activity | Code | Location |
|---|---|---|---|
| Santowax M | Heat Transfer Fluid | BTB10963 | 002_E05 |
| Naproxen | Anti-inflammatory | SB01071 | 003_F08 |
| Heteroauxin | Hormone | RH01882 | 004_D02 |
| Clomipramine[1] | Antidepressant | RJC01223 | 007_F04 |
| Kinetin | Hormone | RJC03303 | 008_D02 |
| Mycanodin | Antifungal | JFD01904 | 008_H09 |
| Tolzamide | Hypoglycemic agent | JFD01580 | 013_D07 |
| Pyrithyldione | Sedative | JFD03934 | 018_H07 |
| Lipoamide | Metabolite | JFD01918 | 023_G11 |
| Chloramphenicol[1] | Antibiotic | JFD01781 | 028_F05 |
| Diphencyprone | Immunostimulant | BTB10303 | 042_G05 |
| Glyburide | Antihypoglycemic agent | RJC01668 | 048_H11 |
| Arecoline | Cholinergic agonist | SB01660 | 049_D02 |
| Tolfenamic acid | Anti-inflammatory | JFD01579 | 069_E08 |
| 9-aminoacridine[1] | Antiseptic | NRB04719 | 095_D11 |
| Tolnaftate | Antifungal | BTB13928 | 096_D04 |
| Xylitol | Artificial sweetener | NRB05167 | 117_B03 |
| Menadione | Synthetic vitamin | SB01122 | 124_F03 |
| Indoramin[1] | Antihypertensive | RH01633 | 140_B11 |
| Carboxin | Antifungal | XBX00001 | 140_E03 |
| Phenylbiguanide | Serotonin receptor agonist | RJF01059 | 142_H09 |
| Coumarin 4 | Anticoagulant | BTB10013 | 146_B04 |
| 6-aminopenicillinate[2] | Metabolite | SB01619 | 146_B07 |
| Nithiamide | Antiprotozoan | JFD03897 | 157_C10 |
| Nalidixic acid[2] | AntiMicrobial | RJC03974 | 162_E02 |
| Hydroflumethiazide | Diuretic | SB01887 | 164_F08 |
| Phenytoin | Anticonvulsant | BTB14870 | 170_C02 |

[1]Compounds identified as hits in SAFIRE screen.
[2]Substances with known antibacterial activity not identified as hits in SAFIRE screen; 6-aminopenicillinate was just below the screening threshold and nalidixic acid was inactive in one replicate.

Figure 3:
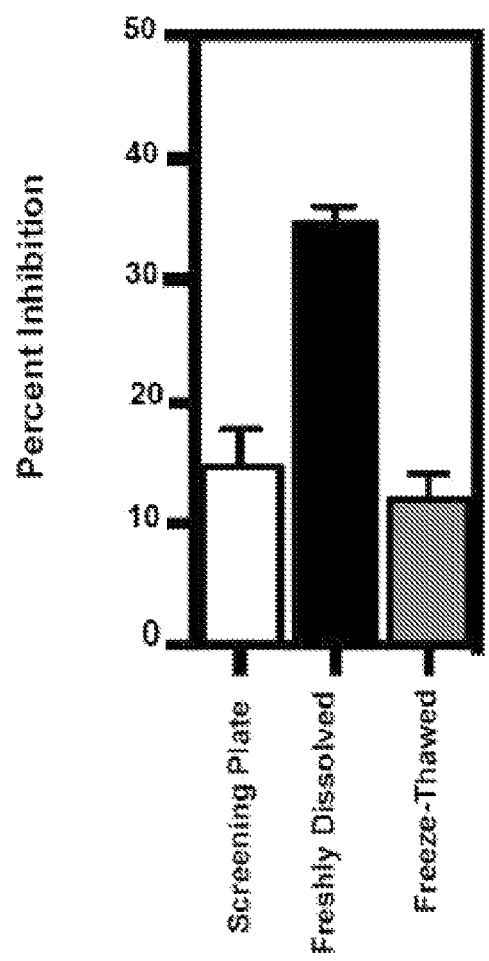
FIG. 3 depicts that nalidixic acid dissolved in DMSO is sensitive to freeze-thawing. SAFIRE was used to quantify infection of macrophages treated with 25 μM nalidixic acid that was cherry-picked from the plates used to perform the screen (n=2), freshly dissolved in DMSO (n=3), or freshly dissolved and freeze thawed 20 times (n=3). Data are mean+SEM.

There were two drugs with antibiotic activity present in the library that were not found in the screen: 6-aminopenicillinate and nalidixic acid. The screening data was re-examined to investigate why these antibiotics were not identified. 6-aminopenicillinate is a synthetic precursor to the beta-lactam antibiotics, and showed modest activity in the screen. Although the average B-score for 6-aminopenicillinate from the screen (−2.29) was beyond the threshold (−2.17), the p-value (0.056) was just above the threshold (0.05), suggesting that the use of a dual threshold increased selectivity for highly active and reproducible compounds. Nalidixic acid is a synthetic quinolone and displayed substantial activity in the first replicate of the screen (B-score −4.41), but was inactive in the second replicate (B-score 0.70). The original screening plate well was subsequently, which again showed minimal activity; further experiments suggested that nalidixic acid is sensitive to freeze-thawing when dissolved in DMSO (FIG. 3).

Figure 4:
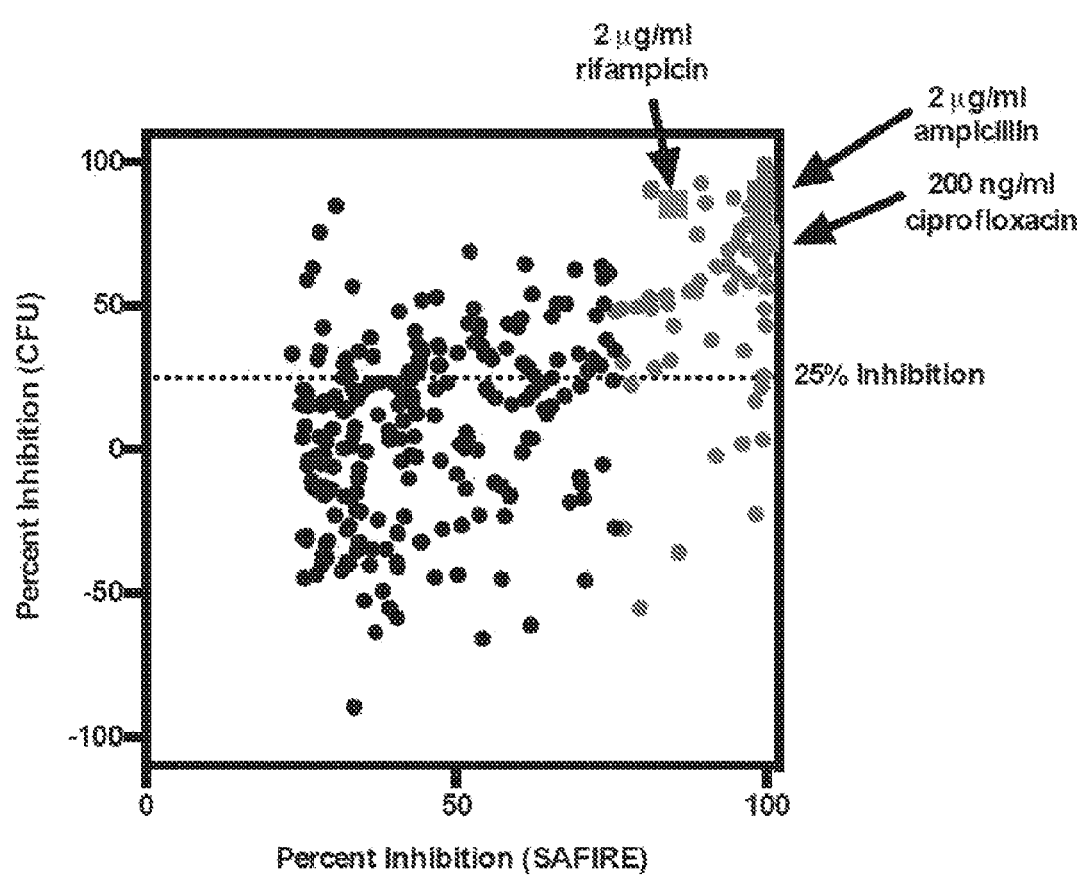
FIG. 4 depicts compound activity in SAFIRE versus compound activity in CFU assays. The top 75 compounds are represented with red dots.

To further categorize our hit compounds, 296 was re-tested for anti-S.Tm activity using gentamicin protection assays and plating for colony forming units (CFUs). Macrophages were infected in 96-well plates and treated with 25 µM compound. At 18 hours post-infection, macrophages were lysed to release intracellular bacteria and lysates were diluted and plated to determine CFUs. Although known bacteriostatic antibiotics such as rifampicin, ampicillin, and ciprofloxacin show similar inhibition by the CFU assay as by SAFIRE, only half of the hits displayed significant (>25%) inhibition by the CFU plating (FIG. 4). However, 64 of the top 75 compounds as ranked by SAFIRE exhibited significant activity by the CFU assay, suggesting that most highly active compounds are robust in both assays.

Example 3. Top Hits do not Inhibit Bacterial Growth in Broth

Figure 2B:
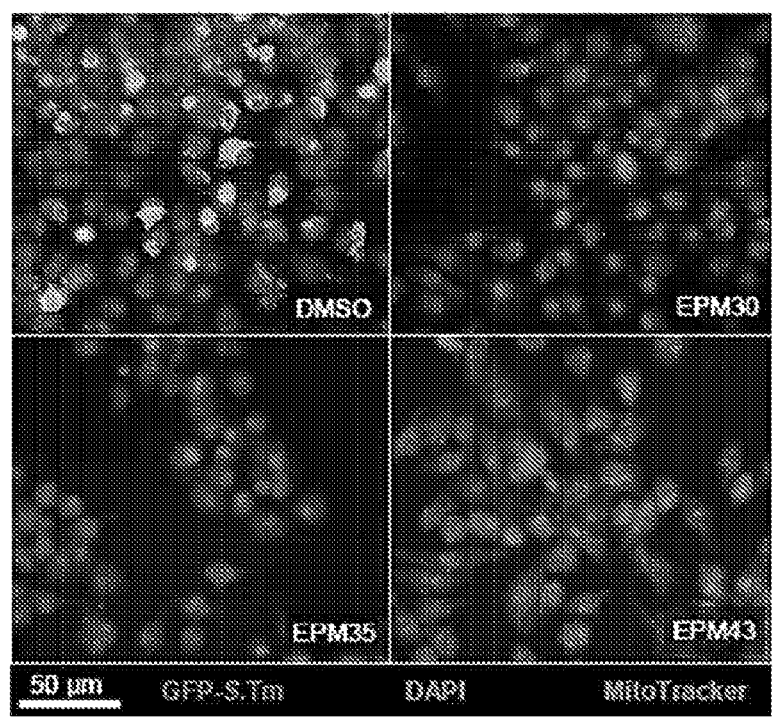
Figure 2C:
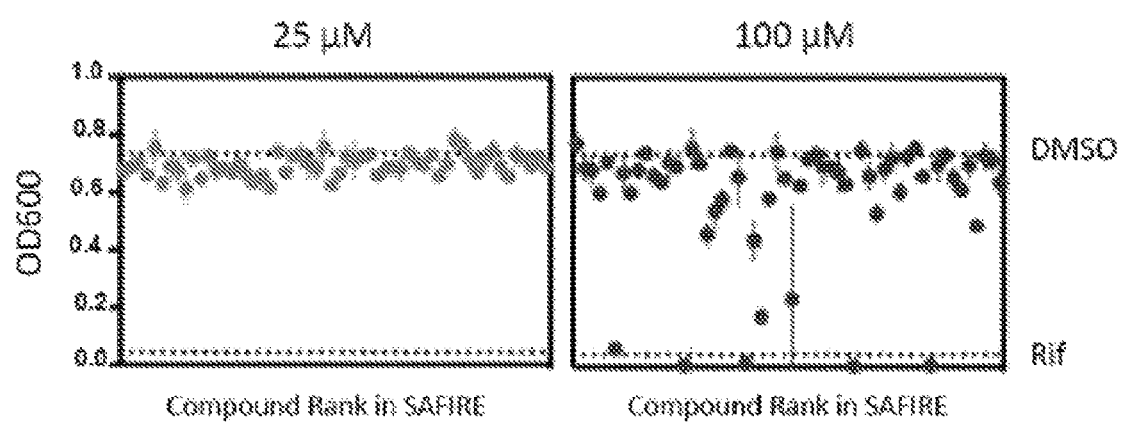

Sixty of the top hits were repurchased and each confirmed activity by SAFIRE. Fifty-eight repurchased compounds were active with IC50s ranging from 0.5-10.5 µM. These top 58 hits were screened for activity against extracellular S.Tm grown in MHB broth (FIG. 2C). At 25 µM, none of the compounds reduced S.Tm growth. Even at 100 µM, only a few of the hits inhibited or reduced growth, which indicates that these top hits may target bacterial virulence or the host and would not have been identified in a broth-based screen.

Example 4. Three Compounds Inhibit Efflux of Fluorescent Dyes

Figure 5A:
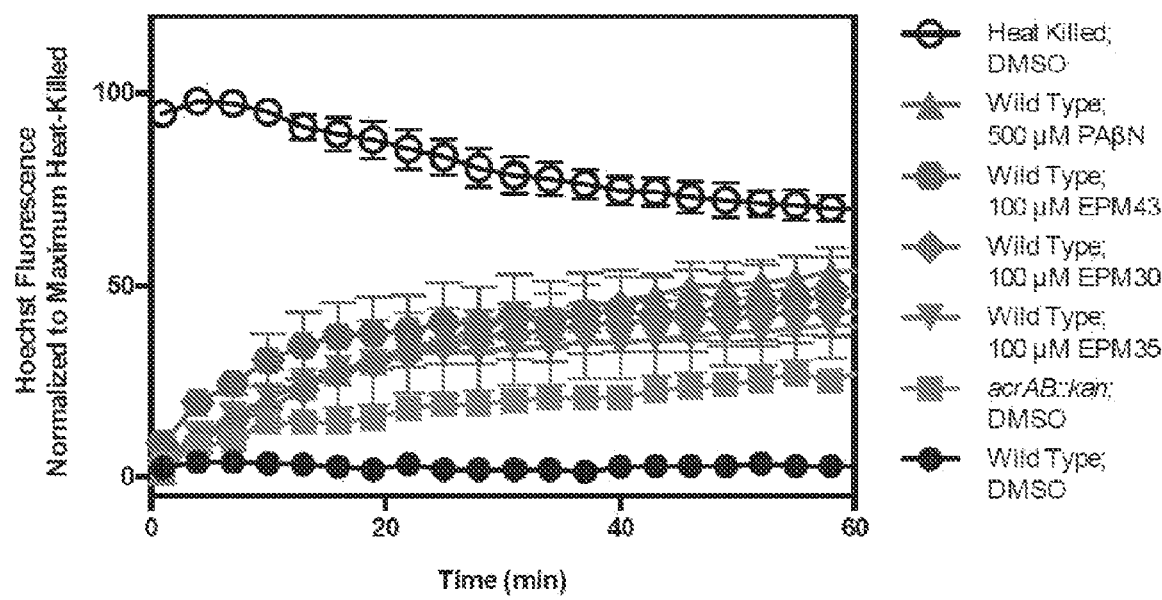
FIG. 5A depicts timecourse plots of Hoechst fluorescence of S.Tm incubated in Hoechst 33342 and the indicated EPMs.
Figure 5B:
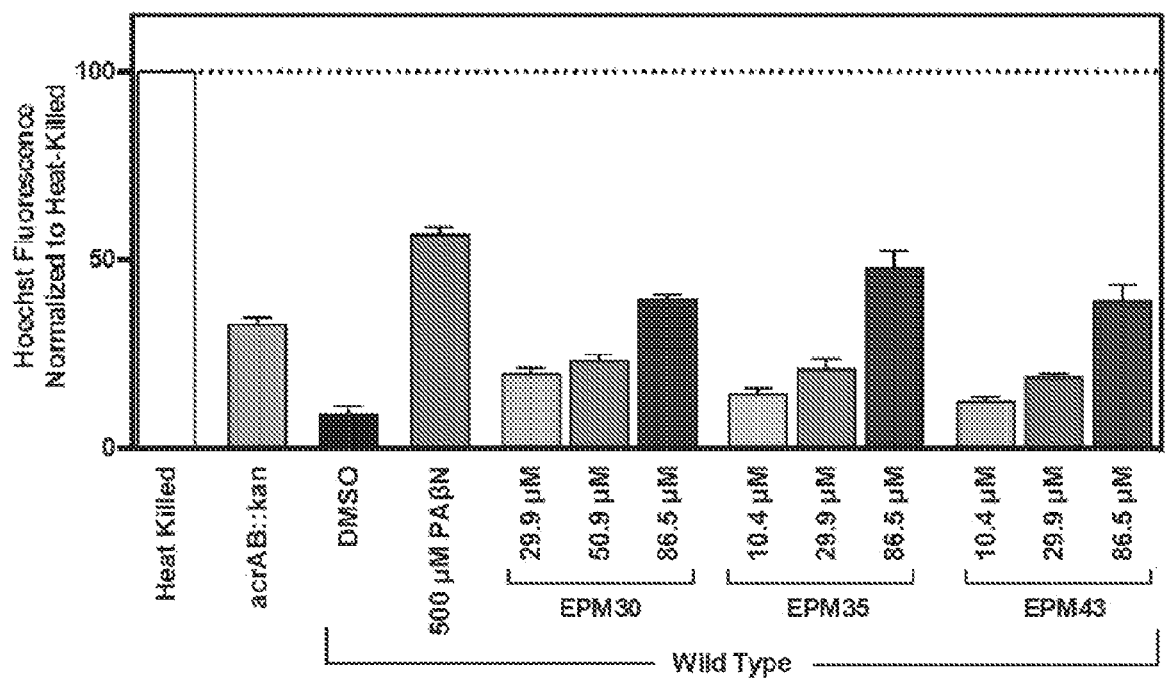
FIG. 5B depicts quantification of maximum Hoechst fluorescence. Data shown are mean+SEM of 3 independent biological replicates.

Efflux pumps (EPs) represent a key pathogen virulence strategy to protect against host antimicrobials as well as therapeutic antibiotics. Furthermore, efflux pump modulators (EPMs) typically demonstrate high MICs as single agents, similar to our hits (FIG. 2C). Thus, EPMs may have been identified by our screen due to cooperation with host antimicrobials. To uncover putative EPMs within our collection of hits, 58 repurchased compounds were screened in a Hoechst accumulation assay. Bacteria were incubated with Hoechst 33342, a dye which fluoresces when bound to DNA. Heat-killed bacteria exhibited very high fluorescence immediately after exposure to the dye, as all DNA was bound by Hoechst (FIG. 5A, open circles; FIG. 5B, white). After 60 minutes of exposure, wild-type S.Tm exhibited low fluorescence, likely because Hoechst is effluxed before it binds DNA. Hoechst accumulation increased in a strain lacking the AcrAB efflux pump (FIG. 5, black vs. gray) and a wild-type strain incubated with EPM Phe-Arg β-naphthylamide (PAβN) (FIG. 5A). Three of the top 58 compounds also increased S.Tm accumulation of Hoechst in a dose-dependent manner (FIG. 5A, red (EPM30), green (EPM35), blue (EPM43), with EC50s lower than that of PAβN (FIG. 6).

Figure 7A:
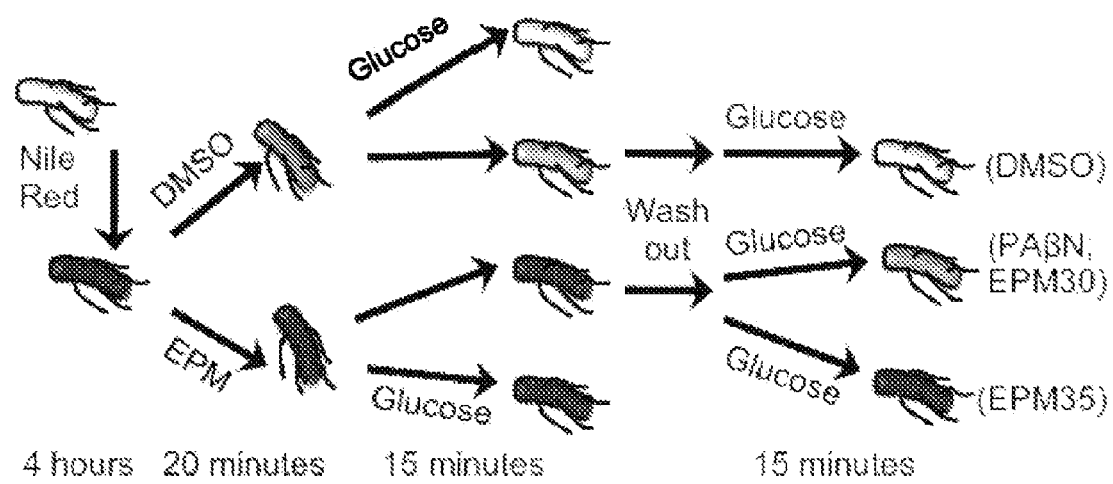
FIG. 7A depicts wild-type S.Tm loaded with Nile Red, a fluorescent dye that associates with the outer membrane and is exported by Eps upon addition of glucose. Relative Nile Red fluorescence is indicated by the color of the bacterium in the schematic.

Because Hoechst and other dyes commonly used to assess efflux bind cellular components, direct measurement of efflux is not possible using these methods; instead, the Hoechst assay measures dye accumulation, the net result of entry and efflux. Further, the slow off-rate of Hoechst entails that efflux pumps have no effect on dye already bound to DNA. As a result, compounds which increase Hoechst accumulation may actually enhance dye entry by altering porins or disrupting the membrane. To more specifically measure efflux pump activity, a second technique was employed using the dye Nile Red, a lipophilic membrane-partitioning dye which fluoresces in nonpolar environments. Because Nile Red is not known to bind cellular components, to directly observe efflux cells were preloaded with the dye in the absence of glucose to reduce efflux pump activity (FIG. 7A). Upon addition of glucose, bacteria rapidly effluxed Nile Red and fluorescence returned to baseline levels (FIG. 7B, top panel). Treatment with 500 μM PAβN inhibited glucose-activated efflux (FIG. 7B, second panel). The initial measured fluorescence was lower for DMSO-treated cells (upper dotted line) than for PAβN-treated cells due to glucose-independent efflux during sample preparation (FIG. 8A). Next, it was determined whether efflux pump activity is restored after removal of PAβN. Bacteria were incubated with compound for 15 minutes, pelleted and resuspended in buffer lacking compound, and then stimulated with glucose (FIGS. 7C, 7E). Washout of PAβN partially restored the ability of S.Tm to efflux Nile Red upon glucose addition, which is consistent with PAβN specifically binding efflux pumps during short incubations rather than disrupting the outer membrane. Nile Red fluorescence was quantified at 7 minutes post-glucose addition for several doses of PAβN and observed dose dependent inhibition of Nile Red efflux (FIGS. 7D, 7E).

Figure 7D:
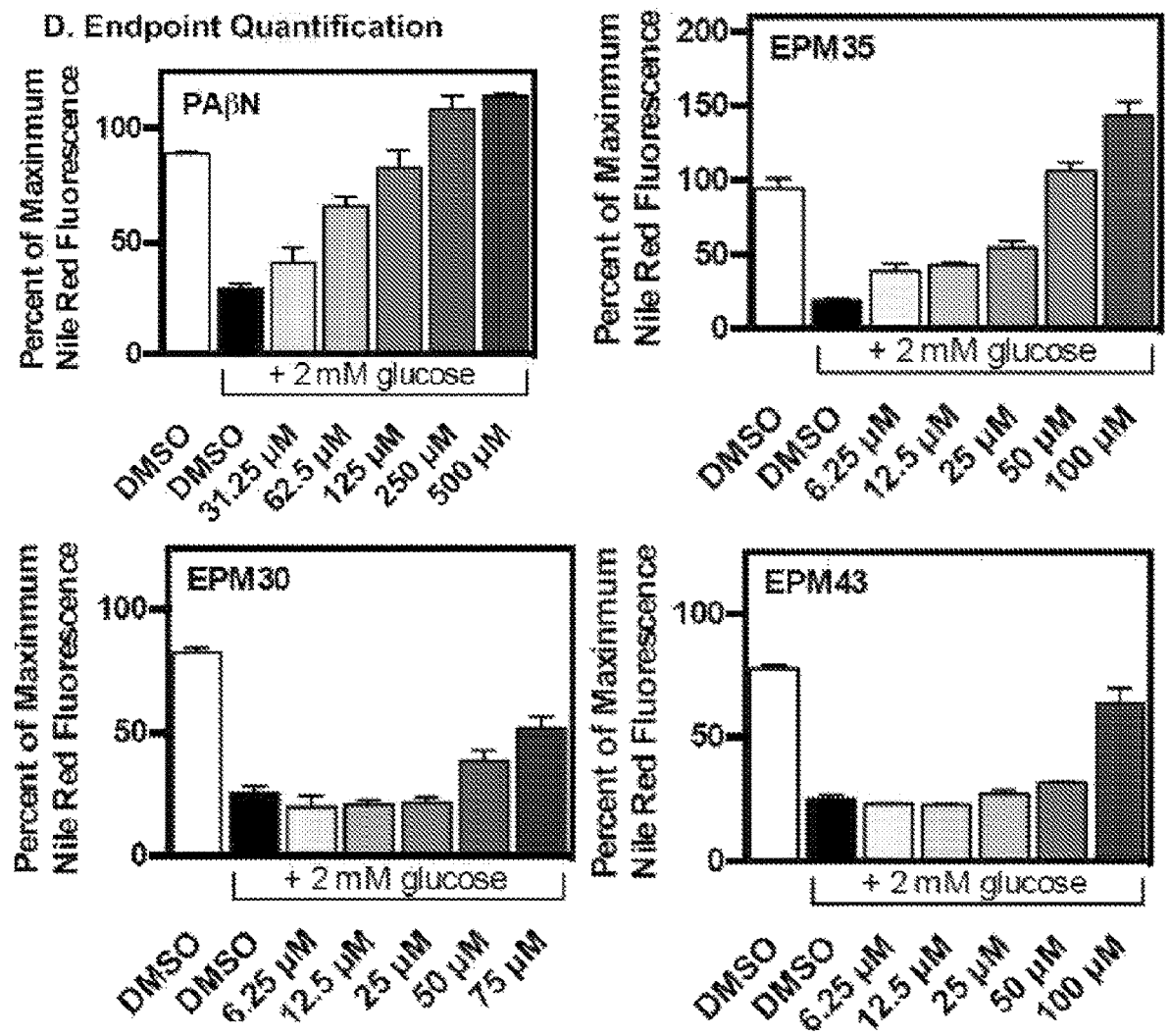
Figure 8A:
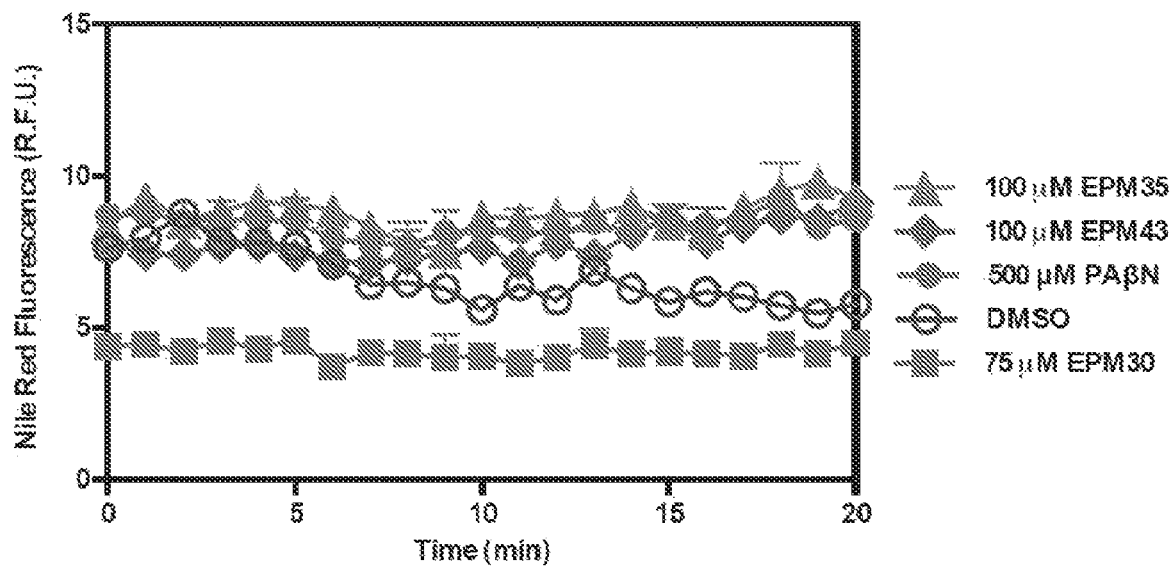
FIG. 8A depicts that Nile Red loaded bacteria were washed, combined with the indicated concentrations of compounds and fluorescence was immediately measured. Data shown are mean+SD. These data suggest that the discrepancy in starting fluorescence in FIG. 7 are due to the time between compound addition and the beginning of measurement (15-20 minutes). As indicated here, during this timeframe DMSO-treated cells efflux the dye even in the absence of glucose. Thus, EPM35, EPM43, and PAβN inhibit basal loss of Nile Red. However, treatment with EPM30 led to an immediate reduction in fluorescence.

Next, it was determined whether the EPMs inhibit glucose-activated efflux of Nile Red (FIGS. 7B, 7D). Treatment with all three EPMs inhibited Nile Red efflux in a dose-dependent manner, as observed for PAβN. At the highest concentrations tested (FIG. 7B), EPM30 (75 μM) and EPM35 (100 μM) fully inhibited efflux, but EPM43 (100 μM) only partially inhibited efflux, suggesting that EPM30 and EPM35 may be more potent. Next it was determined whether efflux pump activity is restored after removal of the compound (FIG. 7C, 7E). Washout of EPM30 partially restored efflux, similar to washout of PAβN, suggesting EPM30 may reversibly bind efflux pump components. However, cells treated with EPM35 remained unable to efflux even after removal of the drug, implying that this drug may tightly bind its target or cause degradation of its target. Cells treated with EPM43 partially effluxed Nile Red after compound washout; this efflux was similar to efflux in the presence of compound, indicating that the partial inhibition by EPM43 at this concentration was maintained even after removal of the drug. Overall, these data suggest the EPMs may employ unique modes of efflux inhibition and may target unique biochemical pathways.

Example 5. EPMs do not Appear to Disrupt the Proton Motive Force

Figure 9G:
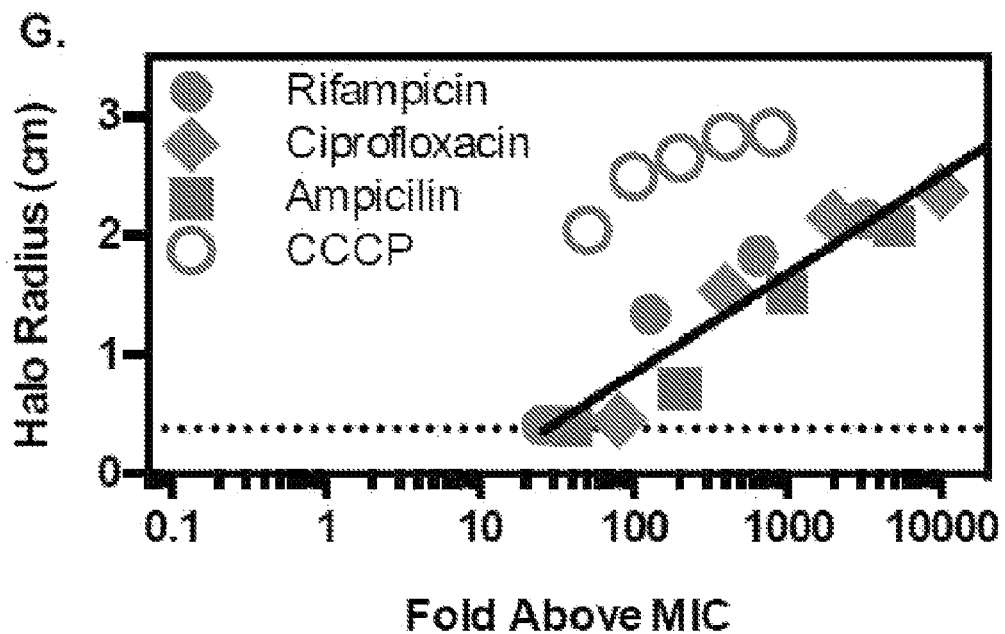
FIGS. 9G and 9H depict the distance from the center of the disk to the edge of the halo was measured using ImageJ. Dotted line is the disk radius and limit of measurable halo. Black line is the semilog fit for the combined data set of ampicillin, ciprofloxacin, and rifampicin. Data shown are the average of two measurements from each image captured, and are from a single experiment. Each compound was tested at a range of concentrations in at least two independent experiments and yielded similar trends.
Figure 9H:
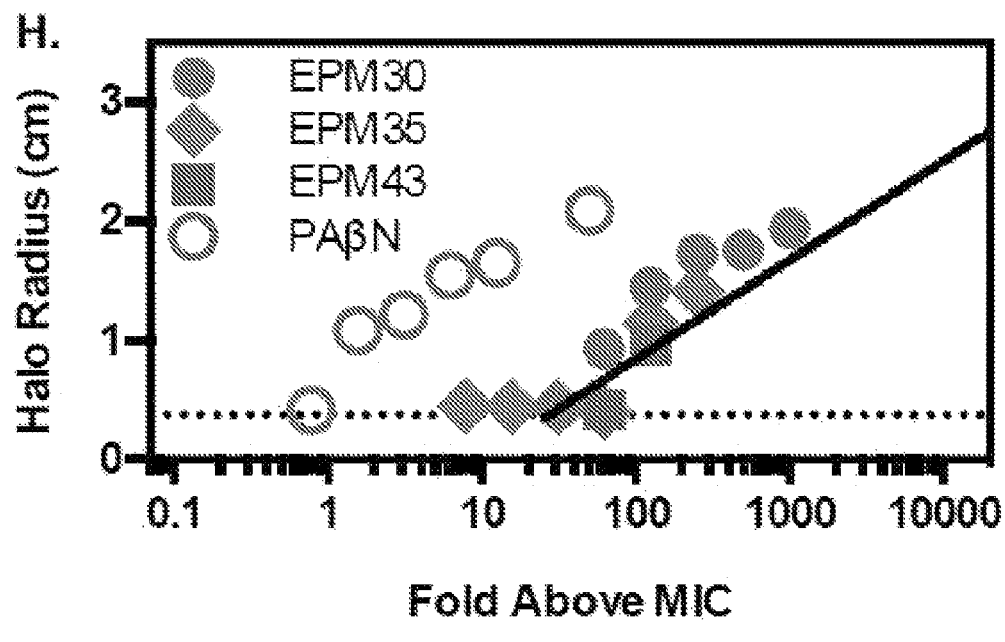

One way to inhibit efflux pumps is to disrupt the proton motive force, which is required for transport by some EPs. The EPM30, EPM35, and EPM43 compounds were tested to determine whether they alter proton motive force by monitoring the ability of S.Tm to swim in soft agar plates overnight. Bacteria were injected into the center of 0.25% agar plates, and 10 μl of compound was added to paper disks on the periphery. The bacteria avoided swimming towards the known protonophore CCCP, creating a halo around CCCP spotted at 50× the MIC (6.25 mM) (FIG. 9A). Since this assay requires an intact proton gradient and bacterial growth, bacteriostatic antibiotics not thought to disrupt the proton motive force, were tested to determine if they resulted in a halo. It was found that ciprofloxacin at 400× the MIC (4 μM) formed a halo similar in size to that of CCCP (FIG. 9B). Also ampicillin and rifampicin were tested. We plotted the halo radius versus the concentration as the fold above the MIC (FIG. 9G). All three antibiotics converged (black line), whereas a series of CCCP concentrations was shifted to the left and up. Next, it was determined whether PAβN inhibited swimming; PAβN is thought to disrupt membranes over long incubations. PAβN at only 6.25× the MIC (12.5 mM) was required to form a similar sized halo, (FIG. 9C), and PAβN, similar to CCCP, was shifted to the left (FIG. 9H), which suggests that PAβN inhibits overnight swimming by disrupting the membrane potential. These data suggest that compounds which inhibit growth inhibit swimming at higher concentrations relative to their MIC than compounds which disrupt proton motive force. Finally, the EPMs at 50 mM were tested (FIGS. 9D-F). EPM30 formed a halo. The concentration tested is 500× the MIC, so it was concluded that EPM30 likely prevented swimming by inhibiting growth, similar to ciprofloxacin. EPM35 formed a small halo; the concentration tested is 125× the MIC. EPM43 formed no halo, even though the concentration is ~62.5× the MIC. That EPMs only form halos at concentrations much higher than their MICs (or we are limited by solubility) suggests that the haloes formed by the EPMs are due to growth inhibition.

Example 6. The Three EPMs are Potent and Structurally Diverse

Next, the structural and drug-like properties of the three EPMs with PAβN were compared (FIG. 6). All three compounds showed greater than 97% inhibition of S.Tm in macrophages in the initial SAFIRE screen, single-digit micromolar IC50s, and reduction of at least 98% of bacteria in CFU plating assays (FIG. 2B, FIG. 6). The compounds also had low activity against S.Tm grown in broth, which is consistent with their activity as EPMs. As described above, the EPMs demonstrated lower EC50s in the Hoechst assay compared to PAβN. Next, the in vitro toxicity of the EPMs was investigated using the LDH assay in the human hepatocyte cell line HepG2, which predicts toxicity and metabolism of drugs by the liver. All three compounds displayed moderate toxicity in HepG2 LDH assays, although higher than the IC50s against intracellular S.Tm in RAWs, suggesting the presence of a therapeutic window below host toxicity. Further, optimization of the structure by medicinal chemistry may yield less toxic molecules. Log D describes the lipophilicity of a compound, and corresponds with its ability to permeate biological membranes; typically a log D below 3 is desirable for a drug. Together, log D and solubility indicate a compound's likely bioavailability, which impacts the utility as a therapeutic. All three EPMs have log D around 3 and poor solubility, leading to low predicted bioavailability; optimization of the chemical structures may lead to compounds that have potential as a biological probe or drug.

All three EPMs are structurally distinct from each other and from EPM PAβN, which is a naphthyl peptidomimetic (FIG. 6). EPM30 is a small compound with an aminothiazole core, which is amenable to synthetic modification. Several aminothiazole compounds have been identified that inhibit efflux, although EPM30 is smaller than these molecules. Aminothiazoles often have adequate cellular permeability to be active against intracellular microbes. The next EPM identified was EPM35, a trifluoro-pyrimidine linked to a piperidine. Excitingly, a very similar compound was identified by an in silico screen of the Maybridge library for binding to AcrB, the active component of a key efflux pump in S.Tm. The EPM35-similar compound occupies the substrate-binding pocket of AcrB, and likely spans a large portion of the pocket, as do other inhibitors that target AcrB. Finally, the third compound, EPM43, is a small quinazoline, a planar moiety which is a common drug pharmacophore.

Other quinazolines have been identified as inhibitors of bacterial and fungal EPs. Interestingly, EPM43 itself has previously been identified as an inhibitor of fungal dihydrofolate reductase (DHFR) though not the human enzyme. It is possible that this compound inhibits bacterial DHFR. If so, it seems likely that this activity might be independent of efflux inhibition, because there is no known connection between DHFR and bacterial efflux. EPM43 is less toxic to HepG2 cells than the other EPMs, but demonstrates poor aqueous solubility. Overall, the three EPMs represent three unique scaffolds amenable to medicinal chemistry.

Example 7. EPMs Sensitize S.Tm to Host Antimicrobial Peptides

Figure 10:
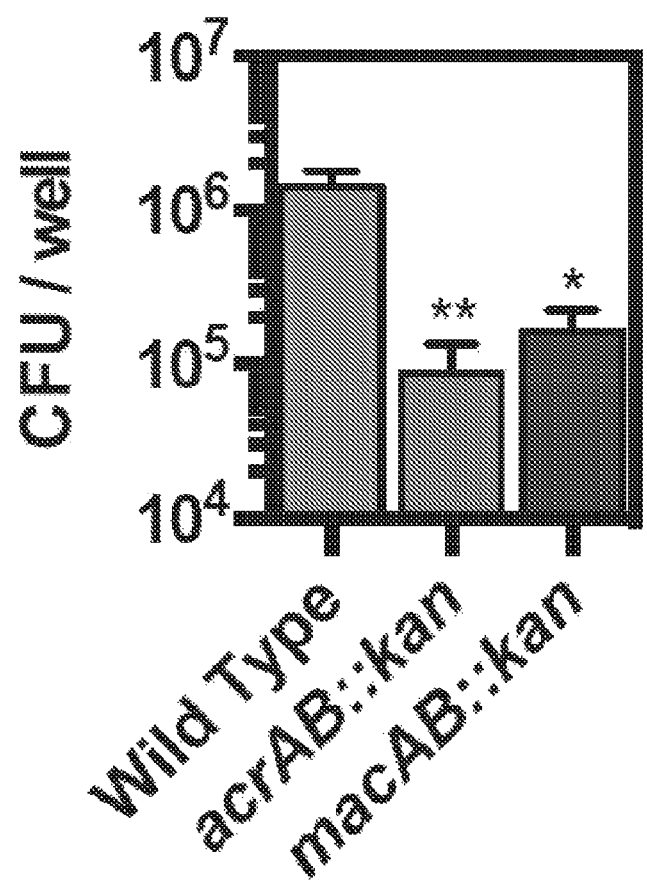
FIG. 10 depicts that efflux pumps are required for infection of RAW 264.7. Macrophages were infected with the indicated strains. At 18 hours post-infection, cells were lysed and plated to enumerate CFUs. Data shown are mean+SEM of 3 independent biological replicates.
Figure 11:
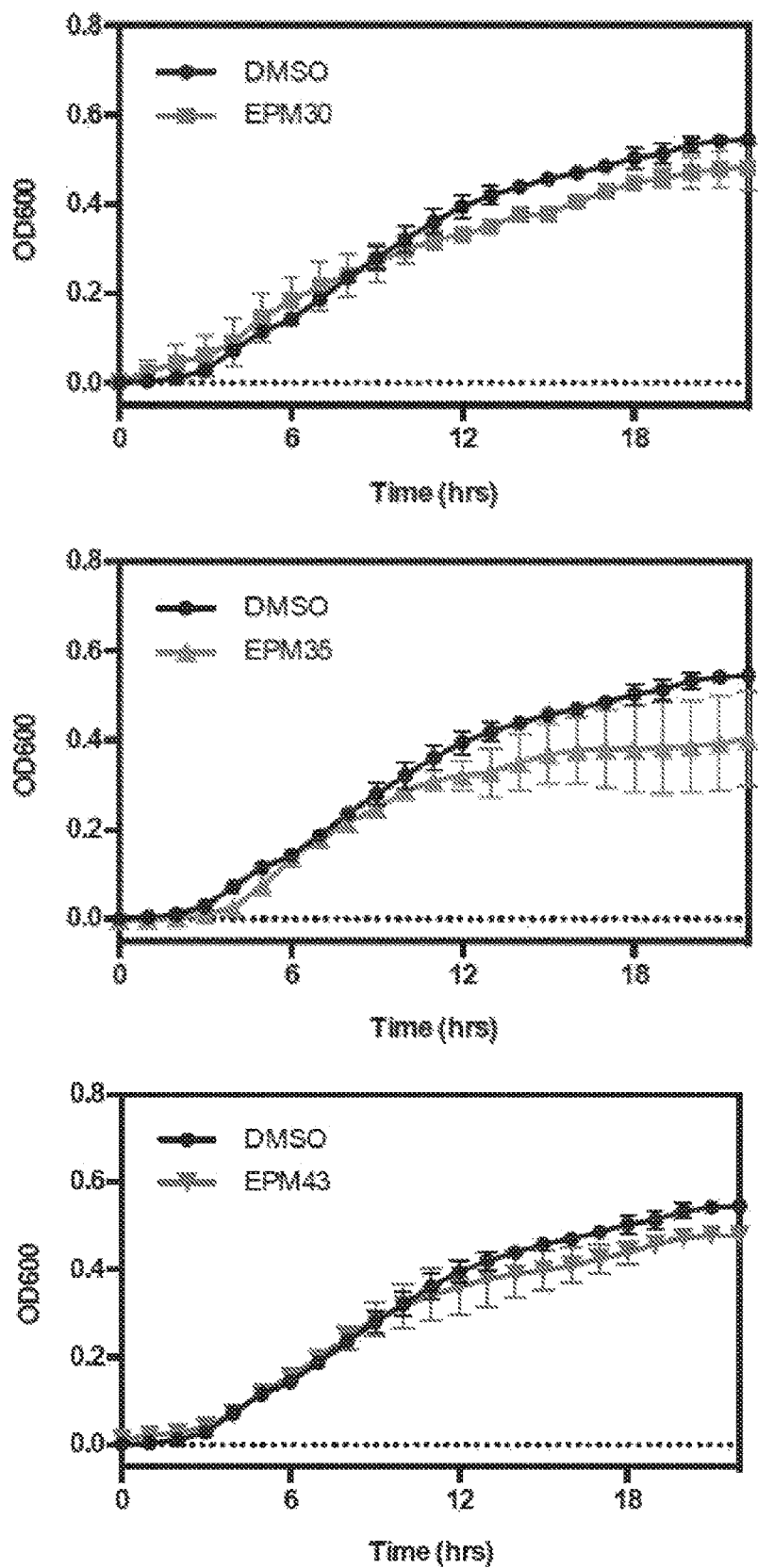
FIG. 11 depicts that EPMs do not potentiate ROS in broth. Wild-type S.Tm were grown in the presence of 0.2 mM $H_2O_2$ and 25 μM of the indicated EPMs. Data shown are mean+SEM from two independent biological replicates. DMSO curve is repeated across graphs.
Figure 12A:
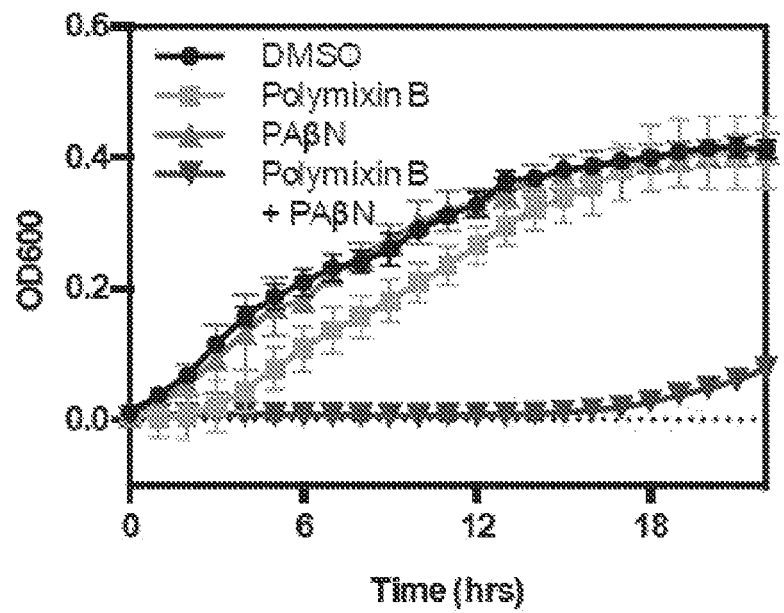
FIGS. 12A-12H depict that EPMs synergize with antimicrobial peptides. Wild-type S.Tm were grown in the presence of the antimicrobial peptides polymyxin B (5 μg/ml; ⅛ MIC) or LL37 (5 μg/ml; ⅛ MIC) and EPMs (DET30, DET35, DET43: 25 μM; PAβN: 500 μM). Growth medium for each antimicrobial peptide is described in the methods. Data shown are mean+SD of triplicate samples from one representative experiment of 3 independent biological replicates. DMSO, polymyxin B, and LL37 curves are repeated across graphs.
Figure 12B:
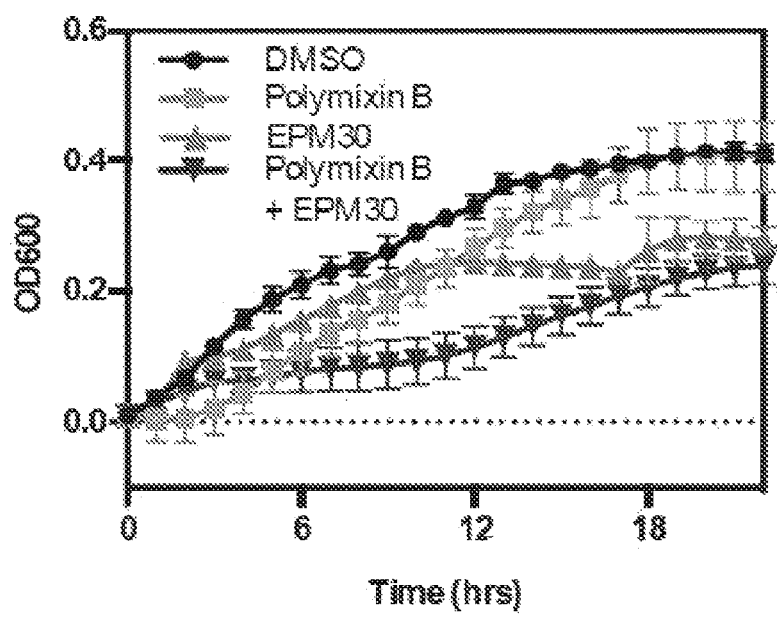
Figure 12C:
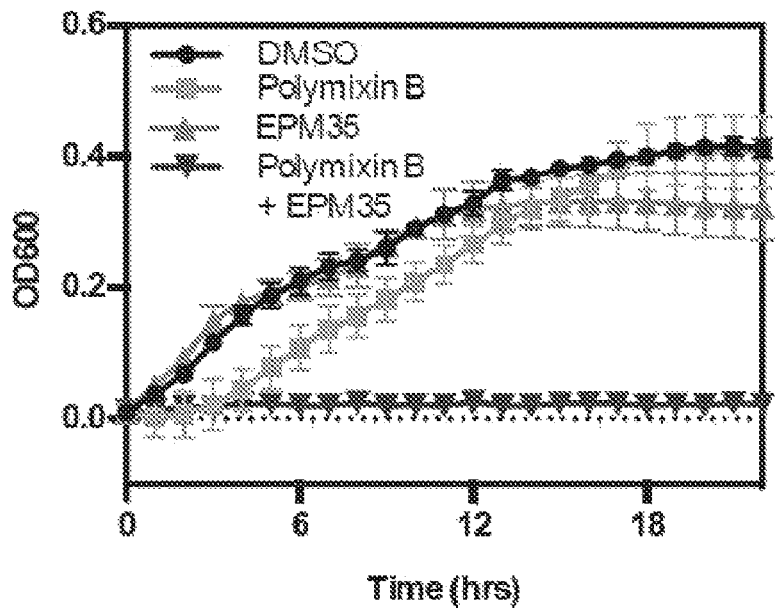
Figure 12D:
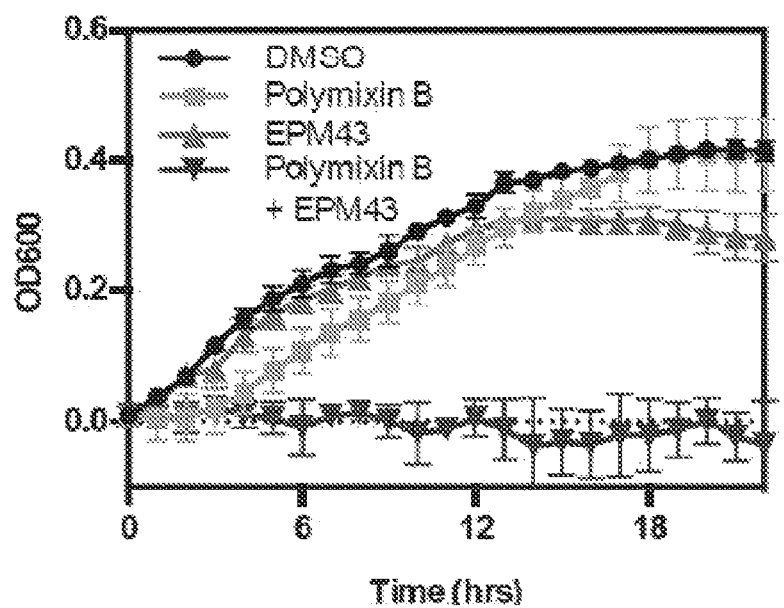
Figure 12E:
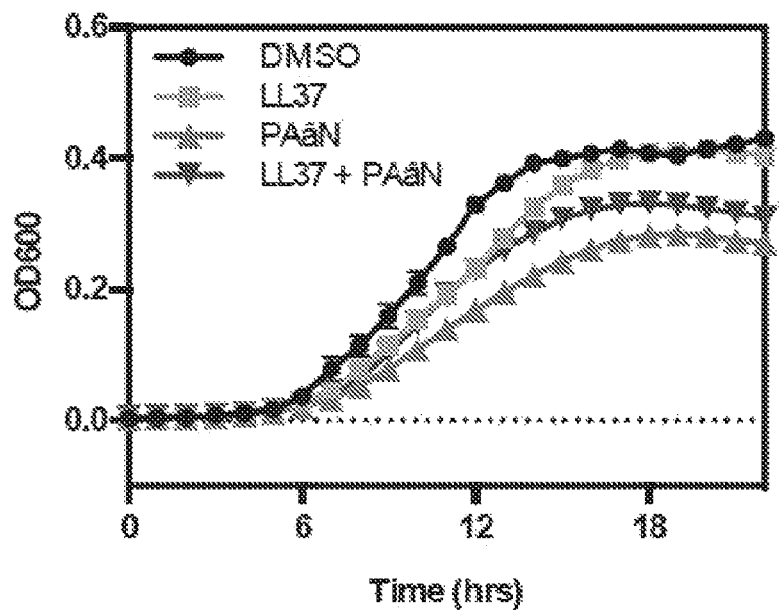
Figure 12F:
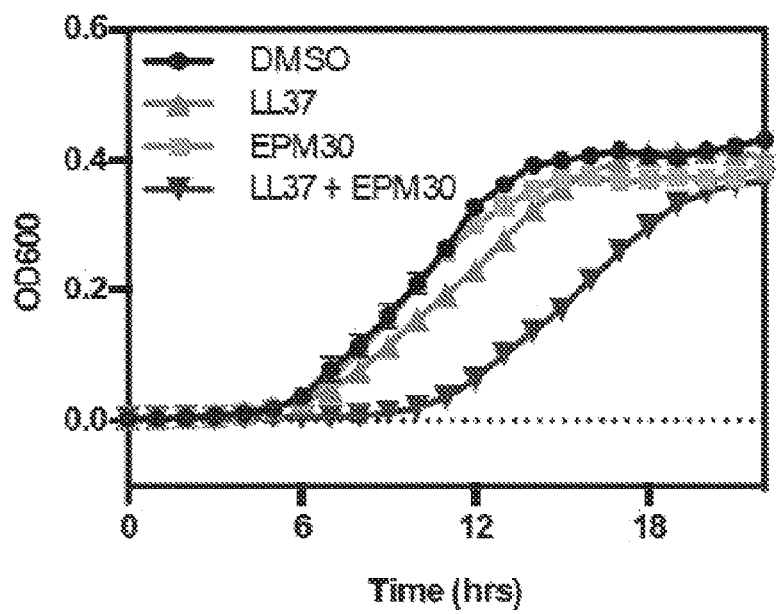
Figure 12G:
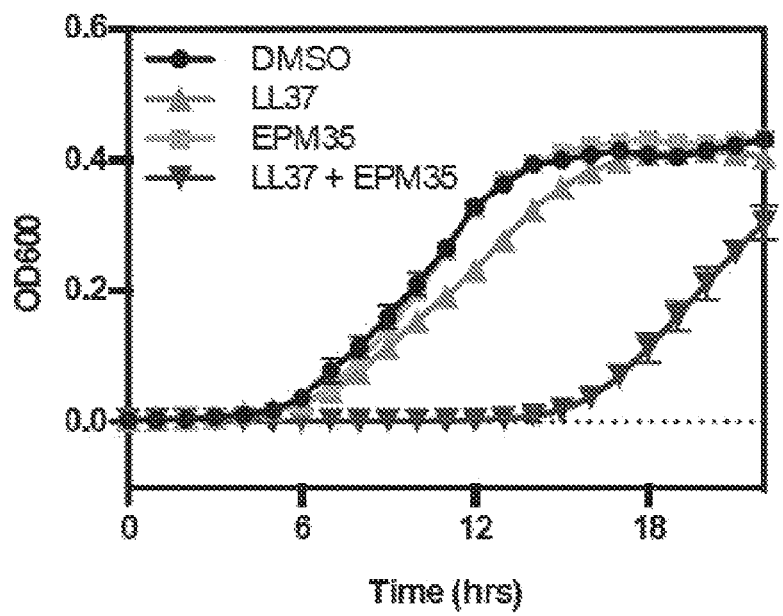
Figure 12H:
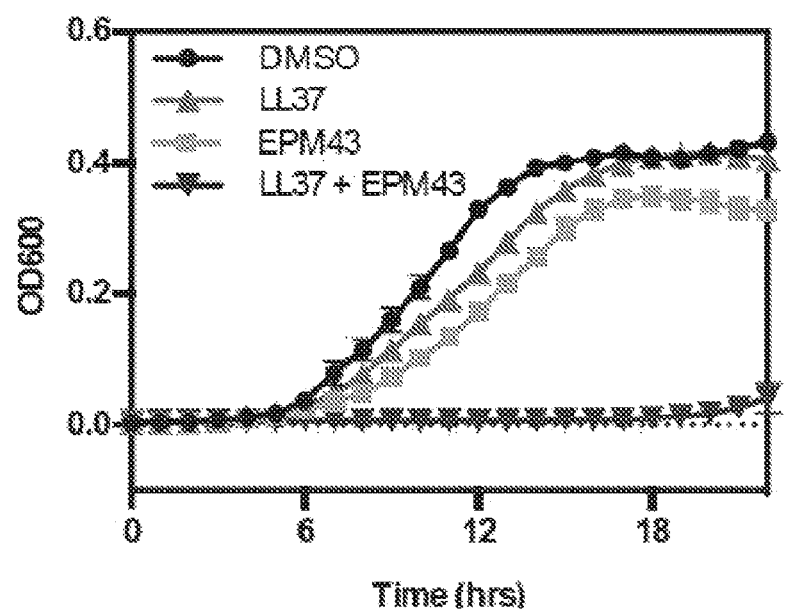

Next, it was investigated how EPMs might lead to bacterial clearance within host cells. Because efflux pumps are not essential for S.Tm growth in broth and the three EPMs exhibited high MICs, it was unlikely that EPMs independently cause bacterial death. Instead, EPMs may synergize with a host antimicrobial(s) that is effluxed by EPs. Two S.Tm EPs are necessary for infection of macrophages and mice (FIG. 10). The first EP, MacAB, is important for defense against ROS. The second S.Tm EP, AcrAB, is a homolog of MtrCDE, an EP in *Neisseria gonorrhoeae* which exports host antimicrobial peptides (AMPs). AcrAB thus likely exports AMPs as well as a variety of other substrates including antibiotics, dyes, and detergents. To test whether the EPMs synergize with macrophage defenses, wild-type bacteria was exposed in broth to ROS or AMPs in the presence of EPMs. The EPMs had no effect on bacterial growth in 0.2 mM $H_2O_2$, suggesting they do not synergize with ROS (FIG. 11). Next, the two AMPs were tested: polymyxin B is a model peptide produced by bacteria; LL-37 is a human cathelicidin produced by macrophages. Bacteria treated with 5 µg/ml AMP (⅛ MIC) or 25 µM EPM exhibited mild to no growth inhibition. However, combination treatment significantly inhibited growth; similar results were obtained with 500 µM PAβN (FIG. 12). Interestingly, co-treatment with EPMs and the human AMP LL-37 caused varying levels of growth inhibition, suggesting that polymyxin B and LL-37 may employ different mechanisms of action. However, co-treatment with polymyxin B and either EPM35 or EPM43 completely inhibited growth, indicating that the EPMs can synergize with AMPs.

Figure 13A:
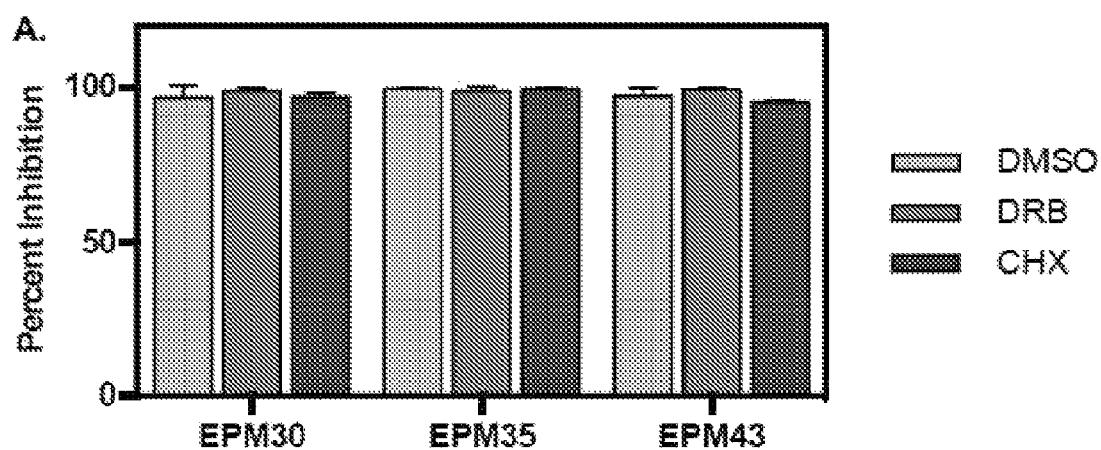
FIG. 13A depicts that RAWs were infected and treated with 25 μM of the indicated compounds using SAFIRE. From 2-18 hours post-infection, cells were treated with DMSO, 100 μM DRB, or 1 μM cycloheximide (CHX). Data for each inhibitor (DRB, CHX) treatment are normalized to cells not treated with EPMs, as differences in basal infection were observed (FIG. 10). Data are mean+SEM of three independent biological replicates, each performed in triplicate.
Figure 13B:
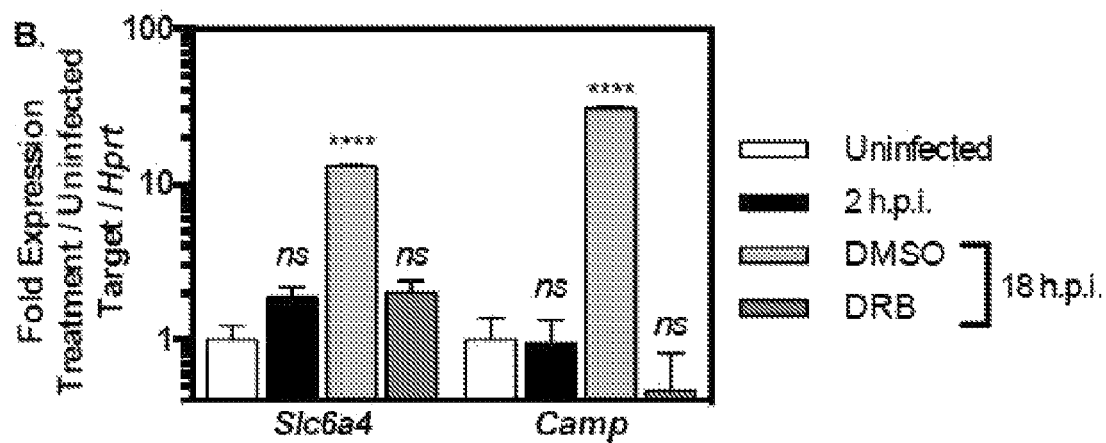
FIG. 13B depicts that RAWs were seeded in 6-well dishes and treated in parallel with FIG. 13A. RNA was extracted at the indicated timepoints, reverse transcribed, and expression of the indicated genes was determined using qPCR. Data shown are mean+SEM of four separate wells from one replicate, and were performed in parallel with one replicate of (A). ****$p<0.0001$ compared to uninfected by two-way ANOVA with Dunnett's post-test.

Although AMPs such as LL-37 and β-defensin 2 are upregulated in response to infection, AMPs such as LL-37, α-defensin, β-defensin 1, and angiogenin are also basally expressed and stored in azurophilic granules. Therefore, the question was whether the EPMs require host transcription or translation of AMPs or other factors, for antimicrobial activity. SAFIRE was performed in the presence of a transcriptional (DRB) or translational (cycloheximide) inhibitor (FIG. 13). Since exposure to inhibitors prior to infection greatly diminished macrophage viability, DRB or cycloheximide was added 2 hours post-infection, concurrently with EPMs. This procedure should prevent late induction of host defense genes, and, indeed, there was no observance of increased macrophage expression of Slc6A4 (5-HTT) and Camp, two genes induced in macrophages late (FIG. 13B). While treatment with DRB or cyclohexamide decreased basal infection (FIG. 14), antibacterial activity of the EPMs did not change (FIG. 13A). These data suggest that macrophage defenses induced more than 2 hours after infection do not contribute to EPM antibacterial activity. Instead, one or more of the many host defenses that are induced early 110] may synergize with EPMs.

Figure 15A:
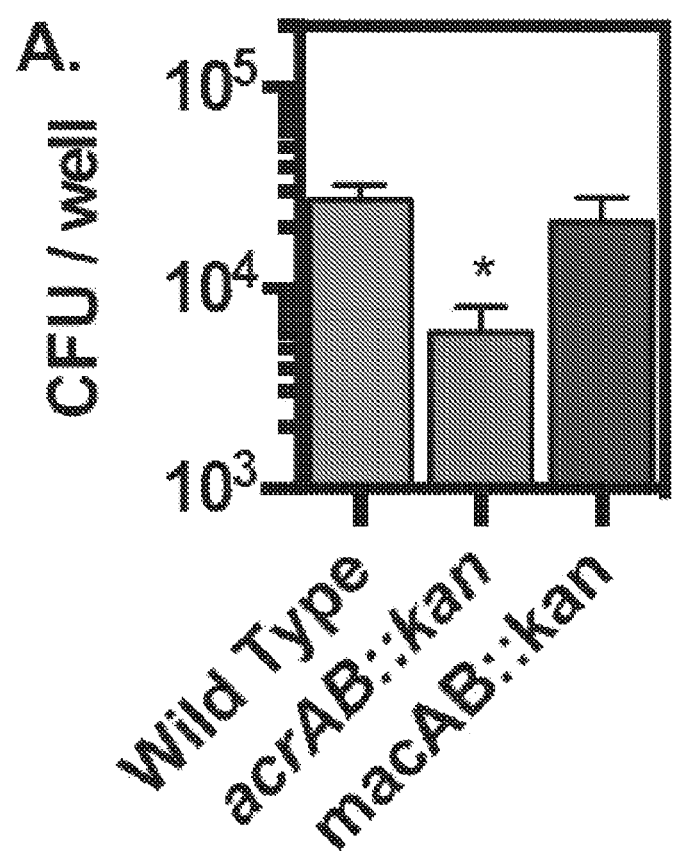
FIG. 15A depicts that HeLa cells were infected with the indicated strains; at 18 hours post-infection cells were lysed and plated to enumerate CFUs.
Figure 15B:
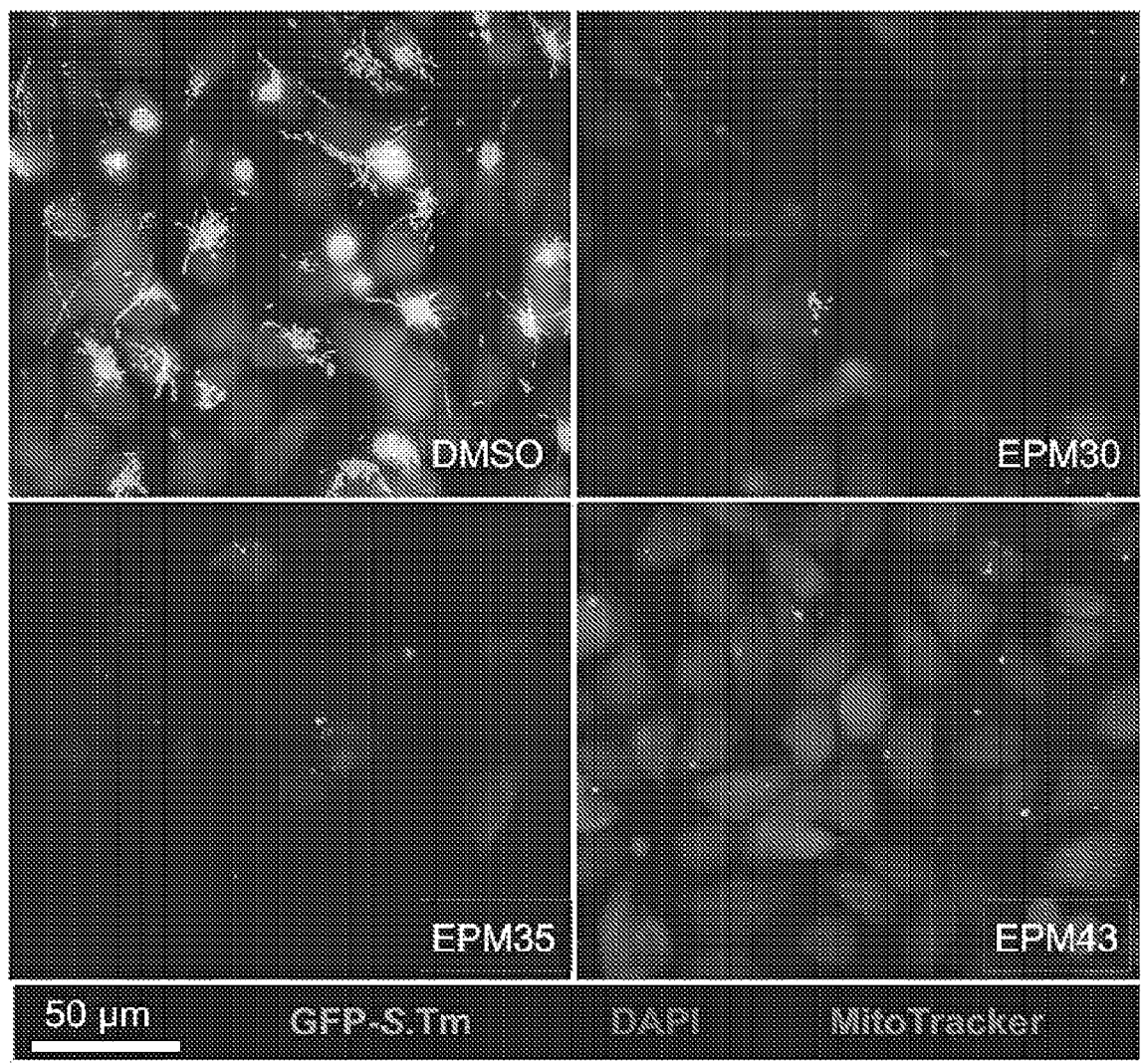
FIGS. 15B and 15C depict that HeLa cells were infected with rpsM::GFP S.Tm and treated with 25 μM compound for 16 hours according to the SAFIRE protocol.
Figure 15C:
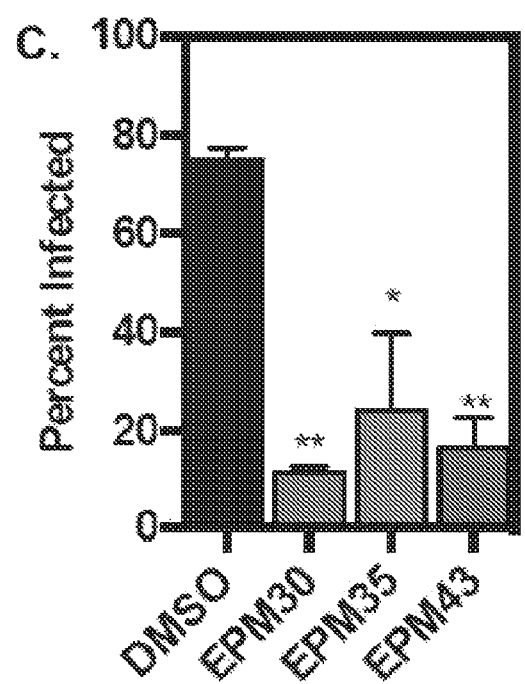

Next, whether EPMs may inhibit S.Tm growth in non-immune cells was analyzed. AMPs are expressed by multiple cell types, including diverse epithelial cells. Thus, whether EPMs inhibit S.Tm growth in HeLa cells was tested. HeLa cells express AMPs and are a model of epithelial cell infection. First, Eps were tested to determine if they are relevant for infection of HeLa cells. Deletion of acrAB but not macAB reduced bacterial colonization (FIG. 15A). Next HeLa cells were infected with S.Tm expressing GFP from the rpsM locus and monitored for bacterial infection with SAFIRE after treatment with the three EPMs (FIG. 15B, 15C). Treatment with EPM30 and EPM35 appeared to decrease MitoTracker signal in HeLa cells, which agrees with the results from the LDH assay (FIG. 9) and macrophage screening (FIG. 2B). However, all three EPMs decreased bacterial load in HeLa cells at 25 µM. EPM treatment of infected HeLa cells did not lead to complete absence of bacteria as observed during treatment of infected RAWs (FIG. 2B). Instead, we observed isolated intact bacteria. This may suggest that HeLa cells do not degrade dead bacteria as quickly as macrophages, or that EPMs primarily arrest bacterial growth in HeLas, or this effect may be due to differences in GFP expression by S.Tm. Overall, these data indicate the EPMs may be active against infections of diverse cell types, including non-immune cells.

Figure 16A:
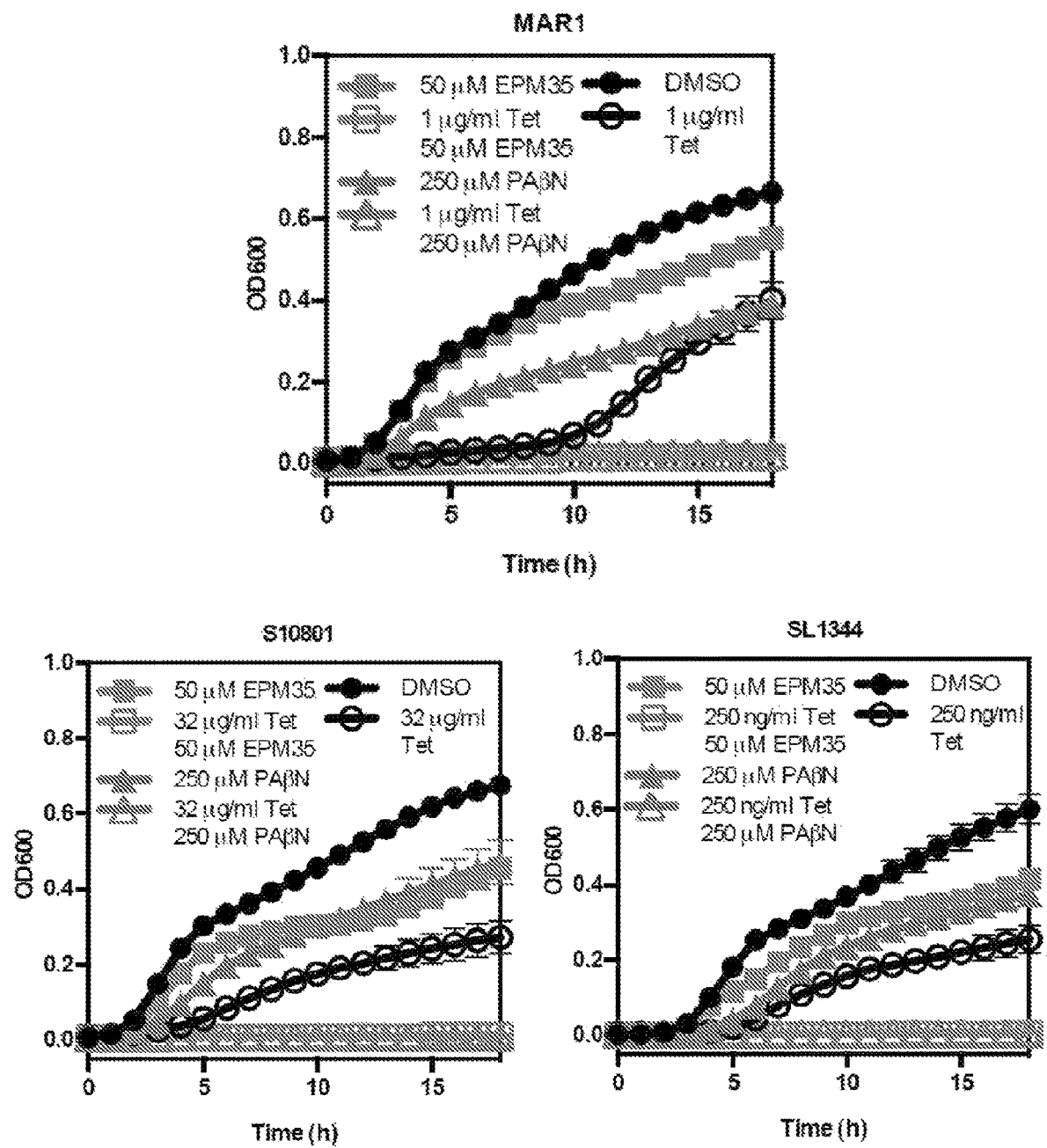
FIG. 16A depicts that bacteria were grown in MHB broth supplemented with the indicated concentrations of tetracycline, EPM35, or PAβN. MAR1 is derived from SL1344.

Example 8. EPM35 Increases Sensitivity of Multi-Drug Resistant S.Tm to Tetracycline Increased expression or function of efflux pumps often contributes to clinical multidrug resistance. Therefore, whether the EPMs re-sensitize two multidrug resistant strains of S.Tm to tetracycline was tested. Tetracycline is an antibiotic exported by AcrAB. The MAR1 strain is derived from wild-type SL1344 was selected by exposure to tetracycline, and has increased expression of the AcrAB efflux pump. S10801 is an MDR strain isolated from the mesenteric lymph node of a septic calf and is resistant to tetracycline, ampicillin, chloramphenicol, nalidixic acid, and triple sulfa. The basis of multi-drug resistance in this strain is unknown. MAR1 has a 2-fold increase in MIC (4 µg/ml) over isogenic wild-type S.Tm (2 µg/ml). S10801 has a 64-fold increase in tetracycline MIC (128 µg/ml) over wild type. It was found that EPM35 increased sensitivity to tetracycline, but not EPM30 or EPM43, suggesting these compounds have an alternative target. Treatment of both strains with 250 µM PAβN (⅛ MIC) or 50 µM EPM35 (⅛ MIC) decreased the tetracycline MIC 4-fold (FIG. 16A). In addition, the effect of these concentrations on the sensitivity of wild type S.Tm was tested, which showed similar reductions in MIC as with the MDR strains (FIG. 16A). To expand these results, checkerboard assays were performed with all three strains (FIG. 16B), which showed comparable reductions in MIC for different combinations of tetracycline and EPM35 or PAβN. The Fractional Inhibitory Concentration Index (FICI) was calculated for each pair and identified combinations where the FICI was below 0.5, suggesting synergistic interactions between tetracycline and the EPMs.

Figure 16C:
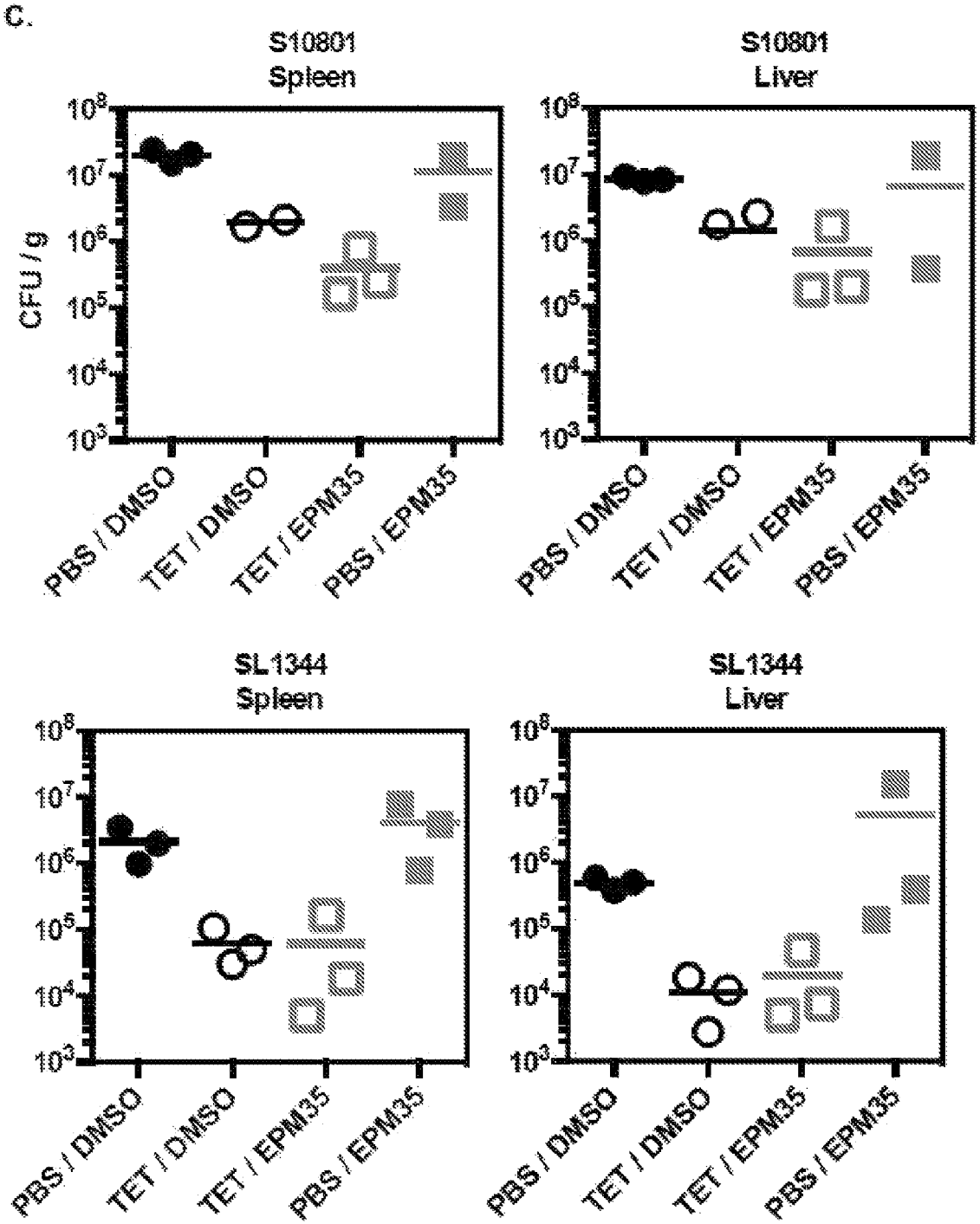
FIG. 16C depicts that C57/B16 mice were infected with 104 S.Tm intraperitoneally. At 30 minutes and 24 hours post-infection, mice received 25 mg/kg tetracycline, 50 mg/kg EPM35, or the combination. Six hours after the second injection, tissues were harvested and plated to enumerate CFUs.

Finally, whether EPM35 increased sensitivity of 510801 and wild-type S.Tm to tetracycline in vivo was tested. 7-week-old C57BL/6 mice were intraperitoneally infected with $1 \times 10^4$ bacteria. At 30 minutes and 24 hours post-infection, 25 mg/kg tetracycline and 50 mg/kg EPM35 was injected. Distress was observed in mice treated with EPM35 including squinty eyes and hunching posture, as well as neurological abnormalities in one mouse (loss of coordination, tail stiffening). Thus, the experiment was ended at 30 hours post-infection; the spleen and liver were harvested and plated to determine bacterial CFU. S10801-infected mice injected with tetracycline alone had lower levels of bacteria, but co-treatment with EPM35 appeared to further reduce bacterial CFU (FIG. 16C). This enhanced decrease was not observed in mice infected with wild-type bacteria, suggesting this combinatorial effect may be specific against MDR bacteria. Due to the signs of distress observed in mice treated with EPM35, the experiment was not repeated.

Figure 17A:
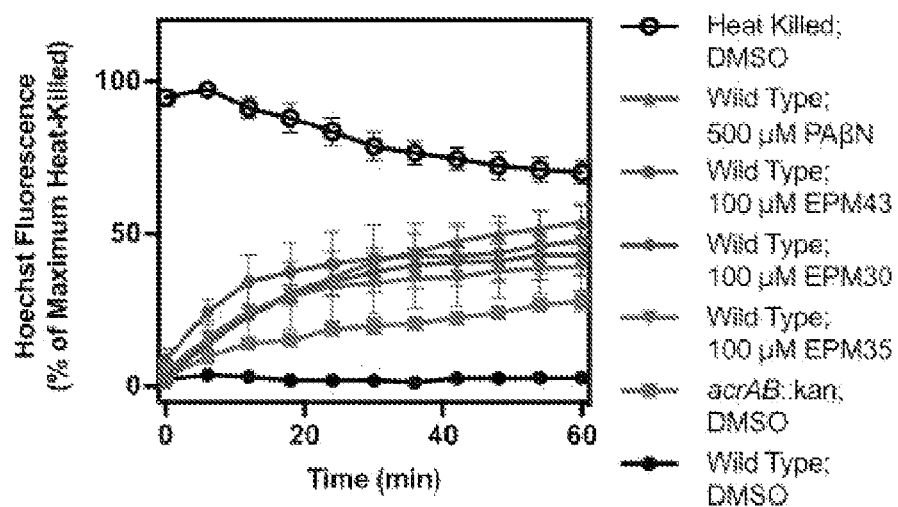
FIG. 17A depicts Salmonella incubated with Hoechst 33342 and the indicated compound. Fluorescence was normalized to the maximum of heat-killed bacteria (100%). Mean and SEM from three biological replicates shown.
Figure 17B:
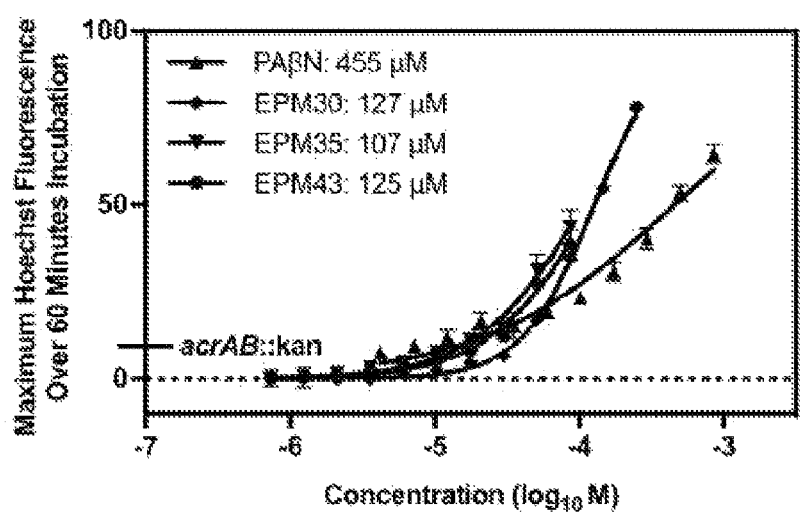
FIG. 17B depicts maximum fluorescence over 60 minutes of exposure normalized to the maximum fluorescence of heat-killed bacteria (100%). EC50s in legend were established using a nonlinear fourparameter fit. Mean and SEM from three biological replicates, each performed in duplicate.

Example 9. Three Compounds Increase *Salmonella* Accumulation of an Efflux Pump Substrate SAFIRE has the potential to identify EPMs because *Salmonella* requires at least two efflux pumps, AcrAB and MacAB, to replicate and/or survive within macrophages and mice. The fluorescent dye Hoechst 33342 is an efflux pump substrate, and increased Hoechst accumulation relative to controls identifies potential modulators of efflux pumps. Bacteria was incubated with each of the 58 repurchased, validated hits and Hoechst 33342. As expected, heat-killed bacteria exhibited high fluorescence immediately after exposure to Hoechst because an electrochemical gradient is required to export pump substrates. Live, wild-type *Salmonella* demonstrated low fluorescence, and a strain lacking the AcrAB efflux pump had a modest level of fluorescence. PaβN treatment resulted in higher levels of fluorescence. Under the same conditions, treatment with three of the 58 compounds (EPM30, EPM35 and EPM43) resulted in fluorescence comparable to that of PAβN (FIG. 17A). Further examination revealed that the three compounds had effective concentration-50s (EC50s) four-fold lower than that of PAβN in the Hoechst assay (FIG. 17B). The chemical structures of the three compounds do not resemble known efflux pump inhibitors (FIG. 17C). Finally, since the cell culture assays use gentamicin to prevent the replication of extracellular *Salmonella*, it was established that the three compounds do not synergize with the antibacterial activity of gentamicin in broth (FIG. 4). Altogether, the data suggested that the putative EPMs merit further study.

Figure 18A:
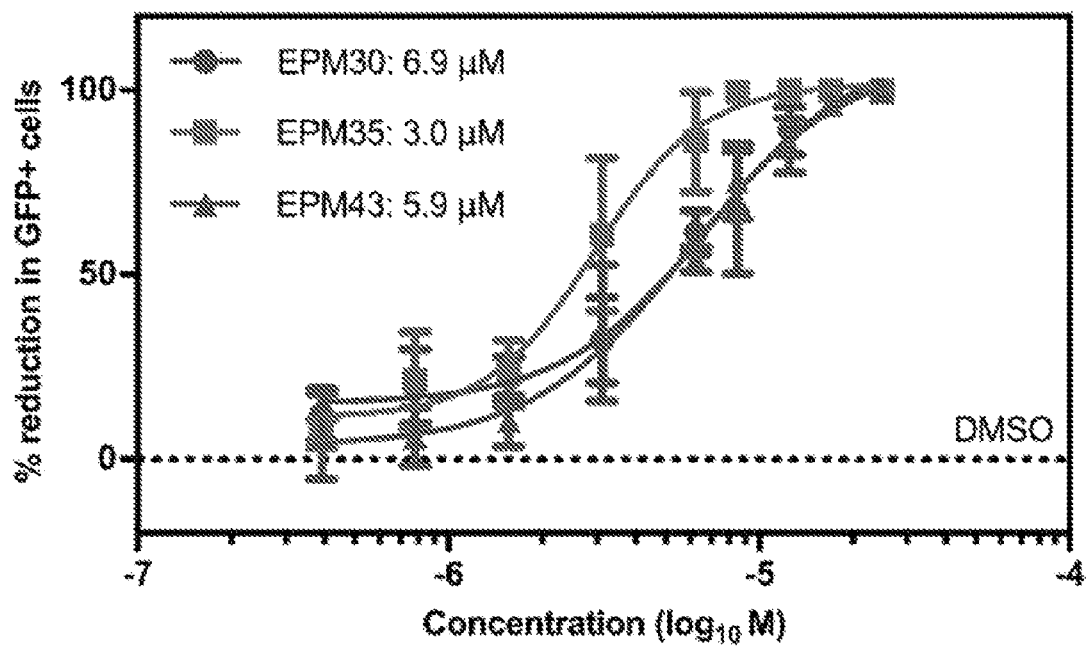
FIG. 18 depicts that three EPMs decrease bacterial load of *Salmonella* in mammalian cells. As detailed herein, two hours after infection cells were treated with the indicated compound [25 µM] for 16 hours. Percent reduction in GFP positive cells compared to DMSO treatment in (FIG. 18A) RAW 264.7 macrophages exposed to a range of EPM concentrations (key includes IC50 values) or in (FIG. 18B) HeLa cells treated with 25 µM of each EPM. Mean and SEM from three independent biological replicates. *p<0.05; **p<0.01 compared to DMSO by one-way ANOVA with Dunnett's post-test.
FIGS. 18C-F depict monitoring of bacterial load by CFU.
Figure 18B:
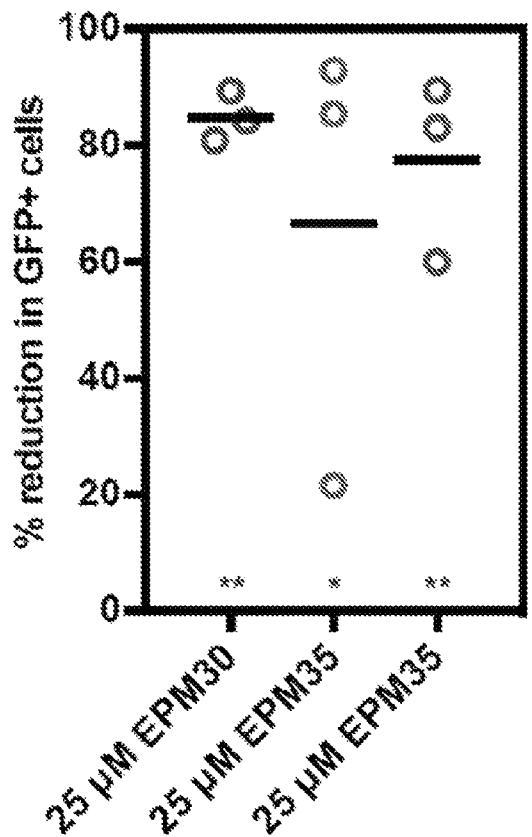
Figure 18C:
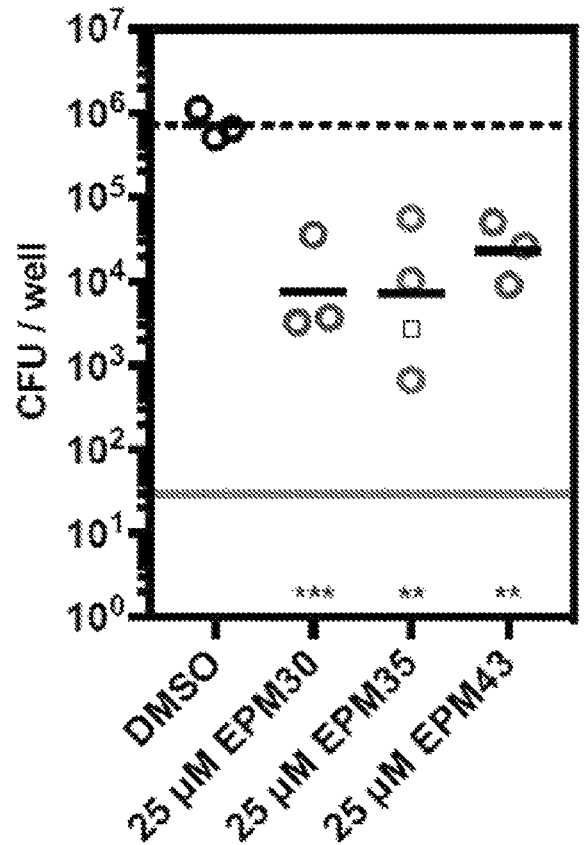

Example 10. Three Hit Compounds are Antibacterial Against *Salmonella* in Macrophages and Epithelial Cells A more thorough characterization was performed of the putative EPMs regarding anti *Salmonella* activity in multiple mammalian cell types. Micrographs from RAW264.7 macrophages treated with 25 μM of each compound demonstrated a significant reduction in bacterial GFP signal compared to treatment with vehicle alone (FIG. 5A). The inhibitory concentration-50 (IC50) for the three compounds in macrophages ranged from 3 to 7 μM (FIG. 18A). HeLa cells harboring a *Salmonella*-165 GFP reporter strain and treated with 25 μM of each compound also demonstrated a reduction in bacterial GFP signal compared to treatment with vehicle alone (FIGS. 5C, 18B). To establish whether reduced GFP signal correlates with bacterial killing, we quantified bacterial survival by enumerating CFU from infected cells. RAW264.7 macrophages treated with the putative EPMs reduced the number of recoverable *Salmonella* 100-1,000-fold, compared to treatment with vehicle or PAβN (FIG. 18D). In primary bone marrow-derived mouse macrophages (BMDMs) all three hit compounds reduced the number of recoverable *Salmonella* (SL1344) by approximately 20-fold (FIG. 18C). Thus, the putative EPMs inhibit bacterial replication and/or survival in multiple cell types relevant to whole animal infection.

Example 11. The Putative EPMs Reduce the Survival of MDR *Salmonella* in Macrophages Clinical MDR isolates frequently express high levels of efflux pumps (1). *Salmonella* encode at least two efflux pumps needed for bacterial survival in cells, AcrAB and MacAB. Both of these pumps use the TolC channel to transport cargo across the outer membrane. The importance of the acrAB, macAB and to/C genes for bacterial replication and/or survival was confirmed in macrophages (FIG. 18D). A laboratory isolate of *Salmonella* (SL1344), MAR1, was selected for resistance to tetracycline and is also resistant to other antibiotics based on a mutation that increases expression of the AcrAB efflux pump (27). Treatment of macrophages with any of the three putative EPMs [25 μM] was found to not significantly reduce the load of the MAR1 strain compared to treatment with DMSO (FIG. 18E). However, a clinical MDR *Salmonella* isolate (S10801) was recovered from macrophages at levels at 188 least 100-fold lower upon EPM treatment compared to DMSO or PAβN (FIG. 18F), indicating that the hit compounds inhibit MDR bacteria during infection.

Example 12. The Hit Compounds Inhibit Energy-Dependent Efflux Pump Activity

Figure 8B:
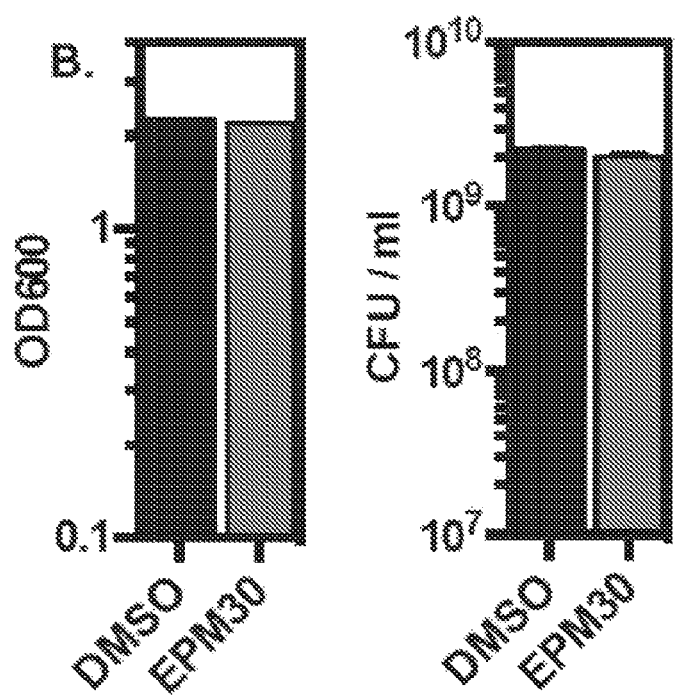
FIG. 8B depicts that bacteria remain intact and viable after 20 minutes incubation in 75 μM EPM30. The immediate reduction in fluorescence in FIG. 8A is not due to immediate death of the bacteria. It is possible that EPM30 reduces Nile Red fluorescence by quenching or by altering membrane properties, as Nile Red's fluorescent properties are highly dependent on membrane polarity, content, and dynamics.
Figure 19A:
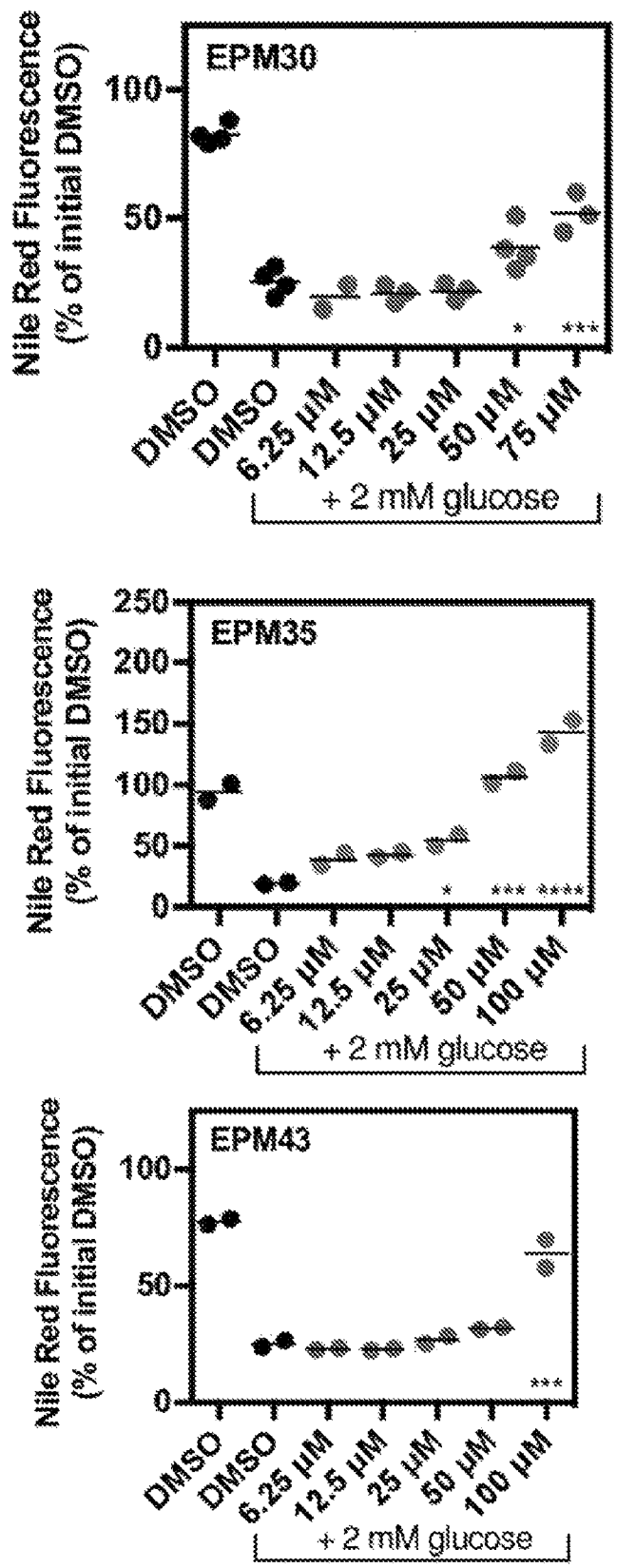
FIG. 19A depicts Nile Red dose response curve seven minutes after glucose addition. Data were normalized to the initial fluorescence for DMSO-treated cells without glucose (100%).
Figure 19B:
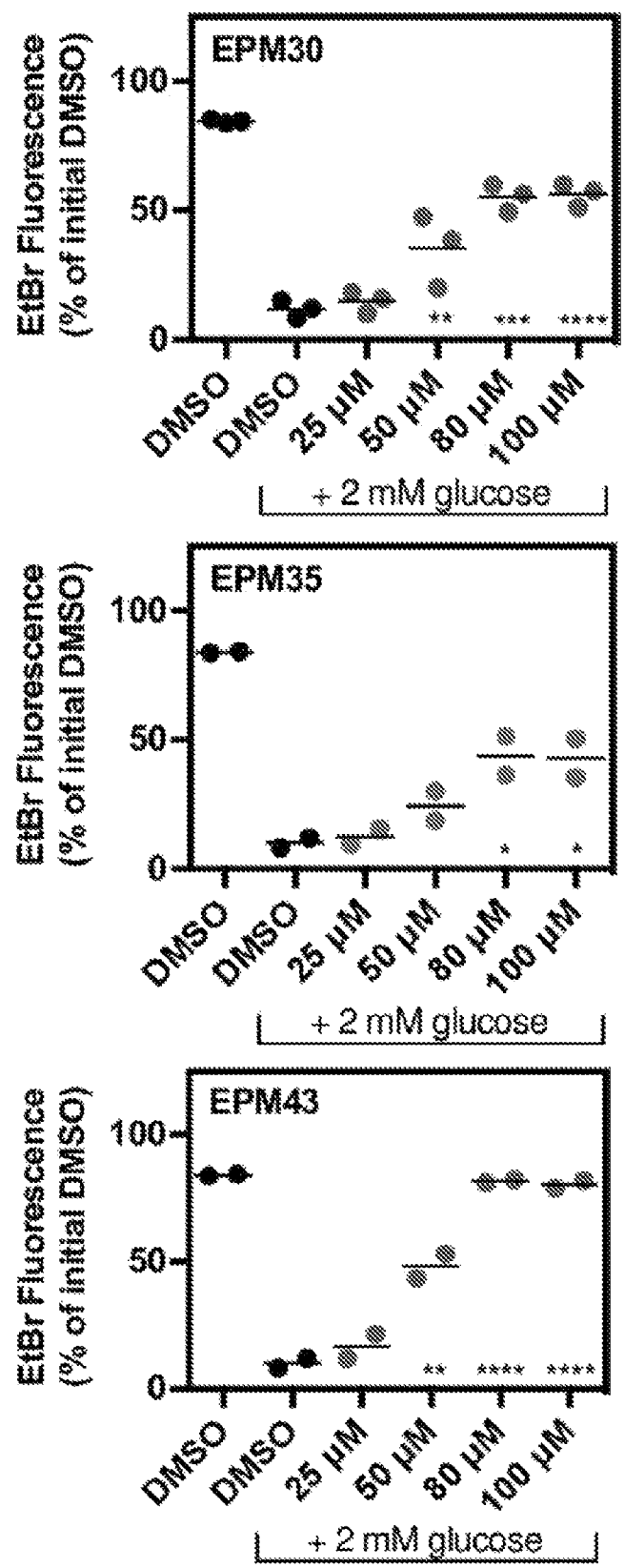
FIG. 19B depicts ethidium bromide normalized dose response curve data 28 minutes after glucose addition. Mean and SEM of at least two biological replicates performed in duplicate. *p<0.05; p<0.01;*p<0.001; ****p<0.0001 as determined by (FIG. 19A) t-test of slopes calculated from linear fit of 0-2 minutes relative to buffer, or (FIG. 19B) comparison to DMSO+glucose with a one way ANOVA and Dunnett's multiple comparison post-test.

Having established that the putative EPMs are antimicrobial in mammalian cells, activity of the EPMs was further analyzed. While the Hoechst accumulation assay is a good first approximation of anti-efflux pump activity, quantification of export in real time based on glucose-dependence is a more specific assay for pump inhibition. Nile Red is an efflux pump substrate that becomes strongly fluorescent upon partitioning into the cytoplasmic membrane and possibly the inner leaflet of the outer membrane. Cells were preloaded with Nile Red and then treated with glucose to energize the efflux pumps and stimulate Nile Red export. Incubation with PAβN or any of the three EPMs reduced the rate and extent of Nile Red export upon glucose addition in a dose dependent manner (FIGS. 6A, 19A, 8). Washout of PAβN, EPM30 or EPM43 prior to adding glucose partially restored Nile Red export, suggesting the activity of these compounds, compared to EPM35, is readily reversible (FIG. 8). Moreover, a similar glucose-dependent assay using a different pump substrate, ethidium bromide, further demonstrated that all three EPMs reduced efflux pump export (FIG. 19B). These observations indicate that the three EPMs inhibit energy-dependent efflux pump activity.

Example 13. Bacterial Membranes Remain Intact Upon Exposure to the Three EPMs

Figure 20A:
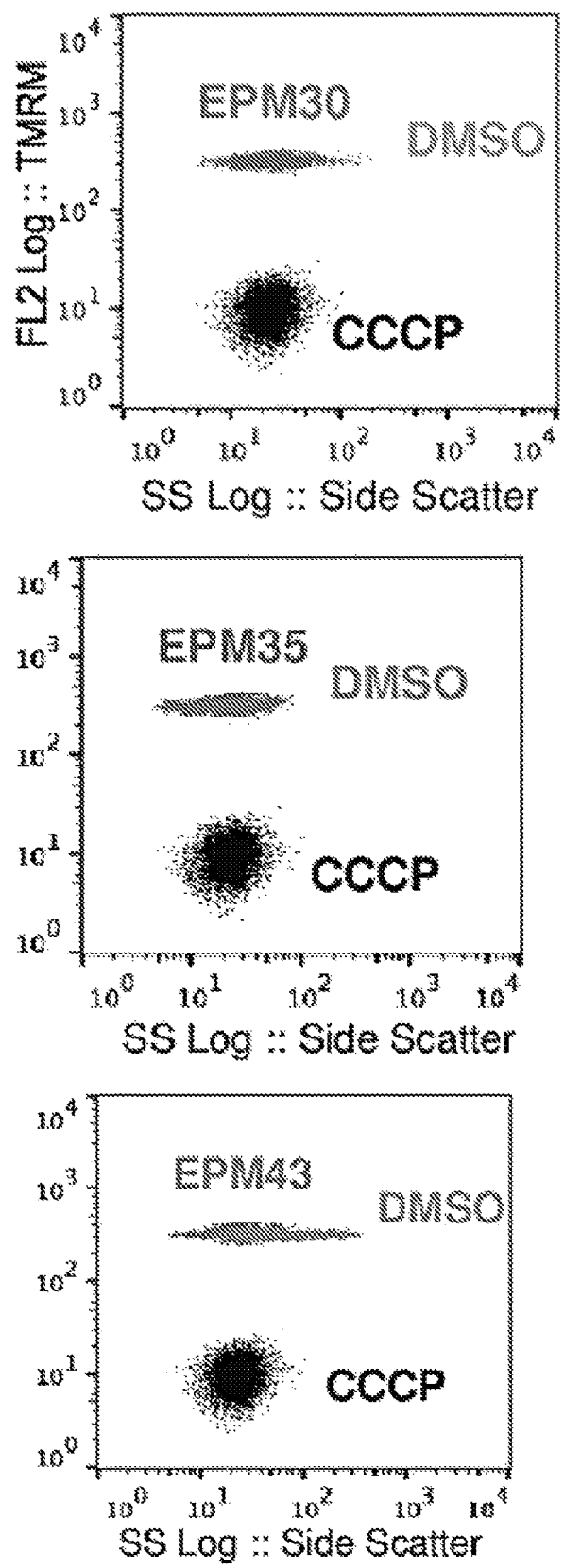
FIGS. 20A and 20B depict Bacteria treated with DMSO or EPMs [100 µM] but not CCCP [1 mM] acquire TMRM staining within 30 minutes.
Figure 20B:
Figure 20C:
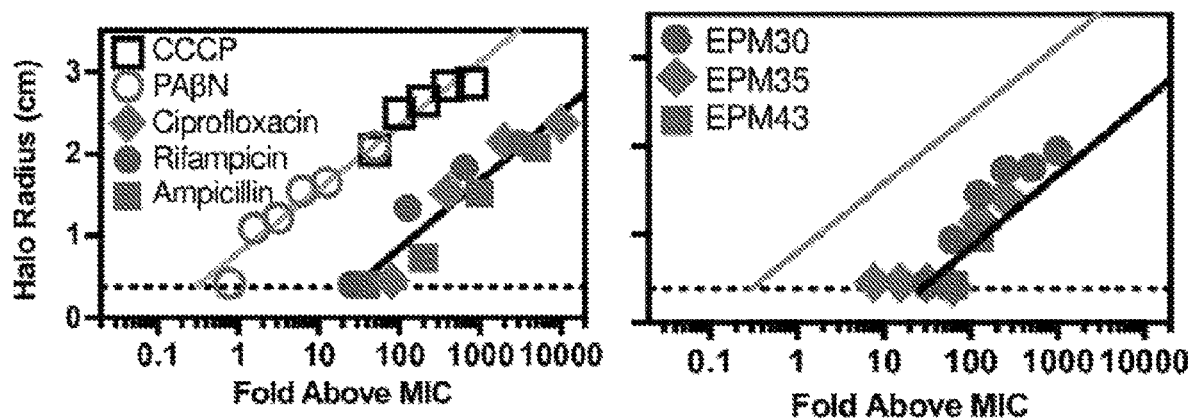
FIG. 20C depicts disk diffusion assays; the radius of the zone of growth inhibition after 16 hours of exposure to compound across a dose range. Black lines, semilog fit for the combined antibiotic data; gray lines, semilog fit for CCCP and PAβN; dotted line, limit of detection (disk radius). Average of two measurements from each image captured from one experiment representative of two independent experiments.

Since efflux pumps rely upon the proton motive force or ATP to provide 210 the energy for the transport of substrates, chemicals that disrupt the inner membrane may indirectly inhibit efflux. To establish whether the three EPMs alter bacterial inner membrane potential, their effect on the incorporation of the voltage-sensitive dye Tetramethylrhodamine methyl ester (TMRM) was observed. After 30 minutes of exposure to the ionophore CCCP, TMRM levels in cells were approximately 50-fold lower than upon treatment with DMSO, but treatment with any of the three EPMs did not alter TMRM signal (FIGS. 20A, 20B). These observations suggest that membrane potential remains intact in the presence of the EPMs. To establish whether a longer incubation with the EPMs may compromise membrane integrity, the effect of the EPMs on bacterial swimming, an energy intensive activity was monitored over 15 hours (FIGS. 20C, 10). Bacteria were injected into the center of soft-agar plates and 10 µl of compound was pipetted onto paper disks on the periphery (41). Control compounds included CCCP and PAβN, which disrupts membranes over long (>30 minutes) exposures. Since swimming overnight also requires bacterial growth, we tested whether filters containing bacteriostatic antibiotics prevented swimming beyond growth inhibition. Neither the three EPMs nor the conventional antibiotics inhibited swimming relative to their MIC, as compared to CCCP and PAβN, further suggesting that the EPMs do not interfere with bacterial energy production across the inner membrane.

Figure 20D:
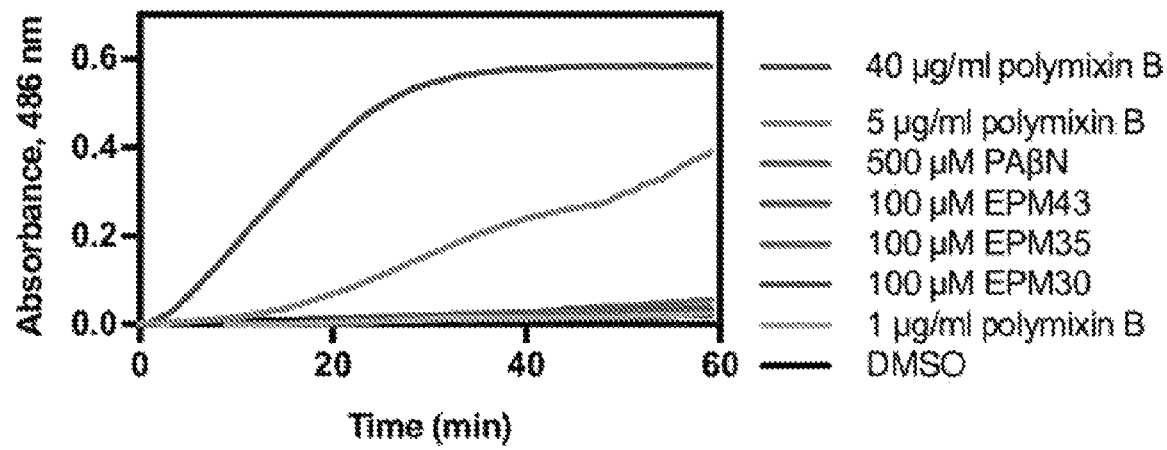
FIGS. 20D and 20E depict nitrocefin access to the periplasm as monitored by nitrocefin [100 µM] hydrolysis in the presence of the indicated concentrations of compounds.

A second class of chemicals that appears to interfere with bacterial efflux does so by permeabilizing the outer membrane, which allows substrates to diffuse into the periplasm. Therefore the EPMs were tested to determine whether they enable the chromogenic beta-lactam nitrocefin to access the periplasm and be hydrolyzed 233 by beta-lactamase. Compared to control compounds PAβN or polymyxin B, a pore-forming antimicrobial peptide, the EPMs did not increase nitrocefin permeation of the outer membrane (FIG. 20D), suggesting they do not disrupt efflux by increasing bacterial outer membrane permeability.

Example 14. The Hit Compounds are not Antibacterial in Standard Bacterial Medium To establish whether the hit compounds have minimum inhibitory concentrations (MICs) in broth that are similar to their $IC_{50S}$ in host cells (see: FIG. 18), bacterial growth was examined in their presence using standard rich laboratory media, Mueller Hinton Broth. The MICs of EPM30, EPM35, and EPM43 respectively were 100 µM (µg/mL), 400 µM (186 µg/mL), and >400 µM (113 µg/mL), for three Salmonella strains: the strain used in the SAFIRE screen (SL1344), a tetracycline-resistant derivative of SL1344 with demonstrated increased production of AcrAB (MAR1), and a clinical MDR Salmonella isolate (S10801). These MIC values are considerably higher than the $IC_{50S}$ observed in host cells and higher than MICs observed for traditional antibiotics, which are usually in the 1-10 µg/mL range. Thus, the three putative EPMs may not function like traditional antibiotics and yet are potent in the context of the host cell.

Example 15. The Three EPMs Sensitize Bacteria to Antimicrobial Peptides

Next, it was determined why the EPMs kill bacteria in mammalian cells at 10-fold or more lower concentrations than they inhibit efflux in broth. One possibility is that the presence of antimicrobial peptides (AMPs) within host cells plays a role. Mammalian cells constitutively express AMPs and increase AMP expression in response to infection. It was found that in broth the combination of each EPM with either the bacterial derived polymyxin B or the human cathelicidin AMP LL37, but not individual treatments, significantly inhibited Salmonella growth (FIG. 7). These data suggest at least three possibilities: EPMs may potentiate AMP activity, AMPs may potentiate EPM activity, or both.

Figure 14:
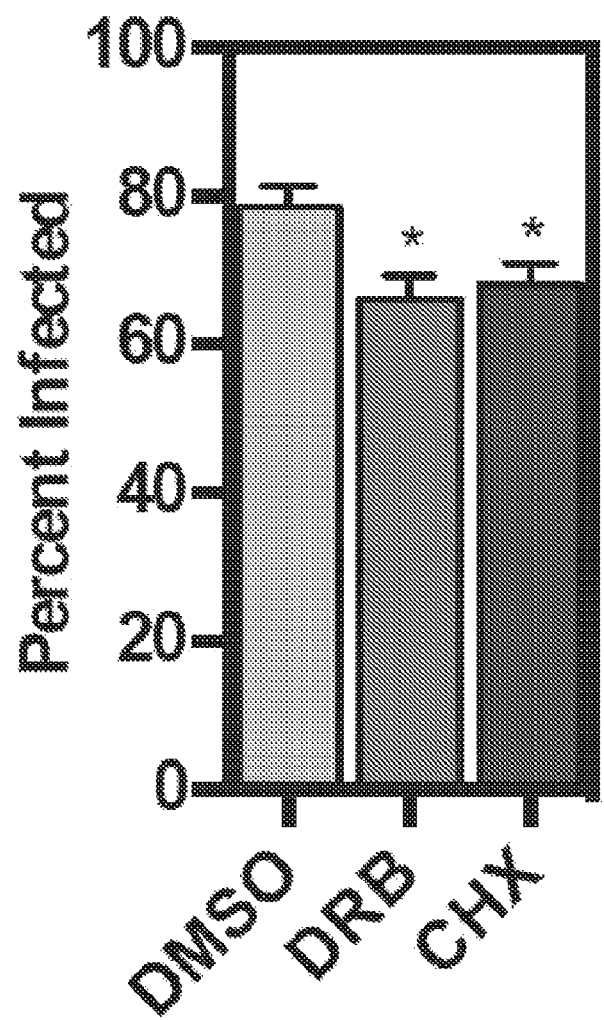
FIG. 14 depicts that inhibition of transcription or translation decreases infection. Data from FIG. 13A were plotted to show basal infection in the absence of EPM treatment. Data shown are mean+SEM of three independent biological replicates.
Figure 20E:
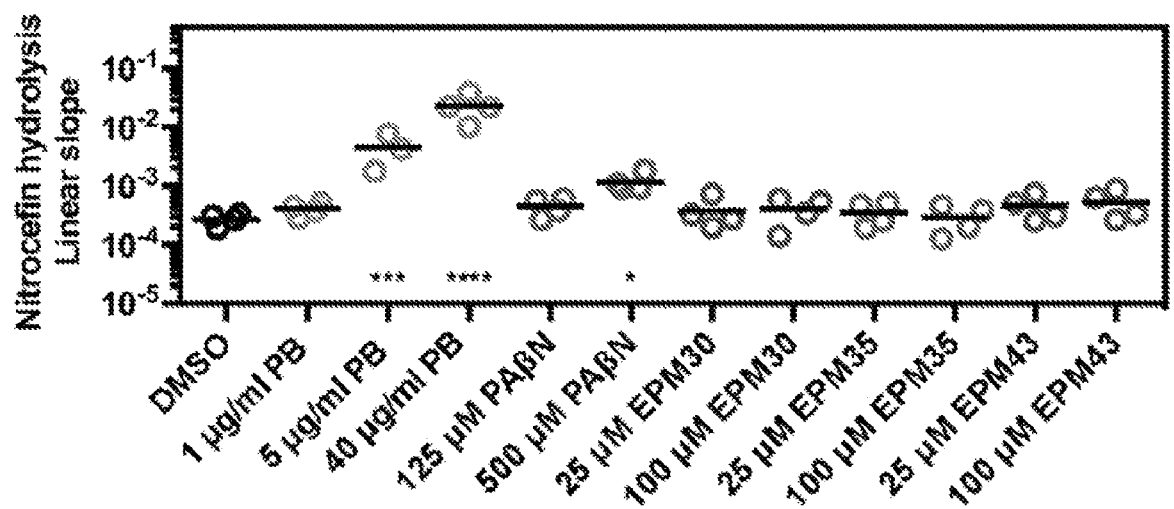
Figure 21:
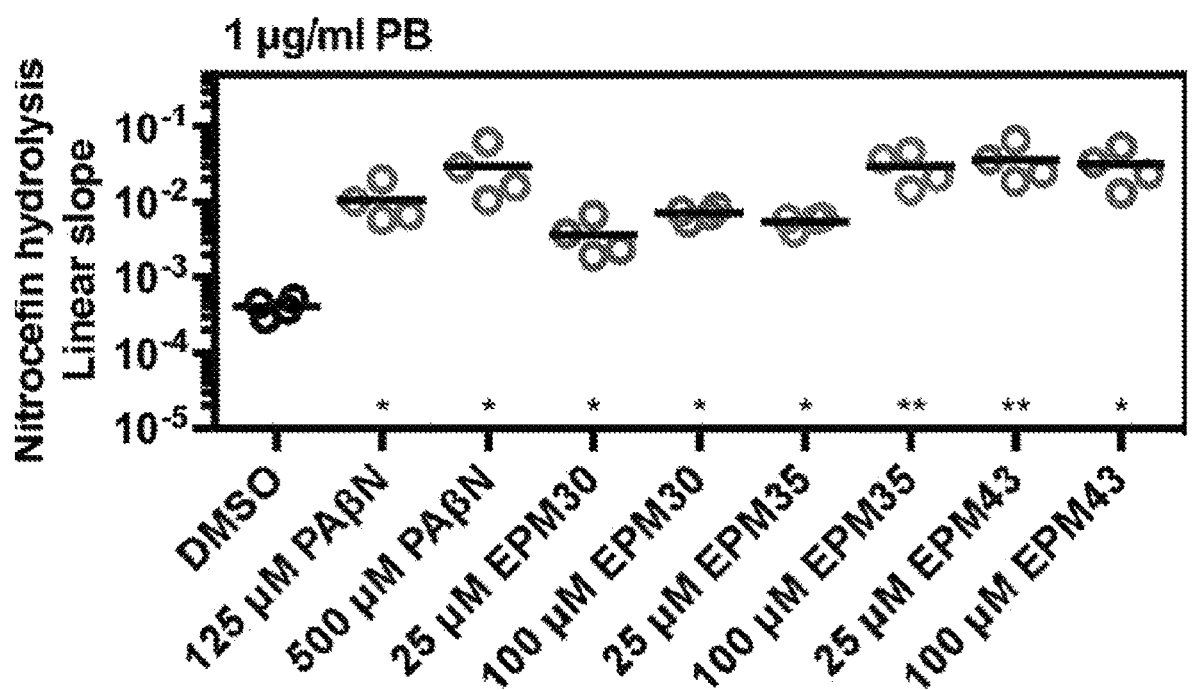
FIG. 21 depicts that EPMs sensitize bacteria to antimicrobial peptides. Nitrocefin access to the periplasm in the presence of a non-permeabilizing concentration of PB [1 µg/ml] and the indicated concentrations of EPMs, quantitated as in FIG. 5E. *p<0.05, **p<0.01 by one-way ANOVA with Dunnett's post-test.

To distinguish between these possibilities, it was first determined that bacterial exposure to polymyxin B concentrations high enough to allow nitrocefin access to the periplasm (5 µg/mL, FIGS. 20D, 20E) did not enhance the ability of the EPMs to increase Hoechst accumulation (FIG. 14). Similarly, cotreatment of polymyxin B with EPMs did not synergistically increase Nile Red retention compared to polymyxin B or EPMs alone (FIG. 14). These observations suggest that the membrane-damaging activity of polymyxin B did not potentiate EPM blockage of efflux pumps. Next, it was observed that low concentrations of polymyxin B (1 µg/mL), which do not by themselves allow nitrocefin access to the periplasm (FIGS. 20D, 20E), did indeed increase the rate of nitrocefin hydrolysis in the presence of EPMs (25 µM) (FIG. 21). It thus appears that EPMs potentiate AMPs with regard to both nitrocefin entry into the periplasm and bacterial growth inhibition. Therefore, EPMs may decrease the effective concentration of AMPs and, for this reason, have indirect antibacterial activity in the context of the host.

Example 16. EPM35 and EPM43 have Anti-Efflux Activity in MDR ESKAPE Pathogens

Figure 22A:
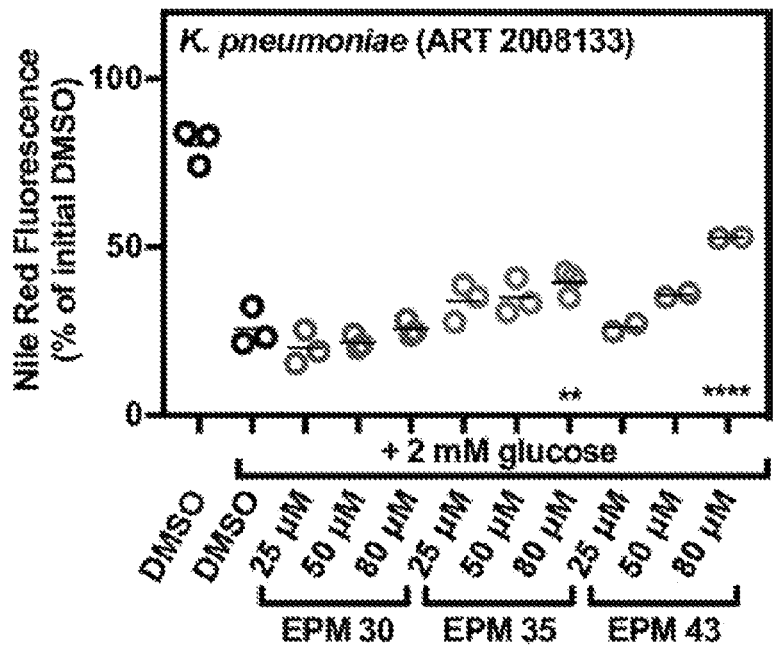
FIGS. 22A-D detail defined strains obtained from BEI resources examined for Nile Red retention after glucose addition in the presence of the indicated compound. *p<0.05; p<0.01; *p<0.001; ****p<0.0001 as determined by comparison to DMSO+glucose with a one-way ANOVA and Dunnett's multiple comparison post-test.
Figure 22B:
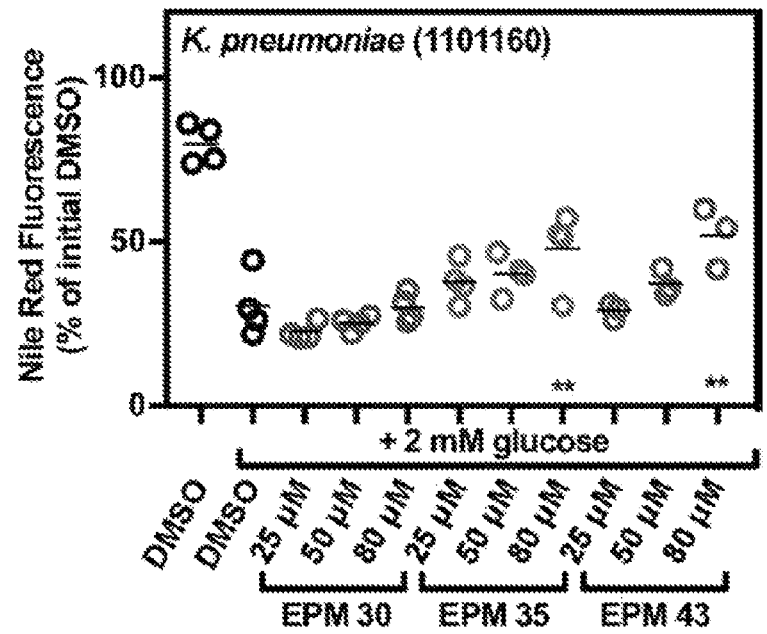
Figure 22C:
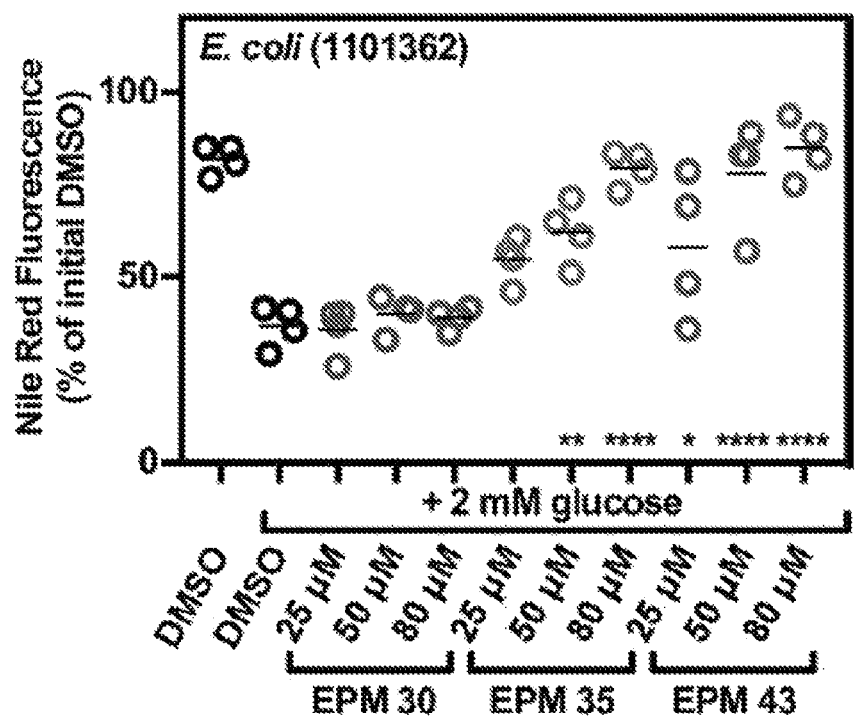
Figure 22D:
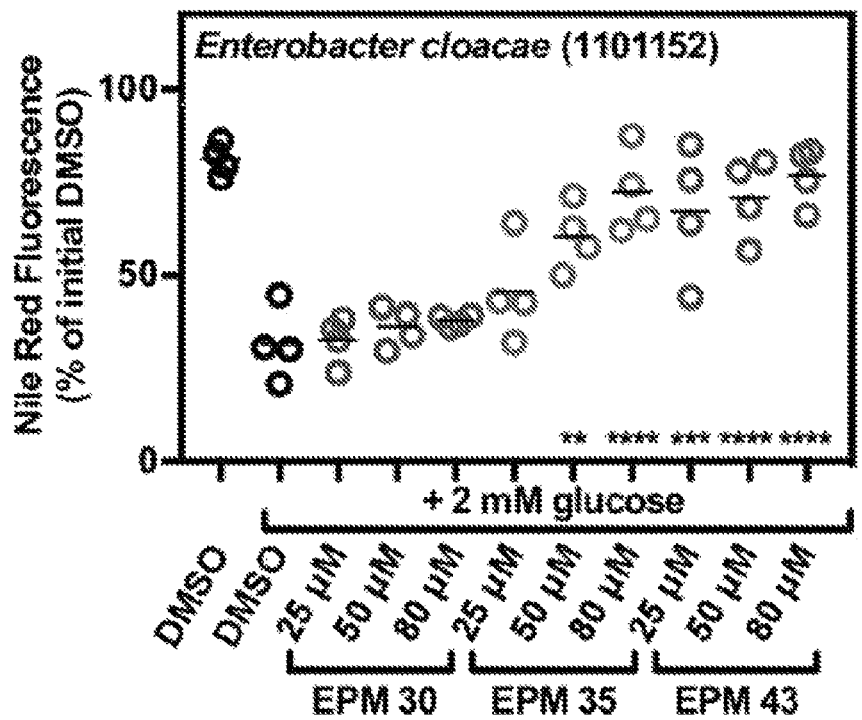

Six pathogens that cause the bulk of MDR nosocomial infections have been dubbed the ESKAPE pathogens: Enterococcus faecium, Staphylococcus aureus, Klebsiella pneumoniae, Acinetobacter baumannii, Pseudomonas aeruginosa, and Enterobacter species (56). EPM35 and EPM43 significantly reduced Nile Red export in MDR clinical isolates of K. pneumoniae and Enterobacter cloacae in addition to E. coli (FIGS. 22A, 22D), suggesting these two compounds have biological relevance in MDR strains beyond Salmonella.

Referring to FIGS. 22A-22D: Defined strains obtained from BEI resources were examined for Nile Red retention after glucose addition in the presence of the indicated compound. *p<0.05; p<0.01; *p<0.001; ****p<0.0001 as determined by comparison to DMSO+glucose with a one-way ANOVA and Dunnett's multiple comparison post-test.

Materials and Methods

The following materials and methods were utilized in the examples described herein.

Bacterial Strains

Salmonella enterica serovar Typhimurium strain SL1344 expressing GFP from the sifB promoter was used for screening and validation experiments. Saturated overnight cultures grown in LB with 30 µg/ml streptomycin and 30 µg/ml kanamycin were diluted to an OD of 0.001 and frozen in 100 µL aliquots at −80° C. with a final concentration of 20% glycerol. Prior to infection, aliquots were thawed into 5 mL cultures of LB with 30 µg/ml streptomycin and 30 µg/ml kanamycin and grown for 18 hours at 37° C. with aeration. Additional strains used for characterization experiments were routinely grown in LB media with 30 µg/ml streptomycin. These strains included wild-type SL1344, MAR1, and strain SM022 containing rpsM::GFP. The acrAB::kan and macAB::kan strains were constructed using a method described in the literature. The multidrug resistant isolate 510801 (BEI Resources, NIAID, NIH) was grown in 30 µg/ml streptomycin, 50 µg/ml ampicillin, 10 µg/ml tetracycline; this strain was originally isolated from a calf with sepsis.

Cell Culture

Murine macrophage-like RAW 264.7, HeLa human epithelial cells, and HepG2 human liver cells were grown in DMEM high glucose (Sigma) supplemented with 10% fetal bovine serum, 2 mM L-glutamine, 1 mM sodium pyruvate, 10 mM HEPES, and 50 µM β-mercaptoethanol. All cell lines were maintained in a 5% $CO_2$ humidified atmosphere at 37° C. For screening, frozen aliquots of RAW 264.7 were thawed and allowed to expand for 3 days prior to seeding; other experiments were performed with cultures between passages 4 and 20.

Bacterial Infections for SAFIRE and CFU Plating

For high-throughput screening and validation, $7 \times 10^3$ macrophages in 40 μL or $3 \times 10^4$ macrophages in 100 μL were seeded in 384- or 96-well black-walled, glass-bottomed plates (Brooks Automation). Twenty-four hours post seeding, bacteria in 20 or 50 μL PBS were added to a final concentration of $1 \times 10^7$ cfu/mL; we determined that these conditions resulted in infection of approximately 70% of macrophages at 18 hours post-infection with minimal macrophage toxicity. Forty-five minutes after bacterial addition, 20 or 50 μL gentamicin was added to a final concentration of 40 μg/mL. We empirically determined that this concentration did not affect intracellular infection but was sufficient to inhibit replication of extracellular bacteria. At 2 hours post-infection, 200 or 500 nL compound was added using a pin tool (CyBio) to yield a final concentration of 25 μM. Each assay plate included rifampicin and DMSO controls. In some experiments, media was removed and replaced with fresh medium containing 40 μg/mL gentamicin and the indicated concentrations of drugs. At 17.5 hours post-infection, PBS containing MitoTracker Red CMXRos (Life Technologies) was added to yield a final concentration of 300 nM (384-well) or 100 nM (96-well). Thirty minutes later, 16% paraformaldehyde was added to a final concentration of 1-2% and incubated at room temperature for 15 minutes. Wells were washed twice with PBS and stained for 20 minutes with 1 μM DAPI; wells were washed twice and stored in 90% glycerol in PBS until imaging.

Infections to determine S.Tm CFUs were performed as described above, except macrophages were seeded in 96-well tissue culture coated plates (Greiner). At 18 hours post-infection, wells were washed three times in PBS, lysed with 30 μL 0.1% Triton X-100, diluted and plated to determine colony-forming units.

Infections of HeLa cells with *Salmonella* were performed as above in 96-well plates, except $1 \times 10^4$ cells were seeded, cells were infected with S.Tm constitutively expressing GFP from the rpsM locus because sifB is poorly expressed in HeLa cells, and plates were spun for 5 minutes at 500× g after addition of bacteria to enhance infection.

Infections with *Listeria monocytogenes* were performed as described in the literature. Briefly, $5 \times 10^4$ macrophages in 100 μL were seeded into 96-well plates. Twenty-four hours later, *Listeria monocytogenes* were grown to mid-log phase in BHI medium, diluted to $OD_{600}$ 0.01 in PBS, and 50 μL was added to macrophages. After 30 minutes, cells were washed in PBS and 100 μL fresh media was added. At 1 hour post-infection, 100 μL media with gentamicin was added to yield a final concentration of 50 μg/ml gentamicin. At 2 hours post-infection, infected cells were treated with compound as described above. At 6 hours post-infection, cells were processed for CFUs as described above.

Real-Time Reverse Transcription PCR

Infections were performed as described above, except that $8 \times 10^4$ RAW 264.7 macrophages were seeded in 6-well dishes and volumes were scaled for the larger culture volume. At indicated timepoints, wells were washed twice with PBS and RNA was extracted using the RNeasy mini kit (Qiagen) including Qiashredder homogenization and on-column DNase treatment. RNA yields ranged from 5-40 ng. First-strand cDNA was synthesized from 250 ng of total RNA using the iScript cDNA synthesis kit (BioRad) and diluted 10-fold. Quantitative PCR (qPCR) for the indicated genes was performed using the following primers: Hprt (GCGTTGGGCTTACCTCACT [SEQ ID NO: 1], ATCGCTAATCACGACGCTGG [SEQ ID NO: 2]); Sert (TTGGATAGTACGTTCGCAGGC [SEQ ID NO: 3], ACCACGATGAGCACAAACCA [SEQ ID NO: 4]); Camp (CAGCTGTAACGAGCCTGGTG [SEQ ID NO: 5], CACCTTTGCGGAGAAGTCCA [SEQ ID NO: 6]). Hprt was selected as the reference gene based on validation experiments. The qPCR reactions were performed in technical duplicates and contained 8 μL diluted cDNA, 200 nM of each primer, and 10 μL 2× Power SYBR Green (Applied Biosystems) in 20 μL total volume. Reactions were run on an Eppendorf Realplex² MasterCycler with the following cycling conditions: 10 minutes at 95° C., then 40 cycles at 95° C. for 15 seconds and 60° C. for 60 seconds. Melting curve analysis of the PCR reaction showed a single amplicon for each target. No-template and no-reverse-transcriptase controls showed no product. Amplification results were baseline corrected, followed by manual determination of the threshold for each gene. The resulting $C_T$ values were analyzed as follows: (i) The mean $C_T$ of qPCR technical duplicates was determined for each sample. (ii) Sert and Camp expression for each sample was normalized to that of Hprt, resulting in the $\Delta C_T$. (iii) Each sample was normalized to the mean of the uninfected samples for that experiment, resulting in the $\Delta\Delta C_T$ for that sample. (iv) The mean of sample replicates from the same experiment was calculated. (v) Fold expression and error were calculated using the $2^{-\Delta\Delta C_T}$ equation.

Image Acquisition, MATLAB®-Based Screening Analysis, and Hit Selection

High magnification images were acquired on an Olympus IX81 inverted widefield microscope. For screening imaging, three-color images were acquired at 10× or 20× on a Cellomics ArrayScan VTI (Thermo) and exported to DIB files. At least two images were taken per well for all experiments. We developed an automated MATLAB® script to quantify intracellular bacterial load; scripting packages have been deposited on MATLAB® File Exchange (https://www.mathworks.com/matlabcentral/fileexchange/), deposited as "SAFIRE_ArrayScan" and "SAFIRE_OlympusIX81.". Briefly, the algorithm identifies macrophage borders via watershed segmentation using DAPI and MitoTracker signal. In order to identify bacteria, the user supplies an empirically determined GFP threshold that maximizes signal to noise. Within each macrophage, the number of pixels above the GFP threshold is counted. If more than 2 pixels are above the GFP threshold, the macrophage is labeled infected. The script calculates the percentage of macrophages infected in the image. To determine infection area for each cell, the number of GFP+ positive pixels was divided by the number of total pixels in the cell. Average infection area was determined by averaging across all cells within the image. Raw data for at least 2 images from the same well are averaged to yield one value for each well. Raw screening data was subjected to B-score normalization because we identified significant row and column effects by the method described in the literature. To determine significance of screening data, we employed the modified one-sample t-test by fitting the variances of replicates to an inverse gamma distribution. Assay positives were defined as having a p-value less than 0.05 and a B-score outside one standard deviation from the mean.

Cytotoxicity Assays

Cytoxocity was determined using the Pierce Lactate Dehydrogenase (LDH) Cytoxicity Assay. HepG2 liver cells were plated at $5\times10^4$ in 96 well tissue culture plates and allowed to settle overnight. Cells were treated with a 2-fold dilutions of each compound for 16 hours. Fifty microliters of conditioned media was mixed with the LDH assay reagent, incubated for 30 minutes, and absorbance was read at 490 and 680 nm. Curve fitting to determine CC50s was performed using GraphPad Prism; the CC50 is defined as 50% of the maximum LDH release as determined by lysed macrophages. There was no spontaneous LDH release or LDH present in the media.

Broth Activity Assays

Overnight *Salmonella* cultures were washed 3 times in PBS and diluted to an OD of 0.01 in Mueller Hinton Broth in 96-well flat bottom plates. Compound was added using a pin tool (CyBio) or manually, yielding a final concentration of no more than 1% DMSO. Plates were grown at 37° C. shaking and OD600 was monitored using a BioTek Eon incubator shaker microplate absorbance reader. For experiments in defined media, bacteria were grown in M9 minimal media supplemented with 100 mM Tris pH 7.4, 0.35% glycerol, 0.002% histidine, 10 mM $MgCl_2$, and 0.1% casamino acids. Where indicated, media was supplemented with 5 µg/ml polymyxin B or 0.2 mM $H_2O_2$. For experiments with LL-37, bacteria were grown in M9 minimal media supplemented with 0.4% dextrose, 0.004% histidine, 1 mM $MgSO_4$, and 5 µg/ml LL-37. For checkerboard assays, MIC was defined as the concentration at which no growth was visually observed.

Efflux Assays

Hoechst accumulation assays were performed essentially as described in the literature. Briefly, overnight *Salmonella* cultures were washed 3 times in PBS and diluted to an OD of 0.1 in PBS with 2.5 µM Hoechst 33342 in the presence of the indicated concentrations of compounds. Fluorescence was monitored on a Biotek Synergy 2 with a 360/40 nm excitation filter and 460/40 nm emission filter. The maximum Hoechst fluorescence over 60 minutes of incubation was normalized to the signal from the equivalent number of heat-killed bacteria, after subtraction of autofluroescent signal determined from compound incubated in the absence of bacteria. Curve fitting to determine EC50s was performed using GraphPad Prism.

Nile Red assays were adapted from an established protocol. Briefly, overnight *Salmonella* cultures were grown in Mueller-Hinton cation-adjusted broth (Sigma), washed, and resuspended at an OD600 of 2.0. Cells were incubated in 10 µM Nile Red for 3 hours at 37° C. with aeration, then moved to room temperature for 1 hour. After pelleting at 2000× g, dye-loaded cells were aliquoted and combined with compound at the indicated concentrations. Two hundred microliters was loaded into 96-well black walled plates (Greiner) and read using a Varioskan Flash Multimode Reader with 540 nm excitation and 625 nm emission filters. We observed that during loading into plates (~20 minutes), bacteria were able to efflux Nile Red even in the absence of glucose (FIG. 8A). To activate efflux, glucose was added to a final concentration of 2 mM. In some experiments, bacteria were treated with drug for 15 minutes, pelleted at 16,000×g, resuspended in fresh buffer, and stimulated with 2 mM glucose. All wash and incubation steps were performed in PBS with 1 mM MgCl2; incubations were performed in glass tubes to reduce adhesion of Nile Red.

Swimming Assays

Saturated overnight cultures were diluted to an OD600 of 0.01 in LB and 1 µL was injected into the center of low agar (0.25%) LB plates. Ten microliters of the indicated compounds were added to sterilized Whatman paper disks (diameter 0.7 cm) placed equidistant from the plate center. Plates were incubated lid up at 37° C. overnight (no change in halo was observed between 14-24 hours incubation), imaged using a Gel Logic 200 imaging system, and halo radius (distance between center of disk and outermost edge of halo) was measured using ImageJ.

Mouse Infections

These studies were carried out in strict accordance with the recommendations in the *Guide for the Care and Use of Laboratory Animals* of the National Institutes of Health, and all protocols were approved by the University of Colorado Institutional Committees for Biosafety and for Animal Care and Use. Bacteria were grown overnight in LB, then diluted in PBS. Seven week old C57/B16 female mice were intraperitoneally injected with $1\times10^4$S.Tm in 100 µL. Thirty minutes later, mice received two intraperitoneal injections: 25 mg/kg tetracycline in 150 µL PBS or PBS alone, and 50 mg/kg EPM35 in 100 µL DMSO or DMSO alone. Drug injections were repeated at 24 hours post-infection. At 30 hours post-infection, mice were humanely euthanized using carbon dioxide asphyxiation followed by cervical dislocation. Spleens and livers were harvested, homogenized, diluted in PBS, and plated to enumerate S.Tm CFUs.

What is claimed is:

1. A pharmaceutical composition comprising an effective amount of an efflux pump modulator compound and a pharmaceutically acceptable carrier, wherein the efflux pump modulatory compound has one of the structure:

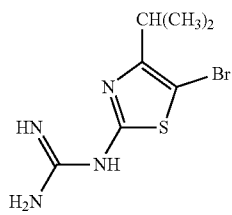

(EPM30)

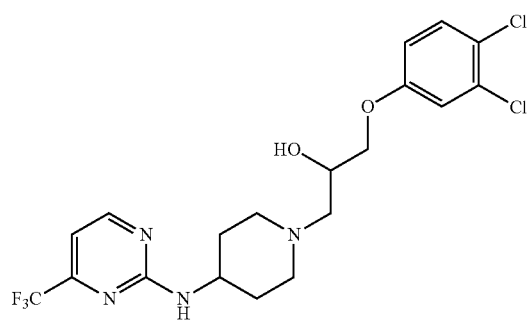 [SMILES: OC(COc1ccc(Cl)c(Cl)c1)CN1CCC(Nc2nccc(C(F)(F)F)n2)CC1]

(EPM35), or

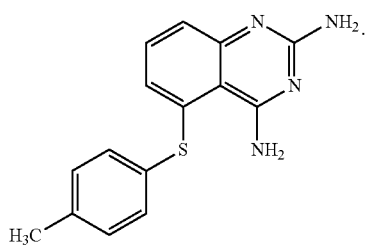 [SMILES: Cc1ccc(Sc2cccc3nc(N)nc(N)c23)cc1]

(EPM43).

2. A method of treating a bacterial pathogen in a subject, the method comprising administering to the subject a therapeutically effective amount of an efflux pump modulator (EPM) compound, wherein the EPM is

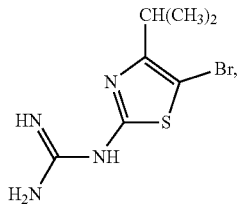

(EMP 30)

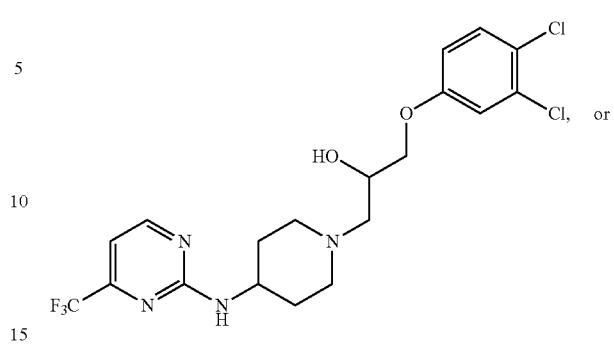

(EMP 35)

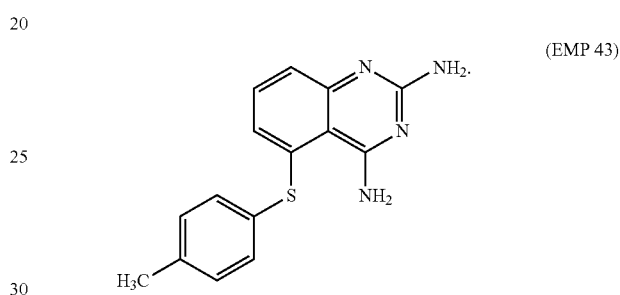

(EMP 43)

3. The method of claim 2, further comprising administering an antimicrobial peptide or an antibiotic.

4. The method of claim 3, wherein the antibiotic comprises tetracycline.

5. The method of claim 3, wherein the antimicrobial peptide comprises polymyxin B.

6. The method of claim 2, wherein the EPM compound comprises EPM30.

7. The method of claim 2, wherein the EPM compound comprises EPM35.

8. The method of claim 2, wherein the EPM compound comprises EPM43.

9. The method of claim 2, wherein the bacterial pathogen comprises one or more of a *Salmonella* sp., *K. pneumoniae*, *Enterobacter cloacae*, or *E. coli*.

10. The pharmaceutical composition of claim 1, wherein the pharmaceutically acceptable carrier is present an amount ranging from 1-99%.

11. The pharmaceutical composition of claim 1, wherein the pharmaceutical composition is an aqueous composition which is formulated at a pharmaceutically acceptable pH and tonicity.

* * * * *

SEQUENCE LISTING

<160> NUMBER OF SEQ ID NOS: 6

<210> SEQ ID NO 1
<211> LENGTH: 19
<212> TYPE: DNA
<213> ORGANISM: Artificial Sequence
<220> FEATURE:
<223> OTHER INFORMATION: Hprt Primer

```
<400> SEQUENCE: 1
gcgttgggct tacctcact                                                   19

<210> SEQ ID NO 2
<211> LENGTH: 20
<212> TYPE: DNA
<213> ORGANISM: Artificial Sequence
<220> FEATURE:
<223> OTHER INFORMATION: Hprt Primer

<400> SEQUENCE: 2
atcgctaatc acgacgctgg                                                  20

<210> SEQ ID NO 3
<211> LENGTH: 21
<212> TYPE: DNA
<213> ORGANISM: Artificial Sequence
<220> FEATURE:
<223> OTHER INFORMATION: Sert Primer

<400> SEQUENCE: 3
ttggatagta cgttcgcagg c                                                21

<210> SEQ ID NO 4
<211> LENGTH: 20
<212> TYPE: DNA
<213> ORGANISM: Artificial Sequence
<220> FEATURE:
<223> OTHER INFORMATION: Sert Primer

<400> SEQUENCE: 4
accacgatga gcacaaacca                                                  20

<210> SEQ ID NO 5
<211> LENGTH: 20
<212> TYPE: DNA
<213> ORGANISM: Artificial Sequence
<220> FEATURE:
<223> OTHER INFORMATION: Camp Primer

<400> SEQUENCE: 5
cagctgtaac gagcctggtg                                                  20

<210> SEQ ID NO 6
<211> LENGTH: 20
<212> TYPE: DNA
<213> ORGANISM: Artificial Sequence
<220> FEATURE:
<223> OTHER INFORMATION: Camp Primer

<400> SEQUENCE: 6
cacctttgcg gagaagtcca                                                  20
```